US010948487B2

(12) United States Patent
Mehra et al.

(10) Patent No.: US 10,948,487 B2
(45) **Date of Patent: *Mar. 16, 2021**

(54) PEPTIDES, DEVICES, AND METHODS FOR THE DETECTION OF EHRLICHIA ANTIBODIES

(71) Applicant: Zoetis Services LLC, Parsippany, NJ (US)

(72) Inventors: Rajesh K. Mehra, Union City, CA (US); Kenneth P. Aron, Union City, CA (US); Dennis M. Bleile, Union City, CA (US); Timothy P. Forsyth, Union City, CA (US); Jeremy D. Walker, Union City, CA (US); Cristina R. Cuesico, Union City, CA (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/552,381

(22) Filed: Aug. 27, 2019

(65) Prior Publication Data

US 2019/0391139 A1 Dec. 26, 2019

Related U.S. Application Data

(60) Continuation of application No. 15/608,560, filed on May 30, 2017, now Pat. No. 10,444,231, which is a continuation of application No. 14/842,440, filed on Sep. 1, 2015, now Pat. No. 9,696,300, which is a division of application No. 14/252,690, filed on Apr. 14, 2014, now Pat. No. 9,157,913, which is a continuation of application No. 14/052,296, filed on Oct. 11, 2013, now Pat. No. 9,651,546.

(60) Provisional application No. 61/712,578, filed on Oct. 11, 2012.

(51) Int. Cl.

| | |
|---|---|
| ***C07K 14/29*** | (2006.01) |
| ***G01N 33/543*** | (2006.01) |
| ***G01N 33/569*** | (2006.01) |
| ***C07K 17/14*** | (2006.01) |
| ***G01N 33/68*** | (2006.01) |

(52) U.S. Cl.

CPC ....... *G01N 33/54306* (2013.01); *C07K 14/29* (2013.01); *C07K 17/14* (2013.01); *G01N 33/56911* (2013.01); *G01N 33/6854* (2013.01); *G01N 2333/29* (2013.01); *G01N 2469/20* (2013.01)

(58) Field of Classification Search

None

See application file for complete search history.

(56) References Cited

U.S. PATENT DOCUMENTS

| | | | |
|---|---|---|---|
| 4,366,246 | A | 12/1982 | Riggs |
| 4,617,262 | A | 10/1986 | Maxim |
| 6,204,252 | B1 | 3/2001 | Murphy et al. |
| 6,207,169 | B1 | 3/2001 | Reed et al. |
| 6,231,869 | B1 | 5/2001 | Reed et al. |
| 6,284,238 | B1 | 9/2001 | Coughlin et al. |
| 6,306,402 | B1 | 10/2001 | Reed et al. |
| 6,355,777 | B1 | 3/2002 | Walker et al. |
| 6,451,315 | B1 | 9/2002 | Reed et al. |
| 6,544,517 | B1 | 4/2003 | Rikihisa et al. |
| 6,593,147 | B1 | 7/2003 | Barbet et al. |
| 6,893,640 | B2 | 5/2005 | Rikihisa et al. |
| 6,923,963 | B2 | 8/2005 | Rikihisa et al. |
| 6,964,855 | B2 | 11/2005 | O'Connor et al. |
| 7,063,846 | B2 | 6/2006 | Rikihisa et al. |
| 7,087,372 | B2 | 8/2006 | Lawton et al. |
| 7,183,060 | B2 | 2/2007 | O'Connor, Jr. |
| 7,204,992 | B2 | 4/2007 | McBride et al. |
| 7,407,770 | B2 | 8/2008 | O'Connor, Jr. |
| 7,445,788 | B2 | 11/2008 | Lawton et al. |
| 7,449,191 | B2 | 11/2008 | Lawton et al. |
| 7,482,128 | B2 | 1/2009 | Jensen et al. |
| 7,709,622 | B2 | 5/2010 | Rikihisa et al. |
| 7,744,872 | B2 | 6/2010 | O'Connor, Jr. |
| 7,888,491 | B2 | 2/2011 | Rikihisa et al. |

(Continued)

FOREIGN PATENT DOCUMENTS

| | | |
|---|---|---|
| CN | 1321190 A | 11/2001 |
| CN | 1367832 A | 9/2002 |

(Continued)

OTHER PUBLICATIONS

Cardenas, A. M. et al., "Enzyme-Linked Immunosorbent Assay with Conserved Immunoreactive Glycoproteins gp36 and gp19 Has Enhanced Sensitivity and Provides Species-Specific Immunodiagnosis of Ehrlichia canis Infection," Clinical and Vaccine Immunology, 14(2):123-128 (2007).

(Continued)

*Primary Examiner* — Mary Maille Lyons

(74) *Attorney, Agent, or Firm* — Cooley LLP

(57) ABSTRACT

The invention provides peptide compositions and mixtures useful for the detection of antibodies that bind to *Ehrlichia* antigens. The peptide compositions and mixtures comprise polypeptide sequences based on an immunogenic fragment of the *Ehrlichia* Outer Membrane Protein 1 (OMP-1) protein. The invention also provides devices, methods, and kits comprising such peptide compositions and mixtures useful for the detection of antibodies that bind to *Ehrlichia* antigens and the diagnosis of monocytic and/or granulocytic ehrlichiosis.

26 Claims, 5 Drawing Sheets

Specification includes a Sequence Listing.

(56) References Cited

U.S. PATENT DOCUMENTS

| | | | |
|---|---|---|---|
| 8,158,751 B2 | 4/2012 | O'Connor, Jr. | |
| 8,828,675 B2 | 9/2014 | Mehra et al. | |
| 9,157,913 B2 * | 10/2015 | Mehra | C07K 17/14 |
| 9,442,112 B2 | 9/2016 | Mehra et al. | |
| 9,470,682 B2 | 10/2016 | Mehra et al. | |
| 9,651,546 B2 * | 5/2017 | Mehra | C07K 14/29 |
| 9,696,300 B2 * | 7/2017 | Mehra | G01N 33/54306 |
| 9,851,352 B2 | 12/2017 | Mehra et al. | |
| 10,444,231 B2 * | 10/2019 | Mehra | C07K 14/29 |
| 2002/0120115 A1 | 8/2002 | Rikihisa et al. | |
| 2002/0132789 A1 | 9/2002 | Barbet et al. | |
| 2002/0160432 A1 | 10/2002 | Lawton et al. | |
| 2002/0177178 A1 | 11/2002 | Lawton et al. | |
| 2003/0022262 A1 | 1/2003 | McDonald et al. | |
| 2003/0103991 A1 | 6/2003 | Rikihisa | |
| 2003/0119082 A1 | 6/2003 | Lawton et al. | |
| 2003/0129161 A1 | 7/2003 | Chu | |
| 2005/0124015 A1 | 6/2005 | O'Connor et al. | |
| 2005/0142557 A1 | 6/2005 | Alleman et al. | |
| 2006/0189537 A1 | 8/2006 | O'Connor | |
| 2006/0211062 A1 | 9/2006 | O'Connor | |
| 2006/0234322 A1 | 10/2006 | Krah et al. | |
| 2007/0020733 A1 | 1/2007 | Lawton et al. | |
| 2007/0026474 A1 | 2/2007 | Lawton et al. | |
| 2007/0161782 A1 | 7/2007 | O'Connor | |
| 2008/0248497 A1 | 10/2008 | Beall et al. | |
| 2009/0004217 A1 | 1/2009 | Krah et al. | |
| 2009/0010956 A1 | 1/2009 | Rikihisa | |
| 2009/0042222 A1 | 2/2009 | O'Connor et al. | |
| 2009/0081695 A1 | 3/2009 | O'Connor et al. | |
| 2009/0081708 A1 | 3/2009 | O'Connor et al. | |
| 2009/0098583 A1 | 4/2009 | McDonald et al. | |
| 2009/0110691 A1 | 4/2009 | Krah et al. | |
| 2009/0155825 A1 | 6/2009 | Beall et al. | |
| 2009/0176208 A1 | 7/2009 | Brodie | |
| 2010/0081125 A1 | 4/2010 | Xia et al. | |
| 2010/0267166 A1 | 10/2010 | Nazareth et al. | |
| 2011/0124125 A1 | 5/2011 | Mehra et al. | |
| 2014/0121125 A1 | 5/2014 | Mehra et al. | |
| 2014/0212898 A1 | 7/2014 | Mehra et al. | |
| 2015/0024417 A1 | 1/2015 | Mehra et al. | |
| 2015/0285797 A1 | 10/2015 | Mehra et al. | |
| 2016/0054313 A1 | 2/2016 | Mehra et al. | |
| 2017/0082622 A1 | 3/2017 | Mehra et al. | |
| 2018/0067115 A1 | 3/2018 | Mehra et al. | |
| 2018/0106792 A1 | 4/2018 | Mehra et al. | |

FOREIGN PATENT DOCUMENTS

| | | |
|---|---|---|
| CN | 1473166 A | 2/2004 |
| CN | 1735684 | 2/2006 |
| CN | 101970463 A | 2/2011 |
| CN | 103060468 A | 4/2013 |
| EP | 1026949 B1 | 9/2010 |
| EP | 2056112 B1 | 3/2012 |
| JP | 2002-515763 A | 5/2002 |
| JP | 2002-527042 A | 8/2002 |
| JP | 2003-517282 A | 5/2003 |
| JP | 2005-502586 A | 1/2005 |
| JP | 2006-505270 A | 2/2006 |
| WO | WO 1999/013720 A1 | 3/1999 |
| WO | WO 2000/012688 A1 | 3/2000 |
| WO | WO 2000/032745 A2 | 6/2000 |
| WO | WO 2001/007625 A2 | 2/2001 |
| WO | WO 2002/022782 A2 | 3/2002 |
| WO | WO 2002/057794 A2 | 7/2002 |
| WO | WO 2000/006744 A1 | 8/2002 |
| WO | WO 2005/087803 A1 | 9/2005 |
| WO | WO 2006/138509 A2 | 12/2006 |
| WO | WO 2008/137881 A2 | 11/2008 |
| WO | WO 2009/039414 A2 | 3/2009 |
| WO | WO 2011/063235 A2 | 5/2011 |
| WO | WO 2014/059274 A1 | 4/2014 |
| WO | WO 2015/153949 A2 | 10/2015 |

OTHER PUBLICATIONS

Crocquet-Valdes, P. A. et al., "Immunization with Ehrlichia P28 Outer Membrane Proteins Confers Protection in a Mouse Model of Ehrlichiosis," Clinical and Vaccine Immunology, 18(12):2018-2025 (2011).

De Farias Rotondano, T. E. et al., "An assessment of whole blood and fractions by nested PCR as a DNA source for diagnosing canine ehrlichiosis and anaplasmosis," The Scientific World Journal, vol. 2012; Article ID 605743 (2012).

Doyle, C. K. et al., "Differentially Expressed and Secreted Major Immunoreactive Protein Orthologs of Ehrlichia canis and E. chaffeensis Elicit Early Antibody Responses to Epitopes on Glycosylated Tandem Repeats," Infect. Immun., 74(1):711-720 (2006).

Eliasson, M. et al., "Chimeric IgG-binding receptors engineered from staphylococcal protein A and streptococcal protein G," J. Biol. Chem., 263(9):4323-4327 (1988).

European Application No. EP 15772535.9, Extended European Search Report dated Sep. 7, 2017, 10 pages.

First Office Action and Search Report for Chinese Patent Application No. 201080061669.1, dated Dec. 4, 2013, 9 pages.

Gusa, A. A. et al., "28 kDa major outer membrane protein P28, partial [Ehrlichia ewingii]," Genbank Accession No. AAG44899.1 (Nov. 6, 2001), 1 page.

Gusa, A. A. et al., "Identification of a p28 gene in Ehrlichia ewingii: evaluation of gene for use as a target for a species-specific PCR diagnostic assay," Journal of Clinical Microbiology, 39(11):3871-3876 (2001).

International Search Report and Written Opinion for International Application. No. PCT/US2010/057430, dated Aug. 10, 2011, 11 pages.

International Preliminary Report on Patentability for International Application. No. PCT/US2010/057430, dated May 22, 2012, 6 pages.

International Search Report and Written Opinion for International Application No. PCT/US2013/064536, dated Feb. 6, 2014, 9 pages.

International Preliminary Report on Patentability for International Application No. PCT/US2013/064536, dated Apr. 14, 2015, 7 pages.

International Search Report and Written Opinion for International Application No. PCT/US2015/024208, dated Jul. 20, 2015, 8 pages.

International Preliminary Report on Patentability for International Application No. PCT/US2015/024208, dated Oct. 4, 2016, 5 pages.

Knowles, T. T. et al., "Characterization of the major antigenic protein 2 of Ehrlichia canis and Ehrlichia chaffeensis and its application for serodiagnosis of ehrlichiosis," Clinical and Vaccine Immunology, 10(4):520-524 (2003).

Liddell, A. M. et al., "Predominance of Ehrlichia ewingii in Missouri dogs," J. Clin. Microbiol., 41(10):4617-4622 (2003).

Luo, T. et al., "Molecular Characterization of Antibody Epitopes of Ehrlichia chaffeensis Ankyrin Protein 200 and Tandem Repeat Protein 47 and Evaluation of Synthetic Immunodeterminants for Serodiagnosis of Human Monocytotropic Ehrlichiosis," Clinical and Vaccine Immunology, 17(1): 87-97 (2010).

McBride, J. W. et al., "Identification of a Glycosylated Ehrlichia canis 19-kilodalton major immunoreactive protein with a species-specific serine-rich glycopeptide epitope," Infection and Immunity, 75(1):74-82 (2007).

Nazari, M. et al., "Molecular Detection of Ehrlichia canis in Dogs in Malaysia," PLoS Negl. Trop. Dis., 7(1):e1982 (Jan. 2013).

Nilsson, J., et al., "Affinity fusion strategies for detection, purification, and immobilization of recombinant proteins." Protein Expr Purif. (1997); 11(1): 1-16.

Office Action for U.S. Appl. No. 12/950,707, dated Oct. 16, 2013, 7 pages.

Office Action for U.S. Appl. No. 14/252,690, dated Aug. 22, 2014, 20 pages.

Paddock, C. D. et al., "Ehrlichia chaffeensis: a prototypical emerging pathogen," Clin. Microbiol. Rev., 16(1):37-64 (2003).

Sirigireddy, K. R. et al., "Multiplex Detection of Ehrlichia and Anaplasma Species Pathogens in Peripheral Blood by Real-Time

(56) References Cited

OTHER PUBLICATIONS

Reverse Transcriptase-Polymerase Chain Reaction," Journal of Molecular Diagnostics, 7(2):308-316 (May 2005).
Search Report in Chinese Application No. 201510582480.1, with English translation, dated Aug. 10, 2016, 4 pages.
Search Report in Chinese Application No. 201580023440.1, with English translation, dated Jun. 26, 2017, 4 pages.
Supplementary European Search Report for European Application No. 13844762.8, dated Apr. 25, 2016, 9 pages.
Supplementary European Search Report for European Application No. 10832262.9, dated Jan. 21, 2014, 7 pages.
Thomas, R. J. et al., "Current management of human granulocytic anaplasmosis, human monocytic ehrlichiosis and Ehrlichia ewingii Ehrlichiosis," Expert Rev. Anti. Infect. Ther., 7(6):709-722 (Aug. 2009).
Zhang, C. et al., "Identification of 19 polymorphic major outer membrane protein genes and their immunogenic peptides in Ehrlichia ewingii for use in a serodiagnostic assay," Clinical and Vaccine Immunology, 15(3): 402-411 (2008).

* cited by examiner

PEPTIDES, DEVICES, AND METHODS FOR THE DETECTION OF EHRLICHIA ANTIBODIES

CROSS-REFERENCE TO RELATED APPLICATIONS

This application is a continuation of U.S. patent application Ser. No. 15/608,560, filed May 30, 2017, which is a continuation of U.S. patent application Ser. No. 14/842,440, filed Sep. 1, 2015 (now U.S. Pat. No. 9,696,300, issued Jul. 4, 2017), which is a divisional of U.S. application Ser. No. 14/252,690, filed Apr. 14, 2014 (now U.S. Pat. No. 9,157,913, issued Oct. 13, 2015), which is a continuation of U.S. patent application Ser. No. 14/052,296, filed Oct. 11, 2013 (now U.S. Pat. No. 9,651,546, issued May 16, 2017), which claims the benefit of priority of U.S. Provisional Application No. 61/712,578, filed Oct. 11, 2012, which are hereby incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ABAX_040_05_US_SeqList_ST25.txt, date recorded Aug. 22, 2019, file size 58 kilobytes).

BACKGROUND OF THE INVENTION

*Ehrlichia* bacteria are obligate intracellular pathogens that infect circulating lymphocytes in mammalian hosts. *Ehrlichia canis* and *Ehrlichia chaffeensis* are members of the same sub-genus group that infect canines and humans and cause canine monocytic ehrlichiosis (CME) and human monocytic ehrlichiosis (HME), respectively. Another species of *Ehrlichia* known as *Ehrlichia ewingii* has tropism for granulocytes and causes granulocytic ehrlichiosis. The canine disease is characterized by fever, epilepsy, incoordination, lethargy, bleeding episodes, lymphadenopathy, weight loss, and pancytopenia. In humans the disease is characterized by fever, headache, myalgia, and leukopenia. Early detection and treatment are important for treating both canine and human ehrlichiosis.

Indirect immunofluorescence assays (IFA) and enzyme-linked immunosorbent assays (ELISA) have typically been used in the diagnosis of these diseases. These assays measure or otherwise detect the binding of anti-*Ehrlichia* antibodies from a subject's blood, plasma, or serum to infected cells, cell lysates, or partially purified whole *Ehrlichia* proteins. However, currently known assays for detecting anti-*Ehrlichia* antibodies or fragments thereof are severely limited in usefulness because of sensitivity and specificity issues directly related to the impure nature of the *Ehrlichia* antigen(s) used in these tests. That is, the currently known assays use mixtures of many whole *Ehrlichia* antigens or antigens that are not species specific.

Accordingly, there remains a need in the art for additional assays for detecting *Ehrlichia* antigens and serodiagnosis of monocytic ehrlichiosis and granulocytic ehrlichiosis.

SUMMARY OF THE INVENTION

The present invention is based, in part, on the discovery that certain sequence variants in a fragment of the *Ehrlichia* Outer Membrane Protein 1 (OMP-1) proteins provide for robust detection of an antibody response against a range of *Ehrlichia* species. Accordingly, the invention provides compositions, devices, methods, and kits useful for the detection of antibodies that bind to *Ehrlichia* antigens and the diagnosis of monocytic and/or granulocytic ehrlichiosis.

In one aspect, the invention provides peptides capable of binding to antibodies that recognize *Ehrlichia* antigens. In certain embodiments, peptides of the invention comprise a sequence of S-$X_2$-K-E-D-K-Q-T-T-$X_{10}$-$X_{11}$-I-W-G-L-K-Q-$X_{18}$-W-$X_{20}$-G-$X_{22}$-P-$X_{24}$-$X_{25}$-$X_{26}$-$X_{27}$-$X_{28}$-$X_{29}$-$X_{30}$-$X_{31}$-$X_{32}$-$X_{33}$-$X_{34}$-$X_{35}$-$X_{36}$-$X_{37}$-$X_{38}$-$X_{39}$-C(SEQ ID NO: 1), or a fragment thereof, wherein $X_2$ is an amino acid selected from the group consisting of A and V, $X_{10}$ is an amino acid selected from the group consisting of T and V, $X_{11}$ is an amino acid selected from the group consisting of G and A, $X_{18}$ is an amino acid selected from the group consisting of E and Q, $X_{20}$ is an amino acid selected from the group consisting of D and N, $X_{22}$ is an amino acid selected from the group consisting of S and V, $X_{24}$ is an amino acid selected from the group consisting of A and I, $X_{25}$ is an amino acid selected from the group consisting of T and P, $X_{26}$ is an amino acid selected from the group consisting of S, N, and K, $X_{27}$ is any amino acid except H, N, S, or A, $X_{28}$ is any amino acid except A, S, or P, $X_{29}$ is any amino acid except D, P, N, or S, $X_{30}$ is any amino acid except A, E, D, or S, $X_{31}$ is any amino acid except D, N, V, or H, $X_{32}$ is any amino acid except F or T, $X_{33}$ is any amino acid except N, F or I, $X_{34}$ is any amino acid except N, T or D, $X_{35}$ is any amino acid except K, V or P, $X_{36}$ is any amino acid except G, P, or S, $X_{37}$ is any amino acid except Y, N, or T, $X_{38}$ is any amino acid except S, Y, or I, and $X_{39}$ is any amino acid except F or S.

In some embodiments, peptides of the invention comprise a sequence of S-$X_2$-K-E-D-K-Q-T-T-T-$X_{11}$-I-W-G-L-K-Q-$X_{18}$-W-D-G-$X_{22}$-P-$X_{24}$-$X_{25}$-$X_{26}$-$X_{27}$-$X_{25}$-$X_{29}$-$X_{30}$-$X_{31}$-$X_{32}$-$X_{33}$-$X_{34}$-$X_{35}$-$X_{36}$-$X_{37}$-$X_{38}$-$X_{39}$-C(SEQ ID NO: 83), or a fragment thereof, wherein $X_2$ is an amino acid selected from the group consisting of A and V, $X_{11}$ is an amino acid selected from the group consisting of G and A, $X_{18}$ is an amino acid selected from the group consisting of E and Q, $X_{22}$ is an amino acid selected from the group consisting of S and V, $X_{24}$ is an amino acid selected from the group consisting of A and I, $X_{25}$ is an amino acid selected from the group consisting of T and P, $X_{26}$ is an amino acid selected from the group consisting of S and N, $X_{27}$ is any amino acid except H, N, S, or A, $X_{28}$ is any amino acid except A, S, or P, $X_{29}$ is any amino acid except D, P, N, or S, $X_{30}$ is any amino acid except A, E, D, or S, $X_{31}$ is any amino acid except D, N, V, or R, $X_{32}$ is any amino acid except F or T, $X_{33}$ is any amino acid except N, F or I, $X_{34}$ is any amino acid except N, T or D, $X_{35}$ is any amino acid except K, V or P, $X_{36}$ is any amino acid except G, P, or S, $X_{37}$ is any amino acid except Y, N, or T, $X_{38}$ is any amino acid except S, Y, or I, and $X_{39}$ is any amino acid except F or S.

In other embodiments, peptides of the invention comprise a sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-$X_{41}$-T-R-$X_{44}$-T-F-G-$X_{48}$-$X_{49}$-K-Q-Y-D-G-A-$X_{56}$-I-$X_{58}$-E-N-Q-V-Q-N-K-F-T-I-S-N-C(SEQ ID NO: 3) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{41}$ is an amino acid selected from the group consisting of D and N, $X_{44}$ is any amino acid, $X_{48}$ is an amino acid selected from the group consisting of V and A, $X_{49}$ is any amino acid, $X_{56}$ is any amino acid, and $X_{58}$ is any amino acid.

In related embodiments, peptides of the invention comprise a sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-K-$X_{40}$-A-D-T-R-$X_{45}$-T-F-G-L-$X_{50}$-K-Q-T-D-G-A-$X_{57}$-I-$X_{59}$-E-N-Q-V-Q-N-K-F-T-I-S-N-C(SEQ ID NO: 85) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{40}$ is any amino acid, $X_{45}$ is any amino acid, $X_{50}$ is any amino acid, $X_{57}$ is any amino acid, and $X_{59}$ is any amino acid.

In still other embodiments, peptides of the invention comprise a sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-E-T-R-$X_{44}$-T-F-G-L-$X_{49}$-K-Q-Y-D-G-A-$X_{56}$-I-$X_{58}$-E-N-Q-V-Q-N-K-F-T-I-S-N-C(SEQ ID NO: 72) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{44}$ is any amino acid, $X_{49}$ is any amino acid, $X_{56}$ is any amino acid, and $X_{58}$ is any amino acid.

In certain embodiments, peptides of the invention comprise or consist of a sequence of SEQ ID NO: 3 or SEQ ID NO: 72, wherein $X_{39}$ is K. In other embodiments, peptides of the invention comprise or consist of a sequence of SEQ ID NO: 3 or SEQ ID NO: 72, wherein $X_{44}$ is an amino acid selected from the group consisting of K and R and $X_{49}$ is an amino acid selected from the group consisting of E and D. In still other embodiments, peptides of the invention comprise or consist of a sequence of SEQ ID NO: 3 or SEQ ID NO: 72, wherein $X_{56}$ is an amino acid selected from the group consisting of K and Q and $X_{58}$ is an amino acid selected from the group consisting of E and T.

In some embodiments, peptides of the invention comprise a fragment of SEQ ID NO: 1, SEQ ID NO: 3 or SEQ ID NO: 72. Such fragments may comprise at least 10, 15, 20, 25, 30, or 35 contiguous amino acids from SEQ ID NO: 1 or at least 10, 15, 20, 25, 30, 35, or 40 contiguous amino acids from SEQ ID NO: 3 or SEQ ID NO: 72. In certain embodiments, a peptide of the invention may comprise or consist of a sequence of SEQ ID NO: 5, SEQ ID NO: 6, SEQ ID NO: 71, SEQ ID NO: 84, or SEQ ID NO: 86.

In certain embodiments, peptides of the invention described herein may further comprise an additional N-terminal peptide sequence. The additional N-terminal peptide sequence can comprise 1, 2, 3, 4, 5, 6, 7, 8, 9, 10, or more amino acids and can be either a native or non-native sequence. In other embodiments, peptides of the invention described herein may further comprise an additional C-terminal sequence. The additional C-terminal peptide sequence can comprise 1, 2, 3, 4, 5, 6, 7, 8, 9, 10, or more amino acids and can be either a native or non-native sequence. In some embodiments, the non-native sequence comprises a non-OMP-1 *Ehrlichia* antigen (e.g., *Ehrlichia* p 38, p 43, p 120, p 140, p 153, p 156, p 200, gp19, gp36, gp47, gp200, or HGE-3).

In certain embodiments, peptides of the invention comprise at least 25, 30, 35, 40, 45, 50, or more amino acids. In certain embodiments, peptides of the invention are isolated (e.g., synthetic and/or purified) peptides. In certain embodiments, peptides of the invention are conjugated to a ligand. For example, in certain embodiments, the peptides are biotinylated. In other embodiments, the peptides are conjugated to streptavidin, avidin, or neutravidin. In other embodiments, the peptides are conjugated to a carrier protein (e.g., serum albumin, keyhole limpet hemocyanin (KLH), or an immunoglobulin Fc domain). In still other embodiments, the peptides are conjugated to a dendrimer and/or are part of a multiple antigenic peptides system (MAPS).

In certain embodiments, peptides of the invention are attached to or immobilized on a solid support. In one embodiment, the peptides of the invention are attached to a solid support through a metallic nanolayer. In certain embodiments, the solid support is a bead (e.g., a colloidal particle, metallic nanoparticle or nanoshell, latex bead, etc.), a flow path in a lateral flow immunoassay device (e.g., a porous membrane), a blot (Western blot, a slot blot, or dot blot), a flow path in an analytical or centrifugal rotor, or a tube or well (e.g., in a plate suitable for an ELISA assay).

In another aspect, the invention provides compositions comprising two or more peptides of the invention. For example, in certain embodiments, the composition comprises a mixture or population of two, three, four, or more different peptides of the invention, wherein each peptide comprises a sequence of SEQ ID NO: 1. In some embodiments, the composition comprises a mixture or population of two, three, four, or more different peptides of the invention, wherein each peptide comprises a sequence of SEQ ID NO: 3. In other embodiments, the composition comprises a mixture or population of two, three, four, or more different peptides of the invention, wherein each peptide comprises a sequence of SEQ ID NO: 72. In yet other embodiments, the composition comprises a mixture or population of two, three, four, or more different peptides of the invention, wherein each peptide comprises a sequence of SEQ ID NO: 7. In still other embodiments, the composition comprises a mixture or population of two, three, four, or more different peptides of the invention, wherein each peptide comprises a sequence of SEQ ID NO: 70. In some embodiments, the composition comprises a mixture or population of two, three, four, or more different peptides of the invention, wherein each peptide comprises a sequence of SEQ ID NO: 83. In other embodiments, the composition comprises a mixture or population of two, three, four, or more different peptides of the invention, wherein each peptide comprises a sequence of SEQ ID NO: 85. In certain embodiments, the composition comprises a mixture or population of two, three, four, or more different peptides of the invention, wherein each peptide comprises a sequence of SEQ ID NO: 1, SEQ ID NO: 3, SEQ ID NO: 5, SEQ ID NO: 72, SEQ ID NO: 83, SEQ ID NO: 84, SEQ ID NO: 85, SEQ ID NO: 86.

In another aspect, the invention provides nucleic acids comprising a sequence encoding a peptide of the invention. In addition, the invention provides vectors comprising such nucleic acids, and host cells comprising such vectors. In certain embodiments, the vector is a shuttle vector. In other embodiments, the vector is an expression vector (e.g., a bacterial or eukaryotic expression vector). In certain embodiments, the host cell is a bacterial cell. In other embodiments, the host cell is a eukaryotic cell.

In another aspect, the invention provides devices. In certain embodiments, the devices are useful for performing an immunoassay. For example, in certain embodiments, the device is a lateral flow immunoassay device. In other embodiments, the device is an analytical or centrifugal rotor. In other embodiments, the device is a tube or a well, e.g., in a plate suitable for an ELISA assay. In still other embodiments, the device is an electrochemical, optical, or opto-electronic sensor.

In certain embodiments, the device comprises a peptide of the invention. In other embodiments, the device comprises a mixture of different peptides of the invention. For example, in certain embodiments, the device comprises two, three, four, or more different peptides of the invention. In certain embodiments, the peptide or each peptide in the mixture comprises a sequence of SEQ ID NO: 1, SEQ ID NO: 3, SEQ ID NO: 5, SEQ ID NO: 7, SEQ ID NO: 70, SEQ ID NO: 72, SEQ ID NO: 83, SEQ ID NO: 84, SEQ ID NO: 85, or SEQ ID NO: 86. In certain embodiments, the peptides are attached to or immobilized upon the device.

In another aspect, the invention provides methods of detecting in a sample an antibody to an epitope of an *Ehrlichia* antigen. In certain embodiments, the methods comprise contacting a sample with a peptide of the invention, and detecting formation of an antibody-peptide complex comprising said peptide, wherein formation of said complex is indicative of the presence of an antibody to an epitope of a *Ehrlichia* antigen in said sample. In certain embodiments, the *Ehrlichia* antigen is from an infectious *Ehrlichia* species, such as *Ehrlichia canis, Ehrlichia chaffeensis, Ehrlichia ewingii*, or *Ehrlichia muris*. In certain embodiments, the methods comprise contacting the sample with a mixture or population of different peptides of the invention (i.e. a mixture of two, three, four, or more different peptides of the invention). In some embodiments, the methods provide for detection of antibodies to antigens from multiple *Ehrlichia* species (e.g., *Ehrlichia canis, Ehrlichia chaffeensis, Ehrlichia ewingii*, and *Ehrlichia muris*) in a sample simultaneously.

In certain embodiments, the peptide or each peptide in the mixture is an isolated (e.g., synthetic and/or purified) peptide. In certain embodiments, the peptide or mixture or population of peptides is attached to or immobilized upon a solid support. In one embodiment, the peptide or mixture or population of peptides is attached to the solid support through a metallic (e.g., gold) nanolayer. In certain embodiments, the solid support is a bead or plurality of beads (e.g., a colloidal particle, a metallic nanoparticle or nanoshell, a latex bead, etc.), a flow path in a lateral flow immunoassay device (e.g., a porous membrane), a flow path in an analytical or centrifugal rotor, a blot (Western blot, a slot blot, or dot blot), or a tube or a well (e.g., in a plate suitable for an ELISA assay). In certain embodiments, the solid support comprises metal, glass, a cellulose-based material (e.g., nitrocellulose), or a polymer (e.g., polystyrene, polyethylene, polypropylene, polyester, nylon, polysulfone, etc.). In certain embodiments, the peptide or mixture or population of different peptides is attached to a dendrimer and/or incorporated into a MAPS system. In certain other embodiments, the peptide or mixture or population of different peptides is attached to BSA.

In certain embodiments, the detecting step comprises performing an ELISA assay. In other embodiments, the detecting step comprises performing a lateral flow immunoassay. In other embodiments, the detecting step comprises performing an agglutination assay. In other embodiments, the detecting step comprises spinning the sample in an analytical or centrifugal rotor. In other embodiments, the detecting step comprises analyzing the sample using a Western blot, a slot blot, or a dot blot. In still other embodiments, the detecting step comprises analyzing the sample with an electrochemical sensor, an optical sensor, or an opto-electronic sensor. In certain embodiments, the detecting step comprises performing a wavelength shift assay.

In certain embodiments, the sample is a bodily fluid, such as blood, serum, plasma, cerebral spinal fluid, urine, mucus, or saliva. In other embodiments, the sample is a tissue (e.g., a tissue homogenate) or a cell lysate. In certain embodiments, the sample is from a wild animal (e.g., a deer or rodent, such as a mouse, chipmunk, squirrel, etc.). In other embodiments, the sample is from a lab animal (e.g., a mouse, rat, guinea pig, rabbit, monkey, primate, etc.). In other embodiments, the sample is from a domesticated or feral animal (e.g., a dog, a cat, a horse). In still other embodiments, the sample is from a human.

In another aspect, the invention provides methods of diagnosing monocytic and/or granulocytic ehrlichiosis in a subject. In certain embodiments, the methods comprise contacting a sample from the subject with a peptide of the invention, and detecting formation of an antibody-peptide complex comprising said peptide, wherein formation of said complex is indicative of the subject having monocytic and/or granulocytic ehrlichiosis. In certain embodiments, the methods comprise contacting the sample with a mixture or population of different peptides of the invention (i.e. a mixture of two, three, four, or more different peptides of the invention).

In yet another aspect, the invention provides kits. In certain embodiments, the kits comprise a peptide of the invention. In certain embodiments, the kits comprise two, three, four, or more different peptides of the invention. The peptides can comprise a sequence of SEQ ID NO: 1, SEQ ID NO: 3, SEQ ID NO: 5, SEQ ID NO: 7, SEQ ID NO: 70, SEQ ID NO: 72, SEQ ID NO: 83, SEQ ID NO: 84, SEQ ID NO: 85, or SEQ ID NO: 86. In certain embodiments, the peptides are attached to or immobilized on a solid support optionally through a metallic nanolayer. In certain embodiments, the solid support is a bead (e.g., a colloidal particle, a metallic nanoparticle or nanoshell, a latex bead, etc.), a flow path in a lateral flow immunoassay device, a flow path in an analytical or centrifugal rotor, or a tube or a well (e.g., in a plate). In certain embodiments, the peptide or peptides are attached to a dendrimer and/or incorporated into a MAPS system. In certain other embodiments, the peptide or mixture of different peptides is attached to BSA.

In certain embodiments, the kits further comprise a population of beads or a plate (e.g., a plate suitable for an ELISA assay). In other embodiments, the kits further comprise a device, such as a lateral flow immunoassay device, an analytical or centrifugal rotor, a Western blot, a dot blot, a slot blot, an electrochemical sensor, an optical sensor, or an opto-electronic sensor. In certain embodiments, the population of beads, the plate, or the device is useful for performing an immunoassay. For example, in certain embodiments, the population of beads, the plate, or the device is useful for detecting formation of an antibody-peptide complex comprising an antibody from a sample and a peptide of the invention. In certain embodiments, a peptide or a mixture of different peptides of the invention is attached to or immobilized on the beads, the plate, or the device.

In certain embodiments, the kits further comprise an instruction. For example, in certain embodiments, the kits comprise an instruction indicating how to use a peptide of the invention to detect an antibody to an *Ehrlichia* antigen or to diagnose monocytic and/or granulocytic ehrlichiosis. In certain embodiments, the kits comprise an instruction indicating how to use a population of beads, a plate, or a device (e.g., comprising a peptide or a mixture of different peptides of the invention) to detect an antibody to one or more *Ehrlichia* antigens or to diagnose monocytic and/or granulocytic ehrlichiosis.

Additional aspects and embodiments of the invention will be apparent from the detailed description that follows.

DETAILED DESCRIPTION

Figure 1:
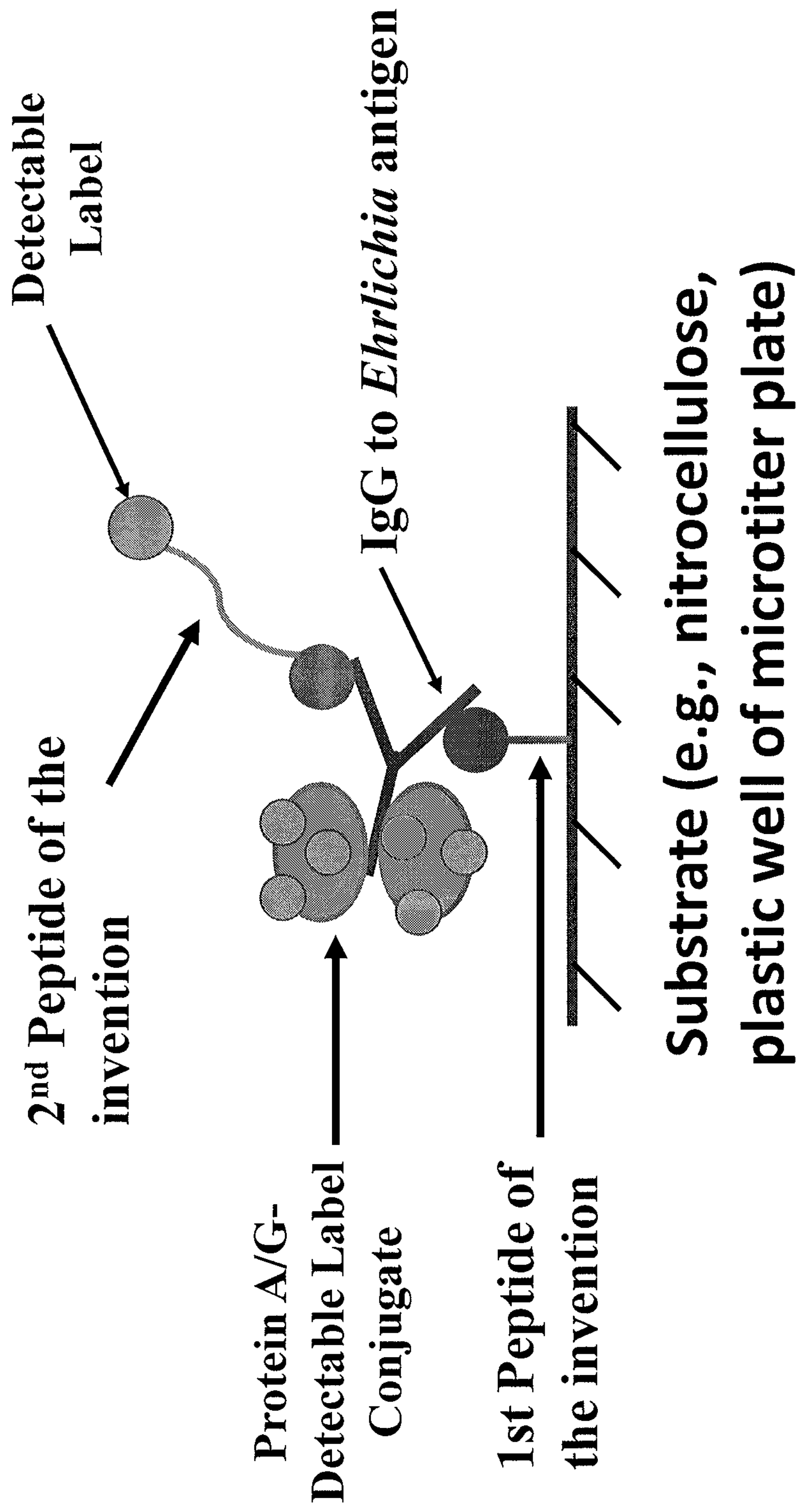
FIG. 1 is a diagram of a double antigen sandwich assay which can be used to detect antibodies to *Ehrlichia* antigens. In this embodiment, peptides of the invention are immobilized to a suitable substrate (e.g., nitrocellulose membrane, well of an ELISA plate) at a test site. Antibodies to *Ehrlichia* antigens in a test sample are bound by the immobilized peptides of the invention. Test sample antibodies to appropriate *Ehrlichia* antigens will then bind to a second set of peptides of the invention that are conjugated to a detectable label (e.g., metallic nanoparticle or nanoshell (e.g., colloidal gold), horse radish peroxidase (HRP), alkaline phosphatase (ALP), fluorophore, colored latex particle), which detects the presence of the antibodies bound to the first set of peptides immobilized at the test site. In certain embodiments, to amplify the detection signal, protein A and/or protein G molecules conjugated to a detectable label (e.g., metallic nanoparticle or nanoshell (e.g., colloidal gold), HRP, ALP, fluorophore, colored latex particle) may be applied to the test site where they will bind to the Fc region of any antibodies to *Ehrlichia* antigens captured by the immobilized peptides of the invention.

As used herein, the following terms shall have the following meanings:

The term "antigen," as used herein, refers to a molecule capable of being recognized by an antibody. An antigen can be, for example, a peptide or a modified form thereof. An antigen can comprise one or more epitopes.

The term "epitope," as used herein, is a portion of an antigen that is specifically recognized by an antibody. An epitope, for example, can comprise or consist of a portion of a peptide (e.g., a peptide of the invention). An epitope can be a linear epitope, sequential epitope, or a conformational epitope. In certain embodiments, epitopes may comprise non-contiguous regions.

The term "OMP-1 protein" refers to any of the Outer Membrane Protein 1 paralogs of *Ehrlichia*, including, but not limited to, *E. canis* P-30, *E. canis* P30-1, *E. chaffeensis* P28, *E. chaffeensis* OMP-1C, *E. chaffeensis* OMP-1D, *E. chaffeensis* OMP-1E, and *E. chaffeensis* OMP-1F.

The terms "nucleic acid," "oligonucleotide" and "polynucleotide" are used interchangeably herein and encompass DNA, RNA, cDNA, whether single stranded or double stranded, as well as chemical modifications thereof.

Single letter amino acid abbreviations used herein have their standard meaning in the art, and all peptide sequences described herein are written according to convention, with the N-terminal end to the left and the C-terminal end to the right.

Additional terms shall be defined, as required, in the detailed description that follows.

Compositions and Devices

The present invention is based, in part, on the discovery that certain sequence variants in a fragment of the *Ehrlichia* OMP-1 proteins provide for robust detection of an antibody response against a range of *Ehrlichia* species, including *E. canis, E. chaffeensis, E. ewingii*, and *E. muris*. Accordingly, in one aspect, the invention provides peptides capable of binding to antibodies that recognize *Ehrlichia* antigens.

In certain embodiments, peptides of the invention comprise a sequence of S-$X_2$-K-E-D-K-Q-T-T-$X_{10}$-$X_{11}$-I-W-G-L-K-Q-$X_{18}$-W-$X_{20}$-G-$X_{22}$-P-$X_{24}$-$X_{25}$-$X_{26}$-$X_{27}$-$X_{28}$-$X_{29}$-$X_{30}$-$X_{31}$-$X_{32}$-$X_{33}$-$X_{34}$-$X_{35}$-$X_{36}$-$X_{37}$-$X_{38}$-$X_{39}$-C(SEQ ID NO: 1), or a fragment thereof, wherein SEQ ID NO: 1, as used throughout the specification unless further specified, has the following characteristics: $X_2$ is an amino acid selected from the group consisting of A and V; $X_{10}$ is an amino acid selected from the group consisting of T and V; $X_{11}$ is an amino acid selected from the group consisting of G and A; $X_{18}$ is an amino acid selected from the group consisting of E and Q; $X_{20}$ is an amino acid selected from the group consisting of D and N; $X_{22}$ is an amino acid selected from the group consisting of S and V; $X_{24}$ is an amino acid selected from the group consisting of A and I; $X_{25}$ is an amino acid selected from the group consisting of T and P; $X_{26}$ is an amino acid selected from the group consisting of S, N, and K; $X_{27}$ is any amino acid except H, N, S, or A; $X_{28}$ is any amino acid except A, S, or P; $X_{29}$ is any amino acid except D, P, N, or S; $X_{30}$ is any amino acid except A, E, D, or S; $X_{31}$ is any amino acid except D, N, V, or H; $X_{32}$ is any amino acid except F or T; $X_{33}$ is any amino acid except N, F or I; $X_{34}$ is any amino acid except N, T or D; $X_{35}$ is any amino acid except K, V or P; $X_{36}$ is any amino acid except G, P, or S; $X_{37}$ is any amino acid except Y, N, or T; $X_{38}$ is any amino acid except S, Y, or I; and $X_{39}$ is any amino acid except F or S.

In certain embodiments, peptides of the invention comprise a sequence of SEQ ID NO: 1, wherein $X_2$ is V and $X_{10}$ is T. In some embodiments, peptides of the invention comprise a sequence of SEQ ID NO: 1, wherein $X_{10}$ is T and $X_{26}$ is selected from the group consisting of S and N. In other embodiments, peptides of the invention comprise a sequence of SEQ ID NO: 1, wherein $X_{24}$ is A, $X_{25}$ is selected from the group consisting of T and P, and $X_{26}$ is selected from the group consisting of S and N. In still other embodiments, peptides of the invention comprise a sequence of SEQ ID NO: 1, wherein $X_{26}$ is selected from the group consisting of S and N and $X_{31}$ is any amino acid except D, N, V, R, or H. In certain embodiments, peptides of the invention comprise a sequence of SEQ ID NO: 1, wherein $X_{27}$-$X_{39}$ has a sequence selected from the group consisting of Q-R-K-N-E-P-S-E-T-N-P-G-Q (SEQ ID NO: 74), M-V-E-F-E-E-L-Q-R-N-W-H-P (SEQ ID NO: 75), M-L-E-V-S-W-L-I-D-F-M-A-P (SEQ ID NO: 76), and Q-D-E-N-L-Y-S-S-I-F-F-V-P (SEQ ID NO: 77).

In related embodiments, peptides of the invention comprise a sequence of S-$X_2$-K-E-D-K-Q-T-T-T-$X_{11}$-I-W-G-L-K-Q-$X_{18}$-W-D-G-$X_{22}$-P-$X_{24}$-$X_{25}$-$X_{26}$-$X_{27}$-$X_{25}$-$X_{29}$-$X_{30}$-$X_{31}$-$X_{32}$-$X_{33}$-$X_{34}$-$X_{35}$-$X_{36}$-$X_{37}$-$X_{38}$-$X_{39}$-C(SEQ ID NO: 83), or a fragment thereof, wherein $X_2$ is an amino acid selected from the group consisting of A and V, $X_{11}$ is an amino acid selected from the group consisting of G and A, $X_{18}$ is an amino acid selected from the group consisting of E and Q, $X_{22}$ is an amino acid selected from the group consisting of S and V, $X_{24}$ is an amino acid selected from the group consisting of A and I, $X_{25}$ is an amino acid selected from the group consisting of T and P, $X_{26}$ is an amino acid selected from the group consisting of S and N, $X_{27}$ is any amino acid except H, N, S, or A, $X_{28}$ is any amino acid except A, S, or P, $X_{29}$ is any amino acid except D, P, N, or S, $X_{30}$ is any amino acid except A, E, D, or S, $X_{31}$ is any amino acid except D, N, V, or R, $X_{32}$ is any amino acid except F or T, $X_{33}$ is any amino acid except N, F or I, $X_{34}$ is any amino acid except N, T or D, $X_{35}$ is any amino acid except K, V or P, $X_{36}$ is any amino acid except G, P, or S, $X_{37}$ is any amino acid except Y, N, or T, $X_{38}$ is any amino acid except S, Y, or I, and $X_{39}$ is any amino acid except F or S. In some embodiments, peptides of the invention comprise a sequence of SEQ ID NO: 83, wherein $X_{27}$-$X_{39}$ has a sequence selected from the group consisting of Q-R-K-N-E-P-S-E-T-N-P-G-Q (SEQ ID NO: 74), M-V-E-F-E-E-L-Q-R-N-W-H-P (SEQ ID NO: 75), M-L-E-V-S-W-L-I-D-F-M-A-P (SEQ ID NO: 76), and Q-D-E-N-L-Y-S-S-I-F-F-V-P (SEQ ID NO: 77).

In certain other embodiments of the invention, peptides of the invention comprise a sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-$X_{41}$-T-R-$X_{44}$-T-F-G-$X_{48}$-$X_{49}$-K-Q-Y-D-G-A-$X_{56}$-I-$X_{58}$-E-N-Q-V-Q-N-K-F-T-I-S-N-C(SEQ ID NO: 3) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{41}$ is an amino acid selected from the group consisting of D and N, $X_{44}$ is any amino acid, $X_{48}$ is an amino acid selected from the group consisting of V and A, $X_{49}$ is any amino acid, $X_{56}$ is any amino acid, and $X_{58}$ is any amino acid.

In still other embodiments, peptides of the invention comprise a sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-

G-G-G-G-N-F-S-A-K-E-E-K-$X_{40}$-A-D-T-R-$X_{45}$-T-F-G-L-$X_{50}$-K-Q-T-D-G-A-$X_7$-I-$X_{59}$-E-N-Q-V-Q-N-K-F-T-I-S-N-C(SEQ ID NO: 85) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{40}$ is any amino acid, $X_{45}$ is any amino acid, $X_{50}$ is any amino acid, $X_{57}$ is any amino acid, and $X_{59}$ is any amino acid.

In particular embodiments, peptides of the invention comprise a sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-E-T-R-$X_{44}$-T-F-G-L-$X_{49}$-K-Q-Y-D-G-A-$X_{56}$-I-$X_{58}$-E-N-Q-V-Q-N-K-F-T-I-S-N-C(SEQ ID NO: 72) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{44}$ is any amino acid, $X_{49}$ is any amino acid, $X_{56}$ is any amino acid, and $X_{58}$ is any amino acid. In one particular embodiment, peptides comprising a sequence of SEQ ID NO: 72 enable the detection of antibodies to *Ehrlichia* antigens from multiple species (e.g., *E. canis, E. chaffeensis, E. ewingii*, and *E. muris*) simultaneously.

In some embodiments, peptides of the invention comprise or consist of a sequence of SEQ ID NO: 3 or SEQ ID NO: 72, wherein $X_{39}$ is K. In other embodiments, peptides of the invention comprise or consist of a sequence of SEQ ID NO: 3 or SEQ ID NO: 72, wherein $X_{44}$ is an amino acid selected from the group consisting of K and R and $X_{49}$ is an amino acid selected from the group consisting of E and D. In still other embodiments, peptides of the invention comprise or consist of a sequence of SEQ ID NO: 3 or SEQ ID NO: 72, wherein $X_{56}$ is an amino acid selected from the group consisting of K and Q and $X_{58}$ is an amino acid selected from the group consisting of E and T.

In another aspect of the invention, peptides of the invention comprise or consist of a sequence of S-V-K-$X_4$-D-K-Q-$X_8$-T-$X_{10}$-V-L-W-G-I-R-Q-N-W-$X_{20}$-G-$X_{22}$-$X_{23}$-A-$X_{25}$-$X_{26}$-Q-V-E-V-E-W-Q-Q-R-G-W-G-G-C(SEQ ID NO: 7), wherein $X_4$ is an amino acid selected from the group consisting of E and N, $X_8$ is an amino acid selected from the group consisting of P and S, $X_{10}$ is an amino acid selected from the group consisting of A and S, $X_{20}$ is an amino acid selected from the group consisting of E and Q, $X_{22}$ is an amino acid selected from the group consisting of P and T, $X_{23}$ is an amino acid selected from the group consisting of S and V, $X_{25}$ is an amino acid selected from the group consisting of T and P, and $X_{26}$ is an amino acid selected from the group consisting of S and N.

In certain embodiments, a peptide of the invention comprises or consists of the sequence S-V-K-E-D-K-Q-P-T-A-V-L-W-G-I-R-Q-N-W-Q-G-P-S-A-T-S-Q-V-E-V-E-W-Q-Q-R-G-W-G-G-C(SEQ ID NO: 8); S-V-K-E-D-K-Q-S-T-A-V-L-W-G-I-R-Q-N-W-Q-G-P-S-A-T-S-Q-V-E-V-E-W-Q-Q-R-G-W-G-G-C(SEQ ID NO: 9); S-V-K-E-D-K-Q-P-T-S-V-L-W-G-I-R-Q-N-W-Q-G-P-S-A-T-S-Q-V-E-V-E-W-Q-Q-R-G-W-G-G-C(SEQ ID NO: 10); S-V-K-E-D-K-Q-P-T-A-V-L-W-G-I-R-Q-N-W-E-G-P-S-A-T-S-Q-V-E-V-E-W-Q-Q-R-G-W-G-G-C(SEQ ID NO: 11); S-V-K-E-D-K-Q-P-T-A-V-L-W-G-I-R-Q-N-W-Q-G-T-S-A-T-S-Q-V-E-V-E-W-Q-Q-R-G-W-G-G-C(SEQ ID NO: 12); S-V-K-E-D-K-Q-P-T-A-V-L-W-G-I-R-Q-N-W-Q-G-P-V-A-T-S-Q-V-E-V-E-W-Q-Q-R-G-W-G-G-C(SEQ ID NO: 13); S-V-K-E-D-K-Q-P-T-A-V-L-W-G-I-R-Q-N-W-Q-G-P-S-A-P-S-Q-V-E-V-E-W-Q-Q-R-G-W-G-G-C(SEQ ID NO: 14); S-V-K-E-D-K-Q-P-T-A-V-L-W-G-I-R-Q-N-W-Q-G-P-S-A-T-N-Q-V-E-V-E-W-Q-Q-R-G-W-G-G-C (SEQ ID NO: 15); S-V-K-E-D-K-Q-S-T-S-V-L-W-G-I-R-Q-N-W-Q-G-P-S-A-T-S-Q-V-E-V-E-W-Q-Q-R-G-W-G-G-C(SEQ ID NO: 16); S-V-K-E-D-K-Q-S-T-A-V-L-W-G-I-R-Q-N-W-E-G-P-S-A-T-S-Q-V-E-V-E-W-Q-Q-R-G-W-G-G-C(SEQ ID NO: 17); S-V-K-E-D-K-Q-S-T-A-V-L-W-G-I-R-Q-N-W-Q-G-T-S-A-T-S-Q-V-E-V-E-W-Q-Q-R-G-W-G-G-C(SEQ ID NO: 18); S-V-K-E-D-K-Q-S-T-A-V-L-W-G-I-R-Q-N-W-Q-G-P-V-A-T-S-Q-V-E-V-E-W-Q-Q-R-G-W-G-G-C(SEQ ID NO: 19); S-V-K-E-D-K-Q-S-T-A-V-L-W-G-I-R-Q-N-W-Q-G-P-S-A-P-S-Q-V-E-V-E-W-Q-Q-R-G-W-G-G-C(SEQ ID NO: 20); S-V-K-E-D-K-Q-S-T-A-V-L-W-G-I-R-Q-N-W-Q-G-P-S-A-P-N-Q-V-E-V-E-W-Q-Q-R-G-W-G-G-C(SEQ ID NO: 21); S-V-K-E-D-K-Q-P-T-S-V-L-W-G-I-R-Q-N-W-E-G-P-S-A-T-S-Q-V-E-V-E-W-Q-Q-R-G-W-G-G-C(SEQ ID NO: 22); S-V-K-E-D-K-Q-P-T-S-V-L-W-G-I-R-Q-N-W-Q-G-T-S-A-T-S-Q-V-E-V-E-W-Q-Q-R-G-W-G-G-C(SEQ ID NO: 23); S-V-K-E-D-K-Q-P-T-S-V-L-W-G-I-R-Q-N-W-Q-G-P-V-A-T-S-Q-V-E-V-E-W-Q-Q-R-G-W-G-G-C(SEQ ID NO: 24); S-V-K-E-D-K-Q-P-T-S-V-L-W-G-I-R-Q-N-W-Q-G-P-S-A-P-S-Q-V-E-V-E-W-Q-Q-R-G-W-G-G-C(SEQ ID NO: 25); S-V-K-E-D-K-Q-P-T-S-V-L-W-G-I-R-Q-N-W-Q-G-P-S-A-T-N-Q-V-E-V-E-W-Q-Q-R-G-W-G-G-C(SEQ ID NO: 26); S-V-K-E-D-K-Q-P-T-A-V-L-W-G-I-R-Q-N-W-E-G-T-S-A-T-S-Q-V-E-V-E-W-Q-Q-R-G-W-G-G-C(SEQ ID NO: 27); S-V-K-E-D-K-Q-P-T-A-V-L-W-G-I-R-Q-N-W-E-G-P-V-A-T-S-Q-V-E-V-E-W-Q-Q-R-G-W-G-G-C(SEQ ID NO: 28); S-V-K-E-D-K-Q-P-T-A-V-L-W-G-I-R-Q-N-W-E-G-P-S-A-P-S-Q-V-E-V-E-W-Q-Q-R-G-W-G-G-C(SEQ ID NO: 29); S-V-K-E-D-K-Q-P-T-A-V-L-W-G-I-R-Q-N-W-E-G-P-S-A-T-N-Q-V-E-V-E-W-Q-Q-R-G-W-G-G-C (SEQ ID NO: 30); S-V-K-E-D-K-Q-P-T-A-V-L-W-G-I-R-Q-N-W-Q-G-T-V-A-T-S-Q-V-E-V-E-W-Q-Q-R-G-W-G-G-C(SEQ ID NO: 31); S-V-K-E-D-K-Q-P-T-A-V-L-W-G-I-R-Q-N-W-Q-G-T-S-A-P-S-Q-V-E-V-E-W-Q-Q-R-G-W-G-G-C(SEQ ID NO: 32); S-V-K-E-D-K-Q-P-T-A-V-L-W-G-I-R-Q-N-W-Q-G-T-S-A-T-N-Q-V-E-V-E-W-Q-Q-R-G-W-G-G-C(SEQ ID NO: 33); S-V-K-E-D-K-Q-P-T-A-V-L-W-G-I-R-Q-N-W-E-G-T-S-A-T-N-Q-V-E-V-E-W-Q-Q-R-G-W-G-G-C(SEQ ID NO: 34); S-V-K-E-D-K-Q-P-T-A-V-L-W-G-I-R-Q-N-W-Q-G-P-V-A-T-S-Q-V-E-

V-E-W-Q-Q-R-G-W-G-G-C(SEQ ID NO: 35); S-V-K-E-D-K-Q-P-T-A-V-L-W-G-I-R-Q-N-W-Q-G-P-V-A-P-S-Q-V-E-V-E-W-Q-Q-R-G-W-G-G-C(SEQ ID NO: 36); S-V-K-E-D-K-Q-P-T-A-V-L-W-G-I-R-Q-N-W-Q-G-P-V-A-T-N-Q-V-E-V-E-W-Q-Q-R-G-W-G-G-C (SEQ ID NO: 37); or S-V-K-E-D-K-Q-P-T-A-V-L-W-G-I-R-Q-N-W-E-G-P-V-A-P-N-Q-V-E-V-E-W-Q-Q-R-G-W-G-G-C(SEQ ID NO: 38).

In other embodiments, a peptide of the invention comprises or consists of the sequence S-V-K-N-D-K-Q-P-T-A-V-L-W-G-I-R-Q-N-W-Q-G-P-S-A-T-S-Q-V-E-V-E-W-Q-Q-R-G-W-G-G-C(SEQ ID NO: 39); S-V-K-N-D-K-Q-S-T-A-V-L-W-G-I-R-Q-N-W-Q-G-P-S-A-T-S-Q-V-E-V-E-W-Q-Q-R-G-W-G-G-C(SEQ ID NO: 40); S-V-K-N-D-K-Q-P-T-S-V-L-W-G-I-R-Q-N-W-Q-G-P-S-A-T-S-Q-V-E-V-E-W-Q-Q-R-G-W-G-G-C(SEQ ID NO: 41); S-V-K-N-D-K-Q-P-T-A-V-L-W-G-I-R-Q-N-W-E-G-P-S-A-T-S-Q-V-E-V-E-W-Q-Q-R-G-W-G-G-C (SEQ ID NO: 42); S-V-K-N-D-K-Q-P-T-A-V-L-W-G-I-R-Q-N-W-Q-G-T-S-A-T-S-Q-V-E-V-E-W-Q-Q-R-G-W-G-G-C(SEQ ID NO: 43); S-V-K-N-D-K-Q-P-T-A-V-L-W-G-I-R-Q-N-W-Q-G-P-V-A-T-S-Q-V-E-V-E-W-Q-Q-R-G-W-G-G-C(SEQ ID NO: 44); S-V-K-N-D-K-Q-P-T-A-V-L-W-G-I-R-Q-N-W-Q-G-P-S-A-P-S-Q-V-E-V-E-W-Q-Q-R-G-W-G-G-C(SEQ ID NO: 45); S-V-K-N-D-K-Q-P-T-A-V-L-W-G-I-R-Q-N-W-Q-G-P-S-A-T-N-Q-V-E-V-E-W-Q-Q-R-G-W-G-G-C(SEQ ID NO: 46); S-V-K-N-D-K-Q-S-T-S-V-L-W-G-I-R-Q-N-W-Q-G-P-S-A-T-S-Q-V-E-V-E-W-Q-Q-R-G-W-G-G-C(SEQ ID NO: 47); S-V-K-N-D-K-Q-S-T-A-V-L-W-G-I-R-Q-N-W-E-G-P-S-A-T-S-Q-V-E-V-E-W-Q-Q-R-G-W-G-G-C(SEQ ID NO: 48); S-V-K-N-D-K-Q-S-T-A-V-L-W-G-I-R-Q-N-W-Q-G-T-S-A-T-S-Q-V-E-V-E-W-Q-Q-R-G-W-G-G-C(SEQ ID NO: 49); S-V-K-N-D-K-Q-S-T-A-V-L-W-G-I-R-Q-N-W-Q-G-P-V-A-T-S-Q-V-E-V-E-W-Q-Q-R-G-W-G-G-C(SEQ ID NO: 50); S-V-K-N-D-K-Q-S-T-A-V-L-W-G-I-R-Q-N-W-Q-G-P-S-A-P-S-Q-V-E-V-E-W-Q-Q-R-G-W-G-G-C(SEQ ID NO: 51); S-V-K-N-D-K-Q-S-T-A-V-L-W-G-I-R-Q-N-W-Q-G-P-S-A-P-N-Q-V-E-V-E-W-Q-Q-R-G-W-G-G-C(SEQ ID NO: 52); S-V-K-N-D-K-Q-P-T-S-V-L-W-G-I-R-Q-N-W-E-G-P-S-A-T-S-Q-V-E-V-E-W-Q-Q-R-G-W-G-G-C(SEQ ID NO: 53); S-V-K-N-D-K-Q-P-T-S-V-L-W-G-I-R-Q-N-W-Q-G-T-S-A-T-S-Q-V-E-V-E-W-Q-Q-R-G-W-G-G-C(SEQ ID NO: 54); S-V-K-N-D-K-Q-P-T-S-V-L-W-G-I-R-Q-N-W-Q-G-P-V-A-T-S-Q-V-E-V-E-W-Q-Q-R-G-W-G-G-C(SEQ ID NO: 55); S-V-K-N-D-K-Q-P-T-S-V-L-W-G-I-R-Q-N-W-Q-G-P-S-A-P-S-Q-V-E-V-E-W-Q-Q-R-G-W-G-G-C(SEQ ID NO: 56); S-V-K-N-D-K-Q-P-T-S-V-L-W-G-I-R-Q-N-W-Q-G-P-S-A-T-N-Q-V-E-V-E-W-Q-Q-R-G-W-G-G-C (SEQ ID NO: 57); S-V-K-N-D-K-Q-P-T-A-V-L-W-G-I-R-Q-N-W-E-G-T-S-A-T-S-Q-V-E-V-E-W-Q-Q-R-G-W-G-G-C(SEQ ID NO: 58); S-V-K-N-D-K-Q-P-T-A-V-L-W-G-I-R-Q-N-W-E-G-P-V-A-T-S-Q-V-E-V-E-W-Q-Q-R-G-W-G-G-C(SEQ ID NO: 59); S-V-K-N-D-K-Q-P-T-A-V-L-W-G-I-R-Q-N-W-E-G-P-S-A-P-S-Q-V-E-V-E-W-Q-Q-R-G-W-G-G-C(SEQ ID NO: 60); S-V-K-N-D-K-Q-P-T-A-V-L-W-G-I-R-Q-N-W-E-G-P-S-A-T-N-Q-V-E-V-E-W-Q-Q-R-G-W-G-G-C(SEQ ID NO: 61); S-V-K-N-D-K-Q-P-T-A-V-L-W-G-I-R-Q-N-W-Q-G-T-V-A-T-S-Q-V-E-V-E-W-Q-Q-R-G-W-G-G-C(SEQ ID NO: 62); S-V-K-N-D-K-Q-P-T-A-V-L-W-G-I-R-Q-N-W-Q-G-T-S-A-P-S-Q-V-E-V-E-W-Q-Q-R-G-W-G-G-C(SEQ ID NO: 63); S-V-K-N-D-K-Q-P-T-A-V-L-W-G-I-R-Q-N-W-Q-G-T-S-A-T-N-Q-V-E-V-E-W-Q-Q-R-G-W-G-G-C(SEQ ID NO: 64); S-V-K-N-D-K-Q-P-T-A-V-L-W-G-I-R-Q-N-W-E-G-T-S-A-T-N-Q-V-E-V-E-W-Q-Q-R-G-W-G-G-C(SEQ ID NO: 65); S-V-K-N-D-K-Q-P-T-A-V-L-W-G-I-R-Q-N-W-Q-G-P-V-A-T-S-Q-V-E-V-E-W-Q-Q-R-G-W-G-G-C(SEQ ID NO: 66); S-V-K-N-D-K-Q-P-T-A-V-L-W-G-I-R-Q-N-W-Q-G-P-V-A-P-S-Q-V-E-V-E-W-Q-Q-R-G-W-G-G-C(SEQ ID NO: 67); S-V-K-N-D-K-Q-P-T-A-V-L-W-G-I-R-Q-N-W-Q-G-P-V-A-T-N-Q-V-E-V-E-W-Q-Q-R-G-W-G-G-C(SEQ ID NO: 68); or S-V-K-N-D-K-Q-P-T-A-V-L-W-G-I-R-Q-N-W-E-G-P-V-A-P-N-Q-V-E-V-E-W-Q-Q-R-G-W-G-G-C(SEQ ID NO: 69).

In one particular embodiment of the invention, peptides of the invention comprise or consist of a sequence of S-$X_2$-K-D-$X_5$-K-Q-$X_8$-T-$X_{10}$-$X_{11}$-$X_{12}$-$X_{13}$-G-L-$X_{16}$-Q-$X_{18}$-$X_{19}$-$X_{20}$-G-$X_{22}$-$X_{23}$-$X_{24}$-$X_{25}$-$X_{26}$-$X_{27}$-$X_{28}$-$X_{29}$-$X_{30}$-$X_{31}$-$X_{32}$-$X_{33}$-$X_{34}$-$X_{35}$-$X_{36}$-$X_{37}$-$X_{38}$-$X_{39}$-C(SEQ ID NO: 70), wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of S, V, and A, $X_{11}$ is an amino acid selected from the group consisting of G and A, $X_{12}$ is an amino acid selected from the group consisting of L and V, $X_{13}$ is an amino acid selected from the group consisting of Y, F, and W, $X_{16}$ is an amino acid selected from the group consisting of K and R, $X_{18}$ is an amino acid selected from the group consisting of D and N, $X_{19}$ is an amino acid selected from the group consisting of W and F, $X_{20}$ is an amino acid selected from the group consisting of D and N, $X_{22}$ is an amino acid selected from the group consisting of T and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, and each of $X_{27}$-$X_{39}$ is any amino acid. In certain embodiments, $X_{27}$-$X_{39}$ has a sequence selected from the group consisting of Q-R-K-N-E-P-S-E-T-N-P-G-Q (SEQ ID NO: 74), M-V-E-F-E-E-L-Q-R-N-W-H-P (SEQ ID NO: 75), M-L-E-V-S-W-L-I-D-F-M-A-P (SEQ ID NO: 76), Q-D-E-N-L-Y-S-S-I-F-F-V-P (SEQ ID NO: 77), Q-R-K-N-D-P-S-E-T-S-P-G-Q (SEQ ID NO: 78), M-A-P-F-H-E-L-D-V-N-N-H-P (SEQ ID NO: 79), S-L-N-V-S-F-L-I-D-P-M-A-P (SEQ ID NO: 80), and Q-D-S-N-L-Y-S-S-I-F-F-V-P (SEQ ID NO: 81).

In certain embodiments, peptides of the invention comprise a sequence of SEQ ID NO: 1, SEQ ID NO: 3, SEQ ID NO: 7, SEQ ID NO: 70, SEQ ID NO: 72, SEQ ID NO: 83, or SEQ ID NO: 85 and an additional N-terminal peptide sequence (e.g., an N-terminal extension). The additional N-terminal peptide sequence can comprise 1, 2, 3, 4, 5, 6, 7, 8, 9, 10, 11, 12, 13, 14, 15, 20, 25, or more amino acids. In certain embodiments, the N-terminal peptide sequence has a length of about 5 to about 10, about 10 to about 15, about 15 to about 20, about 20 to about 25, about 25 to about 30, about 30 to about 40, or about 40 to about 50 amino acids. In one embodiment, the N-terminal peptide sequence can be one or more linking residues (e.g. one or more glycine, cysteine, or serine residues). For instance, in certain embodiments, the carboxyl-terminal cysteine residue in any of the sequences described herein can be located at the amino terminus instead. Accordingly, in some embodiments, peptides of the invention comprise or consist of a sequence of C-S-$X_3$-K-E-D-K-Q-T-T-$X_{11}$-$X_{12}$-I-W-G-L-K-Q-$X_{19}$-W-$X_{21}$-G-$X_{23}$-P-$X_{25}$-$X_{26}$-$X_{27}$-$X_{28}$-$X_{29}$-$X_{30}$-$X_{31}$-$X_{32}$-$X_{33}$-$X_{34}$-$X_{35}$-$X_{36}$-$X_{37}$-$X_{38}$-$X_{39}$-$X_{40}$ (SEQ ID NO: 2), wherein $X_3$ is an amino acid selected from the group consisting of A and V, $X_{11}$ is an amino acid selected from the group consisting of T and V, $X_{12}$ is an amino acid selected from the group consisting of G and A, $X_{19}$ is an amino acid selected from the group consisting of E and Q, $X_{21}$ is an amino acid selected from the group consisting of D and N, $X_{23}$ is an amino acid selected from the group consisting of S and V, $X_{25}$ is an amino acid selected from the group consisting of A and I, $X_{26}$ is an amino acid selected from the group consisting of T and P, $X_{27}$ is an amino acid selected from the group consisting of S, N, and K, $X_{28}$ is any amino acid except H, N, S, or A, $X_{29}$ is any amino acid except A, S, or P, $X_{30}$ is any amino acid except D, P, N, or S, $X_{31}$ is any amino acid except A, E, D, or S, $X_{32}$ is any amino acid except D, N, V, or H, $X_{33}$ is any amino acid except F or T, $X_{34}$ is any amino acid except N, F or I, $X_{35}$ is any amino acid except N, T or D, $X_{36}$ is any amino acid except K, V or P, $X_{37}$ is any amino acid except G, P, or S, $X_{38}$ is any amino acid except Y, N, or T, $X_{39}$ is any amino acid except S, Y, or I, and $X_{40}$ is any amino acid except F or S. In still other embodiments, peptides of the invention comprise or consist of a sequence of C-S-$X_3$-K-E-$X_6$-K-Q-$X_9$-T-$X_{11}$-$X_{12}$-$X_{13}$-$X_{14}$-G-L-K-Q-$X_{19}$-W-$X_{21}$-G-$X_{23}$-$X_{24}$-$X_{25}$-$X_{26}$-$X_{27}$-G-G-G-G-N-F-S-A-K-E-E-$X_{40}$-A-$X_{42}$-T-R-$X_{45}$-T-F-G-$X_{49}$-$X_{50}$-K-Q-Y-D-G-A-$X_{57}$-I-$X_{59}$-E-N-Q-V-Q-N-K-F-T-I-S-N(SEQ ID NO: 4), wherein $X_3$ is an amino acid selected from the group consisting of A and V, $X_6$ is an amino acid selected from the group consisting of E and D, $X_9$ is an amino acid selected from the group consisting of T and P, $X_{11}$ is an amino acid selected from the group consisting of T and V, $X_{12}$ is an amino acid selected from the group consisting of G and A, $X_{13}$ is an amino acid selected from the group consisting of L and V, $X_{14}$ is an amino acid selected from the group consisting of Y and F, $X_{19}$ is an amino acid selected from the group consisting of D and N, $X_{21}$ is an amino acid selected from the group consisting of D and N, $X_{23}$ is an amino acid selected from the group consisting of S and V, $X_{24}$ is an amino acid selected from the group consisting of A, S, and T, $X_{25}$ is an amino acid selected from the group consisting of A and I, $X_{26}$ is an amino acid selected from the group consisting of T and P, $X_{27}$ is an amino acid selected from the group consisting of S, N, and K, $X_{40}$ is any amino acid, $X_{42}$ is an amino acid selected from the group consisting of D and N, $X_{45}$ is any amino acid, $X_{49}$ is an amino acid selected from the group consisting of V and A, $X_{50}$ is any amino acid, $X_{57}$ is any amino acid, and $X_{59}$ is any amino acid. In some embodiments, peptides of the invention comprise or consist of a sequence of C-S-$X_3$-K-E-$X_6$-K-Q-$X_9$-T-$X_{11}$-$X_{12}$-$X_{13}$-$X_{14}$-G-L-K-Q-$X_{19}$-W-$X_{21}$-G-$X_{23}$-$X_{24}$-$X_{25}$-$X_{26}$-$X_{27}$-G-G-G-G-G-N-F-S-A-K-E-E-$X_{40}$-A-E-T-R-$X_{45}$-T-F-G-L-$X_{50}$-K-Q-Y-D-G-A-$X_{57}$-I-$X_{59}$-E-N-Q-V-Q-N-K-F-T-I-S-N-C (SEQ ID NO: 73), wherein $X_3$ is an amino acid selected from the group consisting of A and V, $X_6$ is an amino acid selected from the group consisting of E and D, $X_9$ is an amino acid selected from the group consisting of T and P, $X_{11}$ is an amino acid selected from the group consisting of T and V, $X_{12}$ is an amino acid selected from the group consisting of G and A, $X_{13}$ is an amino acid selected from the group consisting of L and V, $X_{14}$ is an amino acid selected from the group consisting of Y and F, $X_{19}$ is an amino acid selected from the group consisting of D and N, $X_{21}$ is an amino acid selected from the group consisting of D and N, $X_{23}$ is an amino acid selected from the group consisting of S and V, $X_{24}$ is an amino acid selected from the group consisting of A, S, and T, $X_{25}$ is an amino acid selected from the group consisting of A and I, $X_{26}$ is an amino acid selected from the group consisting of T and P, $X_{27}$ is an amino acid selected from the group consisting of S, N, and K, $X_{40}$ is any amino acid, $X_{45}$ is any amino acid, $X_{50}$ is any amino acid, $X_{57}$ is any amino acid, and $X_{59}$ is any amino acid.

The additional N-terminal peptide sequence can be a native sequence. As used herein, a "native" sequence is a peptide sequence from a naturally-occurring *Ehrlichia* OMP-1 sequence, or a variant thereof. In certain embodiments, the peptide sequence is a fragment of a naturally-occurring *Ehrlichia* OMP-1 sequence. The peptide sequence can be, e.g., from a conserved or non-conserved region of OMP-1. The peptide sequence can comprise, e.g., an epitope, such as an immunodominant epitope or any other epitope recognizable by a host (e.g., human, dog, etc.) immune system. OMP-1 proteins and peptides thereof have been described, e.g., in U.S. Pat. Nos. 6,544,517, 6,893,640, 6,923,963, 7,063,846, and 7,407,770, U.S. Patent Applications 2004/0265333 and 2009/0075368, and European Patent No. 1026949, the contents of which are incorporated herein by reference in their entirety.

Variant polypeptides are at least about 80, 85, 90, 95, 98, or 99% identical to a peptide shown in SEQ ID NOs: 1-73 and 83-86 and are also polypeptides of the invention. Percent sequence identity has an art recognized meaning and there are a number of methods to measure identity between two polypeptide or polynucleotide sequences. See, e.g., Lesk, Ed., Computational Molecular Biology, Oxford University Press, New York, (1988); Smith, Ed., Biocomputing: Informatics And Genome Projects, Academic Press, New York, (1993); Griffin & Griffin, Eds., Computer Analysis Of Sequence Data, Part I, Humana Press, N.J., (1994); von Heinje, Sequence Analysis In Molecular Biology, Academic Press, (1987); and Gribskov & Devereux, Eds., Sequence Analysis Primer, M Stockton Press, New York, (1991). Methods for aligning polynucleotides or polypeptides are codified in computer programs, including the GCG program package (Devereux et al., Nuc. Acids Res. 12:387 (1984)), BLASTP, BLASTN, FASTA (Atschul et al., J Molec. Biol. 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (Adv. App. Math., 2:482-489 (1981)). For example, the computer program ALIGN which employs the FASTA algorithm can be used, with an affine gap search with a gap open penalty of 12 and a gap extension penalty of 2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variants of the peptide sequences can be readily selected by one of skill in the art, based in part on known properties of the sequence. For example, a variant peptide can include amino acid substitutions (e.g., conservative amino acid substitutions) and/or deletions (e.g., small, single amino acid deletions, or deletions encompassing 2, 3, 4, 5, 10, 15, 20, or more contiguous amino acids). Thus, in certain embodiments, a variant of a native peptide sequence is one that differs from a naturally-occurring sequence by (i) one or more (e.g., 2, 3, 4, 5, 6, or more) conservative amino acid substitutions, (ii) deletion of 1 or more (e.g., 2, 3, 4, 5, 6, or more) amino acids, or (iii) a combination thereof. Deleted amino acids can be contiguous or non-contiguous. Conservative amino acid substitutions are those that take place within a family of amino acids that are related in their side chains and chemical properties. These include, e.g., (1) acidic amino acids: aspartate, glutamate; (2) basic amino acids: lysine, arginine, histidine; (3) nonpolar amino acids: alanine, valine, leucine, isoleucine, proline, phenylalanine, methionine, tryptophan; (4) uncharged polar amino acids: glycine, asparagine, glutamine, cysteine, serine, threonine, tyrosine; (5) aliphatic amino acids: glycine, alanine, valine, leucine, isoleucine, serine, threonine, with serine and threonine optionally grouped separately as aliphatic-hydroxyl; (6) aromatic amino acids: phenylalanine, tyrosine, tryptophan; (7) amide amino acids: asparagine, glutamine; and (9) sulfur-containing amino acids: cysteine and methionine. See, e.g., Biochemistry, 2nd ed., Ed. by L. Stryer, W H Freeman and Co.: 1981. Methods for confirming that variant peptides are suitable are conventional and routine.

Variants of the peptide sequences encompass variations on previously defined peptide sequences. For example, a previously described peptide sequence comprising a known epitope may be lengthened or shortened, at one or both ends (e.g., by about 1-3 amino acids), and/or one, two, three, four or more amino acids may be substituted by conservative amino acids, etc. Furthermore, if a region of a protein has been identified as containing an epitope of interest, an investigator can "shift" the region of interest (e.g., by about 5 amino acids in either direction) from the endpoints of the original rough region to optimize the activity.

In certain embodiments, the additional N-terminal peptide sequence can comprise or consist of another peptide having a sequence of SEQ ID NO: 1, SEQ ID NO: 3, SEQ ID NO: 7, SEQ ID NO: 70, SEQ ID NO: 72, SEQ ID NO: 83, or SEQ ID NO: 85. Thus, in some embodiments, a peptide of the invention can be a multimer of sequences having a sequence of SEQ ID NO: 1, SEQ ID NO: 3, SEQ ID NO: 7, SEQ ID NO: 70, SEQ ID NO: 72, SEQ ID NO: 83, or SEQ ID NO: 85. In other embodiments, the N-terminal peptide sequence is a native OMP-1 peptide sequence that is naturally adjacent to the N-terminal end of a sequence of SEQ ID NO: 1, SEQ ID NO: 3, SEQ ID NO: 7, SEQ ID NO: 70, SEQ ID NO: 72, SEQ ID NO: 83, or SEQ ID NO: 85. In other embodiments, the peptide can comprise a fusion of sequences of SEQ ID NO: 1, SEQ ID NO: 3, SEQ ID NO: 7, SEQ ID NO: 70, SEQ ID NO: 72, SEQ ID NO: 83, or SEQ ID NO: 85 optionally through one or more linking amino acids. For example, in one embodiment, the peptide can comprise a sequence of SEQ ID NO: 1 linked to SEQ ID NO: 3 or SEQ ID NO: 85 optionally through one or more linking amino acids (e.g. glycine, serine, or cysteine residues). In another embodiment, the peptide can comprise a sequence of SEQ ID NO: 7 linked to SEQ ID NO: 3 or SEQ ID NO: 85 optionally through one or more linking amino acids (e.g. glycine, serine, or cysteine residues). In another embodiment, the peptide can comprise a sequence of SEQ ID NO: 83 linked to SEQ ID NO: 3 or SEQ ID NO: 85 optionally through one or more linking amino acids (e.g. glycine, serine, or cysteine residues). In still another embodiment, the peptide can comprise a sequence of SEQ ID NO: 1, SEQ ID NO: 7, or SEQ ID NO: 83 linked to SEQ ID NO: 72 optionally through one or more linking amino acids (e.g. glycine, serine, or cysteine residues). In yet another embodiment, the peptide can comprise a sequence of SEQ ID NO: 1, SEQ ID NO: 7, or SEQ ID NO: 83 linked to SEQ ID NO: 71 optionally through one or more linking amino acids (e.g. glycine, serine, or cysteine residues).

In certain embodiments, the additional N-terminal peptide sequence is a non-native sequence. As used herein, a "non-native" sequence is any protein sequence, whether from an *Ehrlichia* protein or otherwise, other than a native OMP-1 peptide sequence. In certain embodiments, the additional N-terminal peptide sequence comprises an epitope of an *Ehrlichia* surface antigen. In certain embodiments, the additional N-terminal peptide sequence comprises an epitope of an *Ehrlichia* antigen, such as p 38, p 43, p 120, p 140, p 153, p 156, p 200, gp19, gp36, gp47, gp200, or HGE-3. Protein and peptide sequences corresponding to *Ehrlichia* antigens have been described. See, e.g., U.S. Pat. Nos. 6,306,402, 6,355,777, 7,204,992, and 7,407,770, and WO2006/138509, the contents of which are incorporated herein by reference in their entirety. Polypeptides or peptides derived from other microorganisms can also be used.

In certain embodiments, the additional N-terminal peptide sequence is a combination of sequences. For example, the additional N-terminal peptide sequence can comprise a native sequence, a non-native sequence, or any combination of such sequences (e.g., two or more native sequences, two or more non-native sequence, or one or more native sequences in combination with one or more non-native sequences).

In certain embodiments, peptides of the invention comprise a sequence defined by SEQ ID NO: 1, SEQ ID NO: 3, SEQ ID NO: 7, SEQ ID NO: 70, SEQ ID NO: 72, SEQ ID NO: 83, or SEQ ID NO: 85 and further comprise an additional C-terminal sequence. The additional C-terminal peptide sequence can comprise 1, 2, 3, 4, 5, 6, 7, 8, 9, 10, 11, 12, 13, 14, 15, 20, 25, or more amino acids. In certain embodiments, the additional C-terminal sequence has a length of about 5 to about 10, about 10 to about 15, about 15 to about 20, about 20 to about 25, about 25 to about 30, about 30 to about 40, or about 40 to about 50 amino acids. The additional C-terminal peptide sequence can be a native OMP-1 sequence. In certain embodiments, the C-terminal peptide sequence is a fragment of a naturally-occurring *Ehrlichia* OMP-1 sequence. The peptide sequence can be, e.g., from a conserved or non-conserved region of OMP-1. The peptide sequence can comprise, e.g., an epitope, such as an immunodominant epitope or any other epitope recognizable by a host (e.g., human, dog, etc.) immune system. In certain embodiments, the additional C-terminal peptide sequence can comprise or consist of another peptide having a sequence of SEQ ID NO: 1, SEQ ID NO: 3, SEQ ID NO: 7, SEQ ID NO: 70, SEQ ID NO: 72, SEQ ID NO: 83, or SEQ ID NO: 85. For example, in certain embodiments, a peptide of the invention can be a multimer of sequences each having a sequence of SEQ ID NO: 1, SEQ ID NO: 3, SEQ ID NO: 7, SEQ ID NO: 70, SEQ ID NO: 72, SEQ ID NO: 83, or SEQ ID NO: 85. In other embodiments, the native sequence is a OMP-1 sequence that is naturally adjacent to the C-terminal end of a sequence of SEQ ID NO: 1, SEQ ID NO: 3, SEQ ID NO: 7, SEQ ID NO: 70, SEQ ID NO: 72, SEQ ID NO: 83, or SEQ ID NO: 85.

In certain embodiments, the additional C-terminal peptide sequence is a non-native sequence. In certain embodiments, the additional C-terminal peptide sequence comprises an epitope of an *Ehrlichia* surface antigen other than OMP-1. In certain embodiments, the additional C-terminal peptide sequence comprises an epitope of an *Ehrlichia* antigen, such as p 38, p 43, p 120, p 140, p 153, p 156, p 200, gp19, gp36, gp47, gp200, or HGE-3. Polypeptides or peptides derived from other microorganisms can also be used.

In certain embodiments, the additional C-terminal peptide sequence is a combination of sequences. For example, the additional C-terminal peptide sequence can comprise a native, a non-native sequence, or any combination of such sequences (e.g., two or more native sequences, two or more non-native sequence, or one or more native sequences in combination with one or more non-native sequences).

In certain embodiments, peptides of the invention comprise a sequence defined by SEQ ID NO: 1, SEQ ID NO: 3, SEQ ID NO: 7, SEQ ID NO: 70, SEQ ID NO: 72, SEQ ID NO: 83, or SEQ ID NO: 85 and further comprise an additional N-terminal peptide sequence and an additional C-terminal peptide sequence. The additional N-terminal and C-terminal peptide sequences can be as described above. Peptides of the invention do not consist of a full-length OMP-1 protein. However, in certain embodiments, peptides of the invention can comprise a full-length OMP-1 protein. In other embodiments, peptides of the invention do not comprise a full-length OMP-1 protein.

A peptide of the invention comprising an additional N-terminal and/or C-terminal peptide sequence can be designed for diagnosing *Ehrlichia* infections early after infection (e.g., within one to two weeks after the onset of infection). For example, in certain embodiments, the additional N-terminal and/or C-terminal peptide sequence comprises an antigen or epitope associated with early stages of *Ehrlichia* infection.

In addition to the sequences described above, the additional N-terminal and C-terminal sequences can comprise or consist of a flexible sequence, designed to better present the peptides of the invention for detection in an immunoassay (e.g., ELISA assay, lateral flow immunoassay, agglutination assay, etc.). Such flexible sequences can be readily identified by persons skilled in the art.

In certain embodiments, peptides of the invention comprise or consist of 25 or more (e.g., 26, 27, 28, 29, or more) amino acid residues. In certain embodiments, peptides of the invention comprise or consist of 30 or more (e.g., 31, 32, 33, 34, or more) amino acid residues. In certain embodiments, peptides of the invention comprise or consist of 35 or more (e.g., 36, 37, 38, 39, or more) amino acid residues. In certain embodiments, peptides of the invention comprise or consist of 40 or more (e.g., 41, 42, 43, 44, or more) amino acid residues. In certain embodiments, peptides of the invention comprise or consist of 45 or more (e.g., 46, 47, 48, 49, or more) amino acid residues. In certain embodiments, peptides of the invention comprise or consist of 50 or more (e.g., 51, 52, 53, 54, or more) amino acid residues. In certain embodiments, peptides of the invention comprise or consist of 55, 60, 65, 70, 75, 80, 85, 90, 95, 100, or more amino acid residues.

In certain embodiments, peptides of the invention comprise an epitope of a peptide sequence described herein. For example, in certain embodiments, peptides of the invention comprise an epitope of a sequence selected from the group consisting of SEQ ID NOs: 1-73 and 83-86.

In certain embodiments, peptides of the invention comprise a fragment of a peptide sequence described herein. For example, in certain embodiments, peptides of the invention comprise a fragment of a sequence selected from the group consisting of SEQ ID NOs: 1-73 and 83-86. The fragment can be, e.g., at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids in length. The fragment can be contiguous or can include one or more deletions (e.g., a deletion of 1, 2, 3, 4, 5, 6, 7, 8, 9, 10, or more amino acid residues). For instance, in one embodiment, peptides of the invention comprise a fragment of SEQ ID NO: 1. Such fragments may comprise at least 10, 15, 20, 25, 30, or 35 contiguous amino acids from SEQ ID NO: 1. In some embodiments, the fragments comprise amino acids 1 to 26 of SEQ ID NO: 1. Thus, in one embodiment, a peptide of the invention comprises or consists of a sequence of S-$X_2$-K-E-D-K-Q-T-T-$X_{10}$-$X_{11}$-I-W-G-L-K-Q-$X_{18}$-W-$X_{20}$-G-$X_{22}$-P-$X_{24}$-$X_{25}$-$X_{26}$ (SEQ ID NO: 84), wherein $X_2$ is an amino acid selected from the group consisting of A and V, $X_{10}$ is an amino acid selected from the group consisting of T and V, $X_{11}$ is an amino acid selected from the group consisting of G and A, $X_{18}$ is an amino acid selected from the group consisting of E and Q, $X_{20}$ is an amino acid selected from the group consisting of D and N, $X_{22}$ is an amino acid selected from the group consisting of S and V, $X_{24}$ is an amino acid selected from the group consisting of A and I, $X_{25}$ is an amino acid selected from the group consisting of T and P, and $X_{26}$ is an amino acid selected from the group consisting of S, N, and K.

In one particular embodiment, peptides of the invention comprise a fragment of SEQ ID NO: 3 or SEQ ID NO: 72. Such fragments may comprise at least 10, 15, 20, 25, 30, 35, or 40 contiguous amino acids from SEQ ID NO: 3 or SEQ ID NO: 72. For instance, in certain embodiments, such fragments may comprise amino acids 1 to 26 of SEQ ID NO: 3 or SEQ ID NO: 72. Thus, in one embodiment, a peptide of the invention comprises or consists of a sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$ (SEQ ID NO: 86), wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, and $X_{26}$ is an amino acid selected from the group consisting of S, N, and K. In other embodiments, the fragments may comprise amino acids 33 to 71 of SEQ ID NO: 3 or SEQ ID NO: 72. Thus, in one embodiment, a peptide of the invention comprises or consists of a sequence of F-S-A-K-E-E-$X_7$-A-$X_9$-T-R-$X_{12}$-T-F-G-$X_{16}$-$X_{17}$-K-Q-Y-D-G-A-$X_{24}$-I-$X_{26}$-E-N-Q-V-Q-N-K-F-T-I-S-N-C(SEQ ID NO: 5), wherein $X_7$ is any amino acid, $X_9$ is an amino acid selected from the group consisting of D and N, $X_{12}$ is any amino acid, $X_{16}$ is an amino acid selected from the group consisting of V and A, $X_{17}$ is any amino acid, $X_{24}$ is any amino acid, and $X_{26}$ is any amino acid. In another embodiment, a peptide of the invention comprises a sequence of C-F-S-A-K-E-E-$X_8$-A-$X_{10}$-T-R-$X_{13}$-T-F-G-$X_{17}$-$X_{18}$-K-Q-Y-D-G-A-$X_{25}$-I-$X_{27}$-E-N-Q-V-Q-N-K-F-T-I-S-N(SEQ ID NO: 6), wherein $X_8$ is any amino acid, $X_{10}$ is an amino acid selected from the group consisting of D and N, $X_{13}$ is any amino acid, $X_{17}$ is an amino acid selected from the group consisting of V and A, $X_{18}$ is any amino acid, $X_{25}$ is any amino acid, and $X_{27}$ is any amino acid. In still another embodiment, a peptide of the invention comprises a sequence of F-S-A-K-E-E-$X_7$-A-E-T-R-$X_{12}$-T-F-G-L-$X_{17}$-K-Q-Y-D-G-A-$X_{24}$-I-$X_{26}$-E-N-Q-V-Q-N-K-F-T-I-S-N-C (SEQ ID NO: 71), wherein $X_7$ is any amino acid, $X_{12}$ is any amino acid, $X_{17}$ is any amino acid, $X_{24}$ is any amino acid, and $X_{26}$ is any amino acid.

In certain embodiments, the fragment comprises a sequence set forth in U.S. Pat. Nos. 6,306,402, 6,355,777, 7,204,992, or 7,407,770, or in WO2006/138509. In certain embodiments, the fragment does not consist of a sequence set forth in one or more of U.S. Pat. Nos. 6,306,402, 6,355,777, 7,204,992, and 7,407,770, and WO2006/138509. Peptides of the invention that comprise a fragment of a peptide sequence described herein can further comprise an additional N-terminal peptide sequence, an additional C-terminal peptide sequence, or a combination thereof. The additional N-terminal and C-terminal peptide sequences can be as described above.

Peptides of the invention comprising an additional N-terminal or C-terminal peptide sequence can further comprise a linker connecting the peptide (e.g., a peptide of SEQ ID NO: 1, SEQ ID NO: 3, SEQ ID NO: 7, SEQ ID NO: 70, SEQ ID NO: 72, SEQ ID NO: 83, SEQ ID NO: 85, or a fragment thereof) with the additional N-terminal or C-terminal peptide sequence. The linker can be, e.g., a peptide spacer. Such spacer can consist of, for example, between about one and five (e.g., about three) amino acid residues, preferably uncharged amino acids, e.g., aliphatic residues such as glycine or alanine. In one embodiment, the spacer is a triplet glycine spacer. In another embodiment, the spacer is a triplet alanine spacer. In yet another embodiment, the spacer comprises both glycine and alanine residues. Alternatively, the linker can be a chemical (i.e., non-peptide) linker.

In certain embodiments, peptides of the invention are produced by synthetic chemistry (i.e., a "synthetic peptide"). In other embodiments, peptides of the invention are produced biologically (i.e., by cellular machinery, such as a ribosome). In certain embodiments, peptides of the invention are isolated. As used herein, an "isolated" peptide is a peptide that has been produced either synthetically or biologically and then purified, at least partially, from the chemicals and/or cellular machinery used to produce the peptide. In certain embodiments, an isolated peptide of the invention is substantially purified. The term "substantially purified," as used herein, refers to a molecule, such as a peptide, that is substantially free of cellular material (proteins, lipids, carbohydrates, nucleic acids, etc.), culture medium, chemical precursors, chemicals used in synthesis of the peptide, or combinations thereof. A peptide that is substantially purified has less than about 40%, 30%, 25%, 20%, 15%, 10%, 5%, 2%, 1% or less of the cellular material, culture medium, other polypeptides, chemical precursors, and/or chemicals used in synthesis of the peptide. Accordingly, a substantially pure molecule, such as a peptide, can be at least about 60%, 70%, 75%, 80%, 85%, 90%, 95%, 98%, or 99%, by dry weight, the molecule of interest. An isolated peptide of the invention can be in water, a buffer, or in a dry form awaiting reconstitution, e.g., as part of a kit. An isolated peptide of the present invention can be in the form of a pharmaceutically acceptable salt. Suitable acids and bases that are capable of forming salts with the peptides of the present invention are well known to those of skill in the art, and include inorganic and organic acids and bases.

In certain embodiments, peptides of the invention are affinity purified. For example, in certain embodiments, the peptides of the invention are purified by means of their ability to bind to anti-*Ehrlichia* antibodies (e.g., antibodies to OMP-1 proteins and, optionally, other *Ehrlichia* antigens) by contacting such antibodies with the peptides of the invention such that peptide-antibody complexes are able to form, washing the peptide-antibody complexes to remove impurities, and then eluting the peptides from the antibodies. The antibodies can be, e.g., attached to a solid support. Methods of affinity purification are well-known and routine to those skilled in the art.

In certain embodiments, peptides of the invention are modified. The peptides of the invention may be modified by a variety of techniques, such as by denaturation with heat and/or a detergent (e.g., SDS). Alternatively, peptides of the invention may be modified by association with one or more further moieties. The association can be covalent or non-covalent, and can be, for example, via a terminal amino acid linker, such as lysine or cysteine, a chemical coupling agent, or a peptide bond. The additional moiety can be, for example, a ligand, a ligand receptor, a fusion partner, a detectable label, an enzyme, or a substrate that immobilizes the peptide.

Peptides of the invention can be conjugated to a ligand, such as biotin (e.g., via a cysteine or lysine residue), a lipid molecule (e.g., via a cysteine residue), or a carrier protein (e.g., serum albumin, immunoglobulin Fc domain, keyhole limpet hemocyanin (KLH) via e.g., a cysteine or lysine residue). Attachment to ligands, such as biotin, can be useful for associating the peptide with ligand receptors, such as avidin, streptavidin, polymeric streptavidin (see e.g., US 2010/0081125 and US 2010/0267166, both of which are herein incorporated by reference), or neutravidin. Avidin, streptavidin, polymeric streptavidin, or neutravidin, in turn, can be linked to a signaling moiety (e.g., an enzyme, such as horse radish peroxidase (HRP) or alkaline phosphatase (ALP), or other moiety that can be visualized, such as a metallic nanoparticle or nanoshell (e.g., colloidal gold) or a fluorescent moiety) or a solid substrate (e.g., an Immobilon™ or nitrocellulose membrane). Alternatively, the peptides of the invention can be fused or linked to a ligand receptor, such as avidin, streptavidin, polymeric streptavidin, or neutravidin, thereby facilitating the association of the peptides with the corresponding ligand, such as biotin and any moiety (e.g., signaling moiety) or solid substrate attached thereto. Examples of other ligand-receptor pairs are well-known in the art and can similarly be used.

Peptides of the invention can be fused to a fusion partner (e.g., a peptide or other moiety) that can be used to improve purification, to enhance expression of the peptide in a host cell, to aid in detection, to stabilize the peptide, etc. Examples of suitable compounds for fusion partners include carrier proteins (e.g., serum albumin, immunoglobulin Fc domain, KLH), enzymes (e.g., horse radish peroxidase (HRP), beta-galactosidase, glutathione-S-transferase, alkaline phosphatase), a histidine tag, etc. The fusion can be achieved by means of, e.g., a peptide bond. For example, peptides of the invention and fusion partners can be fusion proteins and can be directly fused in-frame or can comprise a peptide linker, as discussed above in the context of additional N-terminal and C-terminal peptide sequences. In certain embodiments, a mixture of peptides of the invention can be linked by a dendrimer, e.g., as in a MAPS structure.

In addition, peptides of the invention may be modified to include any of a variety of known chemical groups or molecules. Such modifications include, but are not limited to, glycosylation, acetylation, acylation, ADP-ribosylation, amidation, covalent attachment to polyethylene glycol (e.g., PEGylation), covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, ubiquitination, modifications with fatty acids, transfer-RNA mediated addition of amino acids to proteins such as arginylation, etc. Analogues of an amino acid (including unnatural amino acids) and peptides with substituted linkages are also included. Peptides of the invention that consist of any of the sequences discussed herein may be modified by any of the discussed modifications. Such peptides still "consist of" the amino acids.

Modifications as set forth above are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in many basic texts, such as Proteins-Structure and Molecular Properties, 2nd ed., T. E. Creighton, W.H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (1990) Meth. Enzymol. 182:626-646 and Rattan et al. (1992) Ann. N.Y. Acad. Sci. 663:48-62.

In certain embodiments, peptides of the invention are attached to or immobilized on a substrate, such as a solid or semi-solid support. The attachment can be covalent or non-covalent, and can be facilitated by a moiety associated with the peptide that enables covalent or non-covalent binding, such as a moiety that has a high affinity to a component attached to the carrier, support or surface. For example, the peptide can be associated with a ligand, such as biotin, and the component associated with the surface can be a corresponding ligand receptor, such as avidin. In some embodiments, the peptide can be associated with a fusion partner, e.g., bovine serum albumin (BSA), which facilitates the attachment of the peptide to a substrate. In other embodiments, the peptides of the invention are attached to or immobilized on a substrate via a metallic nanolayer. In one embodiment, the metallic nanolayer is comprised of cadmium, zinc, mercury, or a noble metal, such as gold, silver, copper, and platinum. The peptide or mixture of peptides can be attached to or immobilized on the substrate either prior to or after the addition of a sample containing antibody during an immunoassay.

In certain embodiments, the substrate is a bead, such as a colloidal particle (e.g., a colloidal nanoparticle made from gold, silver, platinum, copper, cadmium, metal composites, other soft metals, core-shell structure particles, or hollow gold nanospheres) or other type of particle (e.g., a magnetic bead or a particle or nanoparticle comprising silica, latex, polystyrene, polycarbonate, polyacrylate, or PVDF). Such particles can comprise a label (e.g., a colorimetric, chemiluminescent, or fluorescent label) and can be useful for visualizing the location of the peptides during immunoassays. In certain embodiments, a terminal cysteine of a peptide of the invention is used to bind the peptide directly to the nanoparticles made from gold, silver, platinum, copper, cadmium, metal composites, or other soft metals, or metallic nanoshells (e.g., gold hollow spheres, gold-coated silica nanoshells, and silica-coated gold shells).

In certain embodiments, the substrate is a dot blot or a flow path in a lateral flow immunoassay device. For example, the peptides can be attached or immobilized on a porous membrane, such as a PVDF membrane (e.g., an Immobilon™ membrane), a nitrocellulose membrane, polyethylene membrane, nylon membrane, or a similar type of membrane.

In certain embodiments, the substrate is a flow path in an analytical or centrifugal rotor. In other embodiments, the substrate is a tube or a well, such as a well in a plate (e.g., a microtiter plate) suitable for use in an ELISA assay. Such substrates can comprise glass, cellulose-based materials, thermoplastic polymers, such as polyethylene, polypropylene, or polyester, sintered structures composed of particulate materials (e.g., glass or various thermoplastic polymers), or cast membrane film composed of nitrocellulose, nylon, polysulfone, or the like. A substrate can be sintered, fine particles of polyethylene, commonly known as porous polyethylene, for example, 0.2-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

Accordingly, in another aspect, the invention provides devices. In certain embodiments, the devices are useful for performing an immunoassay. For example, in certain embodiments, the device is a lateral flow immunoassay device. In some embodiments, the device is a slide comprised of a plurality of beads to which a peptide or population of peptides is attached. In other embodiments, the device is an analytical or centrifugal rotor. In other embodiments, the device is a dot blot, slot blot, or Western blot. In other embodiments, the device is a tube or a well, e.g., in a plate suitable for an ELISA assay. In still other embodiments, the device is an electrochemical sensor, an optical sensor, or an opto-electronic sensor.

In certain embodiments, the device comprises a peptide or population of peptides of the invention. In other embodiments, the device comprises a mixture of different peptides of the invention. For example, in certain embodiments, the device comprises two, three, four, or more different peptides of the invention. In certain embodiments, the peptide or each peptide in the mixture comprises a sequence of SEQ ID NO: 1, SEQ ID NO: 3, SEQ ID NO: 7, SEQ ID NO: 70, SEQ ID NO: 72, SEQ ID NO: 83, SEQ ID NO: 85 or a fragment thereof. In other embodiments, the peptide or each peptide in the mixture comprises a sequence of SEQ ID NO: 1, SEQ ID NO: 3, SEQ ID NO: 72, or a fragment thereof. In certain embodiments, the mixture or population of peptides are attached to or immobilized upon the device optionally through a metallic nanolayer. The devices may be used to detect the presence of antibodies to *Ehrlichia* antigens from multiple species (e.g., *E. canis, E. chaffeensis, E. ewingii*, and *E. muris*) in a sample simultaneously. In one embodiment, the device comprises a population of isolated peptides comprising three or more different peptides, wherein each peptide in the population comprises a sequence of SEQ ID NO: 72. In related embodiments, the population of isolated peptides further comprises peptides comprising a sequence of SEQ ID NO: 3 and/or SEQ ID NO: 71. In another embodiment, the device comprises a population of isolated peptides comprising three or more different peptides, wherein each peptide in the population comprises a sequence of SEQ ID NO: 3. In another embodiment, the device comprises a population of isolated peptides comprising three or more different peptides, wherein each peptide in the population comprises a sequence of SEQ ID NO: 1. In still another embodiment, the device comprises a population of isolated peptides comprising three or more different peptides, wherein each peptide in the population comprises a sequence of SEQ ID NO: 71. In other embodiments, the device comprises a population of isolated peptides comprising three or more different peptides, wherein each peptide in the population comprises a sequence of SEQ ID NO: 7, SEQ ID NO: 70, SEQ ID NO: 83, or SEQ ID NO: 85.

In another aspect, the invention provides compositions comprising one or more peptides of the invention. For example, in certain embodiments, the invention provides a composition comprising a peptide comprising a sequence of SEQ ID NO: 1, or mixtures thereof. In certain embodiments, the composition comprises a mixture of 2, 3, 4, 5, 6, 7, 8, 9, 10, 15, 20, 25, 30, 40, 50, 60, 70, 80, 90, 100, 150, 200, 250, 300, 400, 500, or more peptides (e.g., all possible peptides defined by SEQ ID NO: 1). Thus, the present invention provides a population of isolated peptides comprising three or more different peptides, wherein each peptide in the population comprises a sequence of SEQ ID NO: 1. In certain embodiments, the peptides in the population or mixture comprise an N-terminal and/or C-terminal addition, and/or are modified (e.g., by association with one or more further moieties), as described herein. In certain embodiments, the peptides comprise the same N-terminal and/or C-terminal additions. In other embodiments, the peptides comprise different N-terminal and/or C-terminal additions.

In still other embodiments, the invention provides a composition comprising a peptide comprising a sequence of SEQ ID NO: 3, SEQ ID NO: 5, SEQ ID NO: 7, SEQ ID NO: 70, SEQ ID NO: 72, SEQ ID NO: 83, SEQ ID NO: 85, or mixtures thereof. In certain embodiments, the composition comprises a mixture of 2, 3, 4, 5, 6, 7, 8, 9, 10, 15, 20, 25, 30, 40, 50, 60, 70, 80, 90, 100, 150, 200, 250, 300, 400, 500, or more peptides (e.g., all possible peptides defined by SEQ ID NO: 3, SEQ ID NO: 5, SEQ ID NO: 7, SEQ ID NO: 70, SEQ ID NO: 72, SEQ ID NO: 83, or SEQ ID NO: 85). Thus, the invention provides a population of isolated peptides comprising three or more different peptides, wherein each peptide in the population comprises a sequence of SEQ ID NO: 3. In another embodiment, the invention provides a population of isolated peptides comprising three or more different peptides, wherein each peptide in the population comprises a sequence of SEQ ID NO: 72. In other embodiments, the invention provides a population of isolated peptides comprising three or more different peptides, wherein each peptide in the population comprises a sequence of SEQ ID NO: 5, SEQ ID NO: 7, SEQ ID NO: 70, SEQ ID NO: 83, or SEQ ID NO: 85. The peptides in the population or mixture may comprise an N-terminal and/or C-terminal addition, and/or be modified (e.g., by association with one or more further moieties), as described herein.

In certain embodiments, the compositions comprise one or more peptides (or one or more populations of peptides) of the invention and one or more additional peptides, such as an *Ehrlichia* peptide or antigen, a peptide or antigen from one or more infectious *Ehrlichia* species, or a peptide or antigen from one or more causative agents of monocytic and/or granulocytic ehrlichiosis. The *Ehrlichia* peptide or antigen can be any *Ehrlichia* surface peptide or antigen, or any peptide or antigen described herein (e.g., any peptide or antigen of an OMP-1, p 38, p 43, p 120, p 140, p 153, p 156, p 200, gp19, gp36, gp47, gp200, or HGE-3 protein, or any fragment or epitope thereof). The combination may comprise a cocktail (a simple mixture) of individual peptides or polypeptides, it may be in the form of a fusion peptide or polypeptide (e.g., a multimeric peptide), or the peptides may be linked by a dendrimer (e.g., as in a MAPS structure) optionally through a linking residue (e.g. lysine or cysteine residue). For instance, in certain embodiments, a composition comprises one or more peptides of the invention (e.g., a peptide having a sequence of SEQ ID NO: 1, SEQ ID NO: 3, SEQ ID NO: 5, SEQ ID NO: 7, SEQ ID NO: 70, SEQ ID NO: 72, SEQ ID NO: 83, or SEQ ID NO: 85) and one or more antigenic *Ehrlichia* peptides having a sequence of F-S-A-K-E-E-$X_7$-A-E-T-R-$X_{12}$-T-F-G-L-$X_{17}$-K-Q-Y-D-G-A-$X_{24}$-I-$X_{26}$-E-N-Q-V-Q-N-K-F-T-I-S-N-C(SEQ ID NO: 71) or a fragment thereof, wherein $X_7$ is any amino acid, $X_{12}$ is any amino acid, $X_{17}$ is any amino acid, $X_{24}$ is any amino acid, and $X_{26}$ is any amino acid. In some embodiments, $X_7$ is K. In other embodiments, $X_{12}$ is an amino acid selected from the group consisting of K and R, and $X_{17}$ is an amino acid selected from the group consisting of E and D. In still other embodiments, $X_{24}$ is an amino acid selected from the group consisting of K and Q, and $X_{26}$ is an amino acid selected from the group consisting of E and T.

In certain embodiments, the mixture or population of peptides comprises one or more peptides having a sequence of SEQ ID NO: 3 and one or more peptides having a sequence of SEQ ID NO: 71. In still other embodiments, the mixture or population of peptides comprises one or more peptides having a sequence of SEQ ID NO: 1 and one or more peptides having a sequence of SEQ ID NO: 71. In one embodiment, the mixture or population of peptides comprises one or more peptides having a sequence of SEQ ID NO: 3 and one or more peptides having a sequence of SEQ ID NO: 72. In another embodiment, the mixture or population of peptides comprises one or more peptides having a sequence of SEQ ID NO: 72 and one or more peptides having a sequence of SEQ ID NO: 71. In one particular embodiment, the mixture or population of peptides comprises one or more peptides having a sequence of SEQ ID NO: 3, one or more peptides having a sequence of SEQ ID NO: 72, and one or more peptides having a sequence of SEQ ID NO: 71. Such mixtures enable the detection of antibodies to *Ehrlichia* antigens from multiple species (e.g., *E. canis, E. chaffeensis, E. ewingii*, and *E. muris*) in a sample simultaneously.

A peptide of the invention may be fused at its N-terminus or C-terminus to another suitable peptide. Two or more copies of a peptide of the invention may be joined to one another, alone or in combination with one or more additional peptides. Combinations of fused and unfused peptides or polypeptides can be used. In one embodiment, the additional peptide(s) contain B-cell and/or T-cell epitopes from an *Ehrlichia* peptide or antigen, a peptide or antigen from an infectious *Ehrlichia* species, or a peptide or antigen from a causative agent of monocytic and/or granulocytic ehrlichiosis.

In another aspect, the invention provides nucleic acids comprising a sequence encoding a peptide of the invention. Nucleic acids of the invention contain less than an entire microbial genome and can be single- or double-stranded. A nucleic acid can be RNA, DNA, cDNA, genomic DNA, chemically synthesized RNA or DNA or combinations thereof. The nucleic acids can be purified free of other components, such as proteins, lipids and other polynucleotides. For example, the nucleic acids can be 50%, 75%, 90%, 95%, 96%, 97%, 98%, 99%, or 100% purified. The nucleic acids of the invention encode the peptides described herein. In certain embodiments, the nucleic acids encode a peptide having the sequence of SEQ ID NOs: 1-73 and 83-86, or combinations thereof. Nucleic acids of the invention can comprise other nucleotide sequences, such as sequences coding for linkers, signal sequences, TMR stop transfer sequences, transmembrane domains, or ligands useful in protein purification such as glutathione-S-transferase, histidine tag, and staphylococcal protein A.

Nucleic acids of the invention can be isolated. An “isolated” nucleic acids is one that is not immediately contiguous with one or both of the 5' and 3' flanking genomic sequences with which it is naturally associated. An isolated nucleic acid can be, e.g., a recombinant DNA molecule of any length, provided that the nucleic acid sequences naturally found immediately flanking the recombinant DNA molecule in a naturally-occurring genome is removed or absent. Isolated nucleic acids also include non-naturally occurring nucleic acid molecules. Nucleic acids of the invention can also comprise fragments that encode immunogenic peptides. Nucleic acids of the invention can encode full-length polypeptides, peptide fragments, and variant or fusion peptides.

Nucleic acids of the invention can be isolated, at least in part, from nucleic acid sequences present in, for example, a biological sample, such as blood, serum, saliva, or tissue from an infected individual. Nucleic acids can also be synthesized in the laboratory, for example, using an automatic synthesizer. An amplification method such as PCR can be used to amplify nucleic acids, at least in part, from either genomic DNA or cDNA encoding the polypeptides.

Nucleic acids of the invention can comprise coding sequences for naturally occurring polypeptides or can encode altered sequences that do not occur in nature. If desired, nucleic acids can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColEl, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A nucleic acid of the invention is operably linked when it is positioned adjacent to or close to one or more expression control elements, which direct transcription and/or translation of the polynucleotide.

Thus, for example, a peptide of the invention can be produced recombinantly following conventional genetic engineering techniques. To produce a recombinant peptide of the invention, a nucleic acid encoding the peptide is inserted into a suitable expression system. Generally, a recombinant molecule or vector is constructed in which the polynucleotide sequence encoding the selected peptide is operably linked to an expression control sequence permitting expression of the peptide. Numerous types of appropriate expression vectors are known in the art, including, e.g., vectors containing bacterial, viral, yeast, fungal, insect or mammalian expression systems. Methods for obtaining and using such expression vectors are well-known. For guidance in this and other molecular biology techniques used for compositions or methods of the invention, see, e.g., Sambrook et al., Molecular Cloning, A Laboratory Manual, current edition, Cold Spring Harbor Laboratory, New York; Miller et al, Genetic Engineering, 8:277-298 (Plenum Press, current edition), Wu et al., Methods in Gene Biotechnology (CRC Press, New York, N.Y., current edition), Recombinant Gene Expression Protocols, in Methods in Molecular Biology, Vol. 62, (Tuan, ed., Humana Press, Totowa, N.J., current edition), and Current Protocols in Molecular Biology, (Ausabel et al., Eds.) John Wiley & Sons, N.Y. (current edition), and references cited therein.

Accordingly, the invention also provides vectors comprising nucleic acids of the invention, and host cells comprising such vectors. In certain embodiments, the vector is a shuttle vector. In other embodiments, the vector is an expression vector (e.g., a bacterial or eukaryotic expression vector). In certain embodiments, the host cell is a bacterial cell. In other embodiments, the host cell is a eukaryotic cell.

Suitable host cells or cell lines for the recombinant nucleic acids or vectors of the invention transfection by this method include bacterial cells. For example, various strains of *E. coli* (e.g., HB101, MC1061) are well-known as host cells in the field of biotechnology. Various strains of *B. subtilis, Pseudomonas, Streptomyces*, and other bacilli and the like can also be employed in this method. Alternatively, a peptide of the invention can be expressed in yeast, insect, mammalian, or other cell types, using conventional procedures. Cell-free in vitro synthesis and/or enzyme-mediated synthetic machineries may also be used.

The present invention also provides a method for producing a recombinant peptide or polypeptide, which involves transfecting or transforming, e.g., by conventional means such as electroporation, a host cell with at least one expression vector containing a polynucleotide of the invention under the control of an expression control sequence (e.g., a transcriptional regulatory sequence). The transfected or transformed host cell is then cultured under conditions that allow expression of the peptide or polypeptide. The expressed peptide or polypeptide is recovered, isolated, and optionally purified from the cell (or from the culture medium, if expressed extracellularly) by appropriate means known to one of skill in the art, including liquid chromatography such as normal or reversed phase, using HPLC, FPLC and the like, affinity chromatography, such as with inorganic ligands or monoclonal antibodies, size exclusion chromatography, immobilized metal chelate chromatography, gel electrophoresis, and the like. One of skill in the art may select the most appropriate isolation and purification techniques without departing from the scope of this invention. One skilled in the art can determine the purity of the peptide or polypeptide by using standard methods including, e.g., polyacrylamide gel electrophoresis (e.g., SDS-PAGE), capillary electrophoresis, column chromatography (e.g., high performance liquid chromatography (HPLC)), amino-terminal amino acid analysis, and quantitative amino acid analysis.

Methods

In another aspect, the invention provides methods of detecting in a sample an antibody to an epitope of an *Ehrlichia* antigen. In certain embodiments, the methods comprise contacting a sample with a peptide of the invention, and detecting formation of an antibody-peptide complex comprising said peptide, wherein formation of said complex is indicative of the presence of an antibody to an epitope of an *Ehrlichia* antigen in said sample. In some embodiments, the *Ehrlichia* antigen is from an infectious *Ehrlichia* species. In certain embodiments, the *Ehrlichia* antigen is from a pathogenic *Ehrlichia* species, such as *Ehrlichia chaffeensis, E. ewingu, E. muris*, or *Ehrlichia canis*. Other species of *Ehrlichia* which have been implicated in monocytic and/or granulocytic ehrlichiosis can also be detected using the methods of the invention, provided they induce antibodies which can react specifically with a peptide of the invention. Thus, it is to be understood that the term "pathogenic *Ehrlichia*," as used herein, refers to any such *Ehrlichia* species that causes monocytic and/or granulocytic ehrlichiosis. In particular embodiments, the methods provide detection of antibodies to *Ehrlichia* antigens from multiple species (e.g., *E. canis, E. chaffeensis, E. ewingii*, and *E. muris*) in a sample simultaneously.

In certain embodiments, the methods comprise contacting the sample with a mixture or population of two, three, four, or more (e.g., 5, 6, 7, 8, 9, 10, 15, 20, 25, 30, 40, 50, 60, 70, 80, 90, 100, 150, 200, 250, 300, 400, 500, or more) different peptides of the invention. For instance, in one particular embodiment, the methods comprise contacting the sample with a mixture or population of two or more different isolated peptides, wherein each isolated peptide comprises a sequence of SEQ ID NO: 1. In another particular embodiment, the methods comprise contacting the sample with a mixture or population of two or more different isolated peptides, wherein each isolated peptide comprises a sequence of SEQ ID NO: 3. In still another embodiment, the methods comprise contacting the sample with a mixture or population of two or more different isolated peptides, wherein each isolated peptide comprises a sequence of SEQ ID NO: 72. In some embodiments, the methods comprise contacting the sample with a mixture or population of two or more different isolated peptides, wherein each isolated peptide comprises a sequence of SEQ ID NO: 1, SEQ ID NO: 3, or SEQ ID NO: 72. In other embodiments, the methods comprise contacting the sample with a mixture or population of two or more different isolated peptides, wherein each isolated peptide comprises a sequence of SEQ ID NO: 5, SEQ ID NO: 7, SEQ ID NO: 70, SEQ ID NO: 83, or SEQ ID NO: 85.

In certain embodiments, the methods comprise contacting the sample with a mixture of one or more peptides of the invention and one or more other peptides (e.g., an *Ehrlichia* peptide, or antigenic fragment or epitope thereof, such as an *Ehrlichia* surface antigen, or an OMP-1, p 38, p 43, p 120, p 140, p 153, p 156, p 200, gp19, gp36, gp47, gp200, or HGE-3 protein). For instance, in some embodiments, the methods comprise contacting the sample with a mixture of one or more peptides of the invention (e.g., SEQ ID NO: 1, SEQ ID NO: 3, SEQ ID NO: 5, SEQ ID NO: 7, SEQ ID NO: 70, SEQ ID NO: 72, SEQ ID NO: 83, or SEQ ID NO: 85) and one or more *Ehrlichia* antigenic peptides having a sequence of SEQ ID NO: 71. In one particular embodiment, the methods comprise contacting the sample with a mixture of one or more peptides having a sequence of SEQ ID NO: 3 and one or more peptides having a sequence of SEQ ID NO: 71. In another embodiment, the methods comprise contacting the sample with a mixture of one or more peptides having a sequence of SEQ ID NO: 72 and one or more peptides having a sequence of SEQ ID NO: 71. In another embodiment, the methods comprise contacting the sample with a mixture of one or more peptides having a sequence of SEQ ID NO: 72 and one or more peptides having a sequence of SEQ ID NO: 3. In one embodiment, the methods comprise contacting the sample with a mixture of one or more peptides having a sequence of SEQ ID NO: 72, one or more peptides having a sequence of SEQ ID NO: 3, and one or more peptides having a sequence of SEQ ID NO: 71. Mixtures of peptides of the invention allow, in some embodiments, for the detection of antibodies to antigens from multiple *Ehrlichia* species (e.g., *E. canis, E. muris, E. chaffeensis*, and *E. ewingii*) in a sample simultaneously.

In certain embodiments, the peptide or each peptide in the mixture or population is an isolated (e.g., synthetic and/or purified) peptide. In certain embodiments, the peptide or mixture of peptides (i.e. population of peptides) is attached to or immobilized upon a solid support. In certain embodiments, the solid support is a bead (e.g., a metallic nanoparticle or nanoshell, a nanoparticle, a latex bead, etc.), a flow path in a lateral flow immunoassay device (e.g., a porous membrane), a flow path in an analytical or centrifugal rotor, a blot (Western blot, dot blot, or slot blot), a tube or a well (e.g., in a plate suitable for an ELISA assay), or a sensor (e.g., an electrochemical, optical, or opto-electronic sensor). In some embodiments, the peptide or mixture of peptides is attached to or immobilized upon a solid support through a metallic nanolayer that, in some embodiments, may be comprised of cadmium, zinc, mercury, or a noble metal (e.g., gold, silver, copper, and platinum).

In certain embodiments, the detecting step comprises performing an ELISA or immunofluorescence assay. In other embodiments, the detecting step comprises performing a lateral flow immunoassay. In other embodiments, the detecting step comprises performing an agglutination assay (e.g., a hemagglutination or particle/bead agglutination assay). In other embodiments, the detecting step comprises spinning the sample in an analytical or centrifugal rotor. In some embodiments, the detecting step comprises performing a wavelength shift assay. Such wavelength shift assays may entail measuring or determining a change in the surface plasmon resonance or localized surface plasmon resonance wavelength resulting from binding of antibodies to peptides attached to metallic nanolayers or metallic nanoparticle/nanoshells. In still other embodiments, the detecting step comprises analyzing the sample with an electrochemical, optical, or opto-electronic sensor.

There are a number of different conventional assays for detecting formation of an antibody-peptide complex comprising a peptide of the invention. For example, the detecting step can comprise performing an ELISA assay, performing an immunofluorescence assay, performing a lateral flow immunoassay, performing an agglutination assay, performing a wavelength shift assay, performing a Western blot, slot blot, or dot blot, analyzing the sample in an analytical or centrifugal rotor, or analyzing the sample with an electrochemical, optical, or opto-electronic sensor. These different assays are described herein and/or are well-known to those skilled in the art.

In one embodiment, the methods involve detecting the presence of naturally occurring antibodies against one or more *Ehrlichia* antigens (e.g., the antigen of a pathogenic *Ehrlichia*, such as *E. chaffeensis, E. muris, E. ewingii*, or *E. canis*) which are produced by the infected subject's immune system in its biological fluids or tissues, and which are capable of binding specifically to a peptide of the invention or combinations of a peptide of the invention and, optionally, one or more suitable additional antigenic polypeptides or peptides.

Suitable immunoassay methods typically include: receiving or obtaining (e.g., from a patient) a sample of body fluid or tissue likely to contain antibodies; contacting (e.g., incubating or reacting) a sample to be assayed with a peptide of the invention, under conditions effective for the formation of a specific peptide-antibody complex (e.g., for specific binding of the peptide to the antibody); and assaying the contacted (reacted) sample for the presence of an antibody-peptide reaction (e.g., determining the amount of an antibody-peptide complex). The presence of an elevated amount of the antibody-peptide complex indicates that the subject was exposed to and infected with an infectious *Ehrlichia* species. A peptide, including a modified form thereof, which "binds specifically" to (e.g., "is specific for" or binds "preferentially" to) an antibody against an *Ehrlichia* antigen interacts with the antibody, or forms or undergoes a physical association with it, in an amount and for a sufficient time to allow detection of the antibody. By "specifically" or "preferentially," it is meant that the peptide has a higher affinity (e.g., a higher degree of selectivity) for such an antibody than for other antibodies in a sample. For example, the peptide can have an affinity for the antibody of at least about 1.5-fold, 2-fold, 2.5-fold, 3-fold, or higher than for other antibodies in the sample. Such affinity or degree of specificity can be determined by a variety of routine procedures, including, e.g., competitive binding studies. In an ELISA assay, a positive response is defined as a value 2 or 3 standard deviations greater than the mean value of a group of healthy controls. In some embodiments, a second tier assay is required to provide an unequivocal serodiagnosis of monocytic and/or granulocytic ehrlichiosis.

Phrases such as "sample containing an antibody" or "detecting an antibody in a sample" are not meant to exclude samples or determinations (e.g., detection attempts) where no antibody is contained or detected. In a general sense, this invention involves assays to determine whether an antibody produced in response to infection with an infectious *Ehrlichia* is present in a sample, irrespective of whether or not it is detected.

Conditions for reacting peptides and antibodies so that they react specifically are well-known to those of skill in the art. See, e.g., Current Protocols in Immunology (Coligan et al., editors, John Wiley & Sons, Inc).

The methods comprise receiving or obtaining a sample of body fluid or tissue likely to contain antibodies from a subject. The antibodies can be, e.g., of IgG, IgE, IgD, IgM, or IgA type. Generally, IgM and/or IgA antibodies are detected, e.g., for detection at early stages of infection. IgG antibodies can be detected when some of the additional peptides discussed above are used in the method (e.g., peptides for the detection of flagellum proteins). The sample is preferably easy to obtain and may be whole blood, plasma, or serum derived from a venous blood sample or even from a finger prick. Tissue from other body parts or other bodily fluids, such as cerebro-spinal fluid (CSF), saliva, gastric secretions, mucus, urine, etc., are known to contain antibodies and may be used as a source of the sample. The sample may also be a tissue extract or a cell lysate.

Once the peptide antigen and sample antibody are permitted to react in a suitable medium, an assay is performed to determine the presence or absence of an antibody-peptide reaction. Among the many types of suitable assays, which will be evident to a skilled worker, are immunoprecipitation and agglutination assays.

Figure 2:
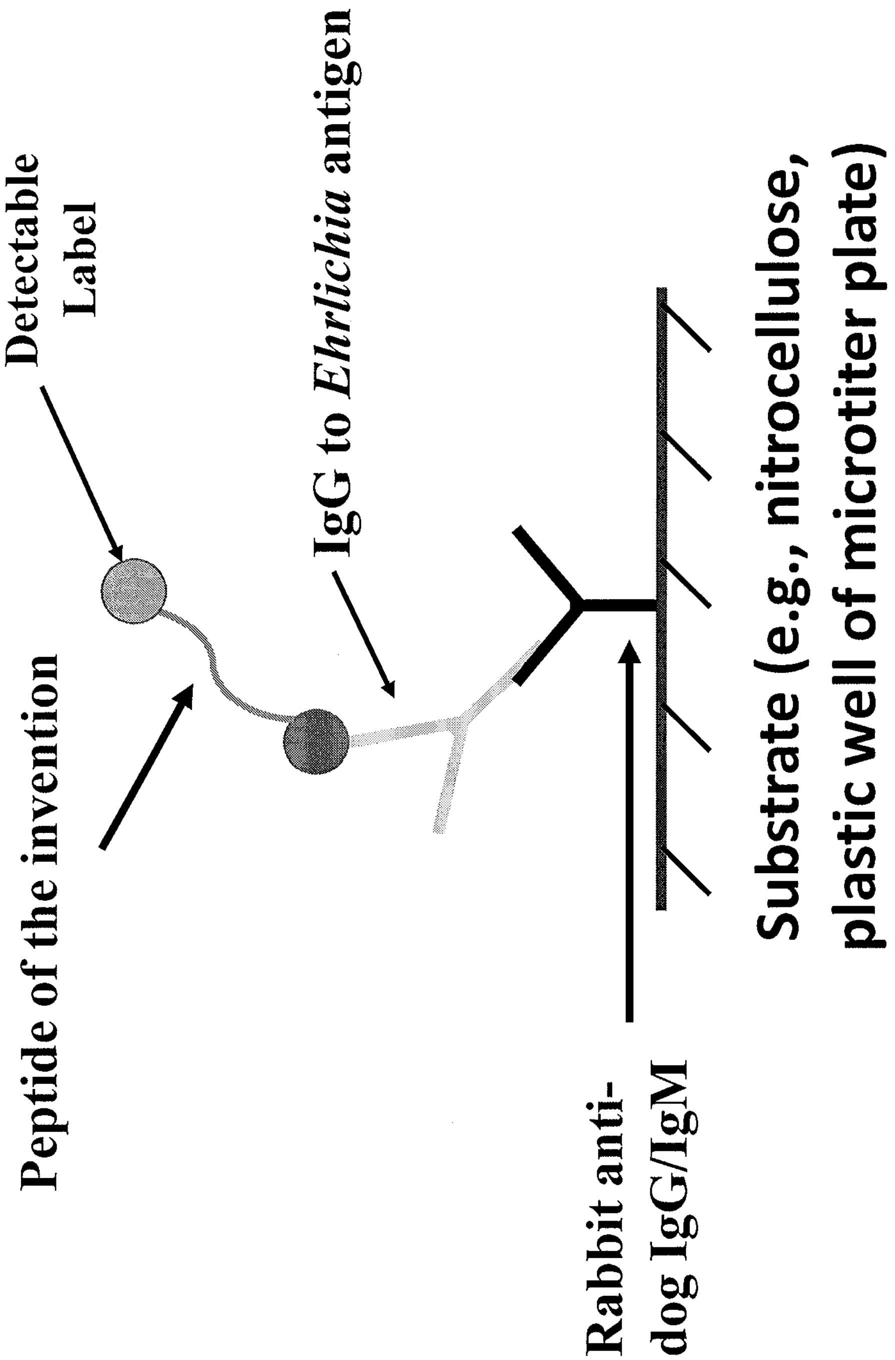
FIG. 2 is a diagram of one type of indirect sandwich assay which can be used to detect antibodies to *Ehrlichia* antigens. In this embodiment, anti-human IgG/IgM, anti-dog IgG/IgM, or anti-cat IgG/IgM antibodies are immobilized to a suitable substrate (e.g., nitrocellulose membrane, well of an ELISA plate) at a test site. Antibodies to *Ehrlichia* antigens in a test sample are bound by the immobilized antibodies. Test sample antibodies to appropriate *Ehrlichia* antigens will then bind to peptides of the invention that are conjugated to a detectable label (e.g., metallic nanoparticle or nanoshell (e.g., colloidal gold), HRP, ALP, fluorophore, colored latex particle).
Figure 3:
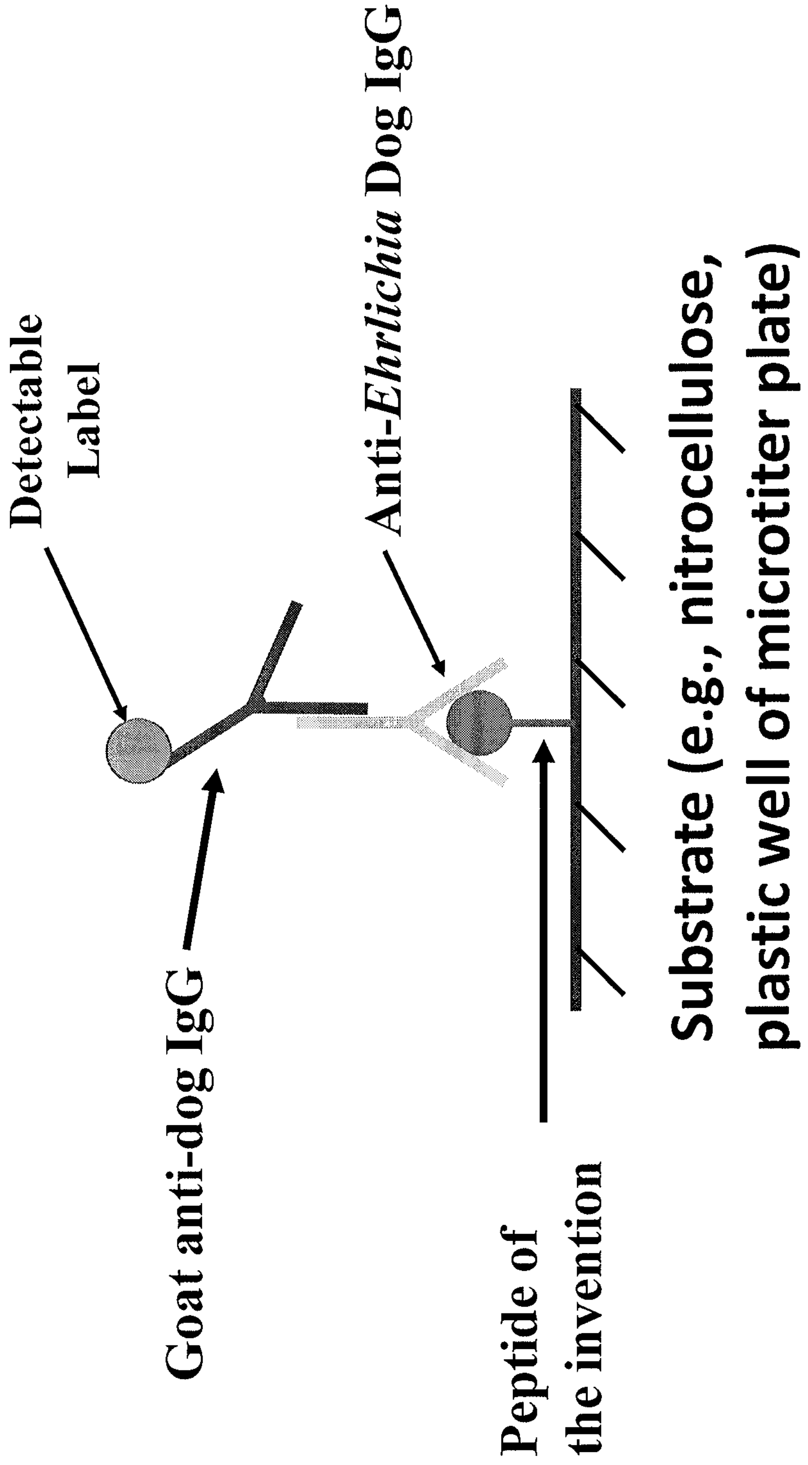
FIG. 3 is a diagram of another type of indirect sandwich assay which can be used to detect antibodies to *Ehrlichia* antigens. In this embodiment, peptides of the invention can be immobilized to a substrate (e.g., nitrocellulose membrane, well of an ELISA plate) to capture anti-*Ehrlichia* antibodies in a test sample. Anti-human IgG/IgM, anti-dog IgG/IgM, or anti-cat IgG/IgM antibodies conjugated to a detectable label (e.g., metallic nanoparticle or nanoshell (e.g., colloidal gold), HRP, ALP, fluorophore, colored latex particle) can be used to detect the presence of the antibodies bound to the immobilized peptides at the test site.
Figure 4:
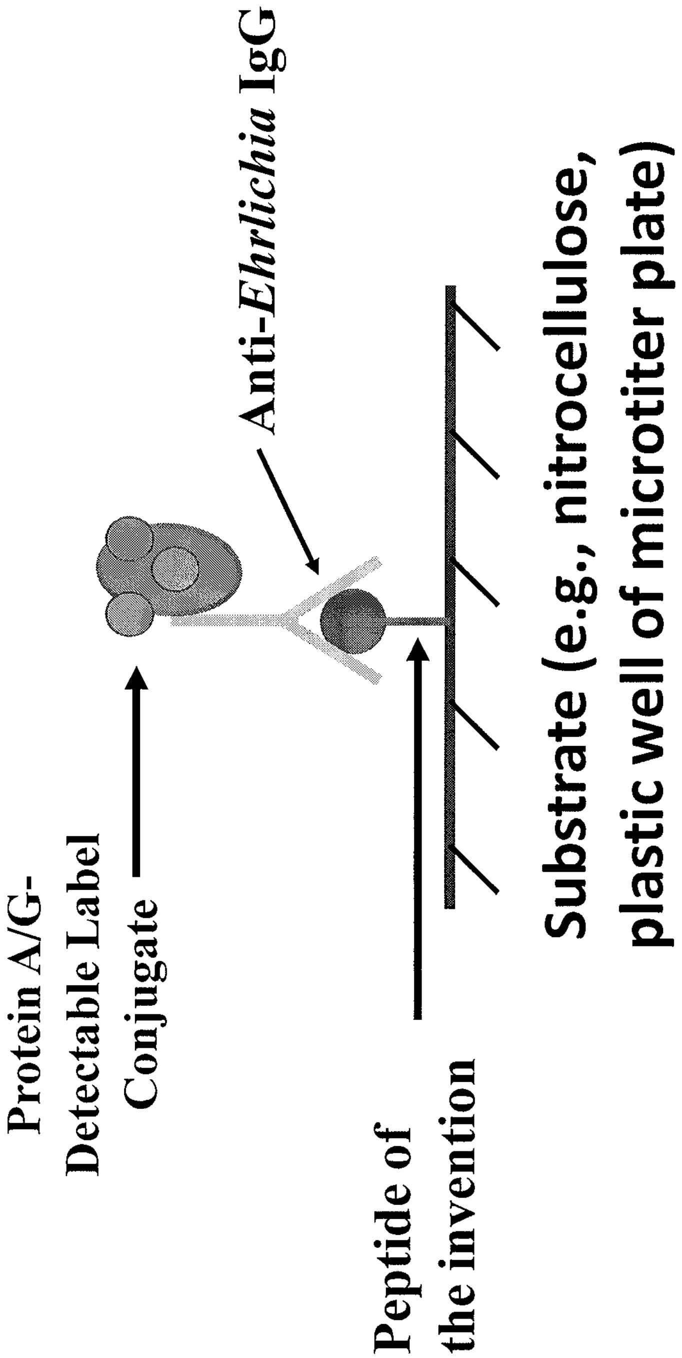
FIG. 4 is a diagram of an immunoassay device which can be used to detect antibodies to *Ehrlichia* antigens. In this embodiment of an immunoassay device, peptides of the invention are immobilized to a suitable substrate (e.g., nitrocellulose membrane, well of an ELISA plate) at a test site. Anti-*Ehrlichia* antibodies in a test sample are bound by the immobilized peptides of the invention. Protein A, Protein G, or a Protein A/G fusion protein conjugated to a detectable label (e.g., metallic nanoparticle or nanoshell (e.g., colloidal gold), HRP, ALP, fluorophore, colored latex particle) is added to the system and binds to the Fc portion of the captured anti-*Ehrlichia* antibody, thereby producing a positive signal. In this embodiment, the device can further comprise a control site at which binding partners that recognize the detectable label-conjugated protein A, detectable label-conjugated protein G, and/or detectable label-conjugated protein A/G fusion are immobilized. Such binding partners may include, but are not limited to, anti-protein A, anti-protein G, mouse IgG, and/or other similar IgG molecules.

In certain embodiments of the invention, the assay comprises: immobilizing the antibody(s) in the sample; adding a peptide of the invention; and detecting the degree of antibody bound to the peptide, e.g., by the peptide being labeled or by adding a labeled substance, such as a labeled binding partner (e.g., streptavidin-HRP or streptavidin-colloidal gold complex) or a labeled antibody which specifically recognizes the peptide. See, e.g., FIG. 2. In other embodiments, the assay comprises: immobilizing a peptide of the invention; adding the sample containing antibodies; and detecting the amount of antibody bound to the peptide, e.g., by adding another peptide of the invention conjugated, directly or indirectly, to a label (e.g., metallic nanoparticle or metallic nanoshell, fluorescent label, enzyme (e.g., horseradish peroxidase or alkaline phosphatase)) or by adding a labeled substance, such as a binding partner or a labeled antibody which specifically recognizes the sample antibodies (e.g., anti-human IgG antibodies, anti-human IgM antibodies, anti-dog IgG antibodies, anti-dog IgM antibodies, anti-cat IgG antibodies, anti-cat IgM antibodies, protein A, protein G, protein A/G fusion proteins, protein L, or combinations thereof, etc.). See, e.g., FIGS. 1, 3, and 4. In other embodiments, the assay comprises: immobilizing a peptide of the invention; adding the sample containing antibodies; and detecting the amount of antibody bound to the peptide, e.g., by adding a first binding partner which specifically recognizes the sample antibodies (e.g., anti-human IgG antibodies, anti-human IgM antibodies, anti-dog IgG antibodies, anti-dog IgM antibodies, anti-cat IgG antibodies, anti-cat IgM antibodies, protein A, protein G, protein A/G fusion proteins, protein L, etc.), and further adding a second binding partner (e.g., protein A, protein G, protein A/G fusion proteins, protein L, etc.), wherein the second binding partner is labeled and recognizes said first binding partner. In still other embodiments, the assay comprises: reacting the peptide and the sample containing antibodies without any of the reactants being immobilized, and then detecting the amount of complexes of antibody and peptide, e.g., by the peptide being labeled or by adding a labeled substance, such as a labeled binding partner (e.g., streptavidin-HRP or streptavidin-colloidal gold complex) or a labeled antibody which specifically recognizes the peptide.

Immobilization of a peptide of the invention can be either covalent or non-covalent, and the non-covalent immobilization can be non-specific (e.g., non-specific binding to a polystyrene surface in, e.g., a microtiter well). Specific or semi-specific binding to a solid or semi-solid carrier, support or surface, can be achieved by the peptide having, associated with it, a moiety which enables its covalent or non-covalent binding to the solid or semi-solid carrier, support or surface. For example, the moiety can have affinity to a component attached to the carrier, support or surface. In this case, the moiety may be, e.g., a biotin or biotinyl group or an analogue thereof bound to an amino acid group of the peptide, such as 6-aminohexanoic acid, and the component is then avidin, streptavidin, neutravidin, or an analogue thereof. An alternative is a situation in which the moiety has the amino acid sequence His-His-His-His-His-His (SEQ ID NO: 82) and the carrier comprises a Nitrilotriacetic Acid (NTA) derivative charged with $Ni^{++}$ or $Co^{++}$ ions. In certain embodiments, the moiety is a fusion partner, e.g., BSA. In exemplary embodiments, peptides of the invention may be conjugated to BSA via N-terminal and/or C-terminal residues of the peptides. In one embodiment, one, two, three, four, five, 10, 15, 20, 25, 30 or more peptides of the invention may be substituted into, e.g., conjugated with BSA. As would be understood by one skilled in the art, substitution levels may impact the sensitivity of the assay. Lower concentrations of highly substituted BSA are needed to achieve sensitivity offered by high concentrations of BSA-peptide containing fewer molecules of peptide. In certain other embodiments, the fusion partner may be MAPS. In certain exemplary embodiments, MAPS may consist of 4, 8, or more asymmetric branches.

Suitable carriers, supports, and surfaces include, but are not limited to, metallic nanolayers, beads (e.g., magnetic beads, colloidal particles or metallic nanoparticles or nanoshells, such as colloidal gold, or particles or nanoparticles comprising silica, latex, polystyrene, polycarbonate, or PDVF), latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles, red blood cells, mono- or polyclonal antibodies or Fab fragments of such antibodies.

The protocols for immunoassays using antigens for detection of specific antibodies are well known in art. For example, a conventional sandwich assay can be used, or a conventional competitive assay format can be used. For a discussion of some suitable types of assays, see Current Protocols in Immunology (supra). In certain embodiments, a peptide of the invention is immobilized on a solid or semi-solid surface or carrier by means of covalent or non-covalent binding, either prior to or after the addition of the sample containing antibody.

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices (e.g., lateral flow immunoassay devices), dipsticks, and immunocapillary or immunochromatographic immunoassay devices.

In embodiments of the invention, the solid or semi-solid surface or carrier is the floor or wall in a microtiter well, a filter surface or membrane (e.g., a nitrocellulose membrane or a PVDF (polyvinylidene fluoride) membrane, such as an Immobilon™ membrane), a hollow fiber, a beaded chromatographic medium (e.g., an agarose or polyacrylamide gel), a magnetic bead, a fibrous cellulose matrix, an HPLC matrix, an FPLC matrix, a substance having molecules of such a size that the molecules with the peptide bound thereto, when dissolved or dispersed in a liquid phase, can be retained by means of a filter, a substance capable of forming micelles or participating in the formation of micelles allowing a liquid phase to be changed or exchanged without entraining the micelles, a water-soluble polymer, or any other suitable carrier, support or surface.

In some embodiments of the invention, the peptide is provided with a suitable label which enables detection. Conventional labels may be used which are capable, alone or in concert with other compositions or compounds, of providing a detectable signal. Suitable labels include, but are not limited to, enzymes (e.g., HRP, beta-galactosidase, alkaline phosphatase, etc.), fluorescent labels, radioactive labels, colored latex particles, and metal-conjugated labels (e.g., metallic nanolayers, metallic nanoparticle- or metallic nanoshell-conjugated labels). Suitable metallic nanoparticle or metallic nanoshell labels include, but are not limited to, gold particles, silver particles, copper particles, platinum particles, cadmium particles, composite particles, gold hollow spheres, gold-coated silica nanoshells, and silica-coated gold shells. Metallic nanolayers suitable for detectable layers include nanolayers comprised of cadmium, zinc, mercury, and noble metals, such as gold, silver, copper, and platinum.

Suitable detection methods include, e.g., detection of an agent which is tagged, directly or indirectly, with a colorimetric assay (e.g., for detection of HRP or beta-galactosidase activity), visual inspection using light microscopy, immunofluorescence microscopy, including confocal microscopy, or by flow cytometry (FACS), autoradiography (e.g., for detection of a radioactively labeled agent), electron microscopy, immunostaining, subcellular fractionation, or the like. In one embodiment, a radioactive element (e.g., a radioactive amino acid) is incorporated directly into a peptide chain; in another embodiment, a fluorescent label is associated with a peptide via biotin/avidin interaction, association with a fluorescein conjugated antibody, or the like. In one embodiment, a detectable specific binding partner for the antibody is added to the mixture. For example, the binding partner can be a detectable secondary antibody or other binding agent (e.g., protein A, protein G, protein L or combinations thereof) which binds to the first antibody. This secondary antibody or other binding agent can be labeled, e.g., with a radioactive, enzymatic, fluorescent, luminescent, metallic nanoparticle or metallic nanoshell (e.g. colloidal gold), or other detectable label, such as an avidin/biotin system. In another embodiment, the binding partner is a peptide of the invention, which can be conjugated directly or indirectly (e.g. via biotin/avidin interaction) to an enzyme, such as horseradish peroxidase or alkaline phosphatase or other signaling moiety. In such embodiments, the detectable signal is produced by adding a substrate of the enzyme that produces a detectable signal, such as a chromogenic, fluorogenic, or chemiluminescent substrate.

A "detection system" for detecting bound peptide, as used herein, may comprise a detectable binding partner, such as an antibody specific for the peptide. In one embodiment, the binding partner is labeled directly. In another embodiment, the binding partner is attached to a signal generating reagent, such as an enzyme that, in the presence of a suitable substrate, can produce a detectable signal. A surface for immobilizing the peptide may optionally accompany the detection system.

In some embodiments of the invention, the detection procedure comprises visibly inspecting the antibody-peptide complex for a color change, or inspecting the antibody-peptide complex for a physical-chemical change. Physical-chemical changes may occur with oxidation reactions or other chemical reactions. They may be detected by eye, using a spectrophotometer, or the like.

A particularly useful assay format is a lateral flow immunoassay format. Antibodies to human or animal (e.g., dog, mouse, deer, etc.) immunoglobulins, or staph A, G, or L proteins, can be labeled with a signal generator or reporter (e.g., colloidal gold) that is dried and placed on a glass fiber pad (sample application pad or conjugate pad). The diagnostic peptide is immobilized on membrane, such as nitrocellulose or a PVDF (polyvinylidene fluoride) membrane (e.g., an Immobilon™ membrane). When a solution of sample (blood, serum, etc.) is applied to the sample application pad (or flows through the conjugate pad), it dissolves the labeled reporter, which then binds to all antibodies in the sample. The resulting complexes are then transported into the next membrane (PVDF or nitrocellulose containing the diagnostic peptide) by capillary action. If antibodies against the diagnostic peptide are present, they bind to the diagnostic peptide striped on the membrane, thereby generating a signal (e.g., a band that can be seen or visualized). An additional antibody specific to the labeled antibody or a second labeled antibody can be used to produce a control signal.

An alternative format for the lateral flow immunoassay comprises the peptides or compositions of the invention being conjugated to a ligand (e.g., biotin) and complexed with labeled ligand receptor (e.g., streptavidin-colloidal gold). The labeled peptide complexes can be placed on the sample application pad or conjugate pad. Anti-human IgG/IgM or anti-animal (e.g., dog, mouse, deer) IgG/IgM antibodies or other peptides of the invention are immobilized on a membrane, such as nitrocellulose of PVDF, at a test site (e.g., a test line). When sample is added to the sample application pad, antibodies in the sample react with the labeled peptide complexes such that antibodies that bind to peptides of the invention become indirectly labeled. The antibodies in the sample are then transported into the next membrane (PVDF or nitrocellulose containing the diagnostic peptide) by capillary action and bind to the immobilized anti-human IgG/IgM or anti-animal IgG/IgM antibodies (or protein A, protein G, protein A/G fusion proteins, protein L, or combinations thereof) or immobilized peptides of the invention. If any of the sample antibodies are bound to the labeled peptides of the invention, the label associated with the peptides can be seen or visualized at the test site. Another embodiment of this type of lateral flow device in which the peptides of the invention are used both as the immobilized capture agent at a test site and as a soluble labeled complex to react with antibodies in a sample is shown in FIG. 1. In such embodiments, to amplify the detection signal, protein A, protein G, and/or protein A/G fusion proteins conjugated to a detectable label (e.g., metallic nanoparticle or nanoshell, HRP, ALP, fluorophore, colored latex particle) may be applied to the test site where they will bind to the Fc region of any antibodies to *Ehrlichia* antigens captured by the immobilized peptides of the invention. Suitable controls for this assay can include, e.g., a chicken IgY-colloidal gold conjugate located at the sample application pad or conjugate pad, and an anti-chicken IgY antibody immobilized at a control site located proximal to the test site.

Another assay for the screening of blood products or other physiological or biological fluids is an enzyme linked immunosorbent assay, i.e., an ELISA. Typically in an ELISA, isolated peptides or mixtures or populations of peptides of the invention are adsorbed to the surface of a microtiter well directly or through a capture matrix (e.g., an antibody). Residual, non-specific protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing specific anti-*Ehrlichia* (e.g., anti-*E. chaffeensis*, anti-*E. muris*, anti-*E. ewingii*, or anti-*E. canis*) antibody. The sample can be applied neat, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with an optimal concentration of an appropriate anti-immunoglobulin antibody (e.g., for human subjects, an anti-human immunoglobulin (αHuIg) from another animal, such as dog, mouse, cow, etc.) or another peptide of the invention that is conjugated to an enzyme or other label by standard procedures and is dissolved in blocking buffer. The label can be chosen from a variety of enzymes, including horseradish peroxidase (HRP), beta-galactosidase, alkaline phosphatase (ALP), glucose oxidase, etc. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length). The cutoff OD value may be defined as the mean OD+3 standard deviations (SDs) of at least 50 serum samples collected from individuals from an area where ehrlichiosis is not endemic, or by other such conventional definitions. In the case of a very specific assay, OD+2 SD can be used as a cutoff value.

In one embodiment of an ELISA, a peptide of the invention is immobilized on a surface, such as a ninety-six-well ELISA plate or equivalent solid phase that is coated with streptavidin or an equivalent biotin-binding compound, such as avidin or neutravidin, at an optimal concentration in an alkaline coating buffer and incubated at 4° C. overnight. After a suitable number of washes with standard washing buffers, an optimal concentration of a biotinylated form of a peptide or composition of the invention, dissolved in a conventional blocking buffer, is applied to each well. A sample is then added, and the assay proceeds as above. Conditions for performing ELISA assays are well-known in the art.

In another embodiment of an ELISA, a peptide or a mixture of peptides of the invention is immobilized on a surface, such as a ninety-six-well ELISA plate or equivalent solid phase via a fusion partner, e.g., BSA or MAPS. A sample is then added and the assay proceeds as above.

An alternative format for the ELISA assay features the peptide(s) of the invention being attached (e.g., fused) to an appropriate enzyme, such as HRP. Steps for carrying out such an ELISA include: coating the wells of a plate with anti-dog, anti-cat, or anti-human IgG/IgM; incubating samples suspected of containing antibodies to the peptide of the invention with the immobilized anti-species IgG/IgM; removing unreacted sample and washing the wells with a suitable wash buffer; applying enzyme-coupled (e.g., HRP-coupled) peptide of the invention and allowing it to react with any captured anti-*Ehrlichia* antibodies; and visualizing the enzyme-coupled peptide by applying an appropriate enzyme substrate (e.g., TMB).

In another embodiment, the methods comprise an agglutination assay. For example, in certain embodiments, metallic nanoparticles or metallic nanoshells (e.g., colloidal gold, etc.) or latex beads are conjugated to peptides or compositions of the invention. Subsequently, the biological fluid is incubated with the bead/peptide conjugate, thereby forming a reaction mixture. The reaction mixture is then analyzed to determine the presence of the antibodies. In certain embodiments, the agglutination assays comprise the use of a second population of particles, such as metallic nanoparticles or metallic nanoshells (e.g., colloidal gold, etc.) or latex beads, conjugated to (1) antibodies specific to the peptides of compositions of the invention, in the case of a competition assay, or (2) antibodies capable of detecting sample antibodies (e.g., anti-human IgG or IgM antibodies, anti-dog IgG or IgM antibodies, anti-cat IgG or IgM antibodies, etc.), in the case of a sandwich assay. Suitable agglutination methods can comprise centrifugation as a means of assessing the extent of agglutination.

In still other embodiments, peptide or compositions of the invention are electro- or dot-blotted onto nitrocellulose paper. Subsequently, a sample, such as a biological fluid (e.g., serum or plasma) is incubated with the blotted antigen, and antibody in the biological fluid is allowed to bind to the antigen(s). The bound antibody can then be detected, e.g., by standard immunoenzymatic methods or by visualization using metallic nanoparticles or nanoshells coupled to secondary antibodies or other antibody binding agents, such as protein A, protein G, protein A/G fusion proteins, protein L, or combinations thereof.

It should be understood by one of skill in the art that any number of conventional protein assay formats, particularly immunoassay formats, may be designed to utilize the isolated peptides of this invention for the detection of *Ehrlichia* antibodies and infection by pathogenic *Ehrlichia* (e.g., *E. chaffeensis, E. muris, E. ewingii*, or *E. canis*) in a subject.

This invention is thus not limited by the selection of the particular assay format, and is believed to encompass assay formats that are known to those of skill in the art.

In certain embodiments, the sample used in the methods is a bodily fluid, such as blood, serum, cerebral spinal fluid, urine, or saliva. In other embodiments, the sample is a tissue (e.g., a tissue homogenate) or a cell lysate. In certain embodiments, the sample is from a wild animal (e.g., a deer or rodent, such as a mouse, chipmunk, squirrel, etc.). In other embodiments, the sample is from a lab animal (e.g., a mouse, rat, guinea pig, rabbit, monkey, primate, etc.). In other embodiments, the sample is from a domesticated or feral animal (e.g., a dog, a cat, a horse). In still other embodiments, the sample is from a human.

Much of the preceding discussion is directed to the detection of antibodies against pathogenic *Ehrlichia*. However, it is to be understood that the discussion also applies to the detection of primed T-cells, either in vitro or in vivo.

It is expected that a cell-mediated immune response (e.g., a T-helper response) is generated, since IgG is produced. It is therefore expected that it will be possible to determine the immunological reactivity between primed T-cells and a peptide of the invention. In vitro this can be done by incubating T-cells isolated from the subject with a peptide of the invention and measuring the immunoreactivity, e.g., by measuring subsequent T-cell proliferation or by measuring release of cytokines from the T-cells, such as IFN-γ. These methods are well-known in the art.

When a method of the invention is carried out in vivo, any of a variety of conventional assays can be used. For example, one can perform an assay in the form of a skin test, e.g., by intradermally injecting, in the subject, a peptide of the invention. A positive skin reaction at the location of injection indicates that the subject has been exposed to and infected with a pathogenic *Ehrlichia* capable of causing monocytic and/or granulocytic ehrlichiosis, and a negative skin response at the location of injection indicates that the subject has not been so exposed/infected. This or other in vivo tests rely on the detection of a T-cell response in the subject.

In another aspect, the invention provides methods of diagnosing monocytic and/or granulocytic ehrlichiosis in a subject. The subject can be a subject suspected of having antibody against a causative agent of monocytic and/or granulocytic ehrlichiosis. The diagnostic method is useful for diagnosing subjects exhibiting the clinical symptoms of monocytic and/or granulocytic ehrlichiosis. Clinical symptoms of human monocytic/granulocytic ehrlichiosis include, but are not limited to, fever, headache, malaise, myalgia, rash, thrombocytopenia, leukopenia, and elevated serum transaminase levels. Clinical symptoms of ehrlichiosis in animals (e.g. canines) include, but are not limited to, fever, petechiae, bleeding disorders, vasculitis, lymphadenopathy, discharge from the nose and eyes, edema of the legs and scrotum, weight loss, pale gums due to anemia, bleeding due to thrombocytopenia, vasculitis, lymphadenopathy, dyspnea, coughing, polyuria, polydipsia, and lameness.

In certain embodiments, the methods comprise contacting a sample from the subject with a peptide of the invention, and detecting formation of an antibody-peptide complex comprising said peptide, wherein formation of said complex is indicative of the subject having ehrlichiosis disease. In certain embodiments, the methods comprise contacting the sample with a mixture or population of two, three, four, or more (e.g., 5, 6, 7, 8, 9, 10, 15, 20, 25, 30, 40, 50, 60, 70, 80, 90, 100, 150, 200, 250, 300, 400, 500, or more) different peptides of the invention. For instance, in one particular embodiment, the methods comprise contacting the sample with a mixture or population of two or more different isolated peptides, wherein each isolated peptide comprises a sequence of SEQ ID NO: 1. In another particular embodiment, the methods comprise contacting the sample with a mixture or population of two or more different isolated peptides, wherein each isolated peptide comprises a sequence of SEQ ID NO: 3. In still another embodiment, the methods comprise contacting the sample with a mixture or population of two or more different isolated peptides, wherein each isolated peptide comprises a sequence of SEQ ID NO: 72. In some embodiments, the methods comprise contacting the sample with a mixture or population of two or more different isolated peptides, wherein each isolated peptide comprises a sequence of SEQ ID NO: 1, SEQ ID NO: 3, or SEQ ID NO: 72. In other embodiments, the methods comprise contacting the sample with a mixture or population of two or more different isolated peptides, wherein each isolated peptide comprises a sequence of SEQ ID NO: 5, SEQ ID NO: 7, SEQ ID NO: 70, SEQ ID NO: 83, or SEQ ID NO: 85.

In certain embodiments, the methods comprise contacting the sample with a mixture of one or more peptides or the invention and one or more other peptides (e.g., an *Ehrlichia* peptide, or antigenic fragment or epitope thereof, such as from an *Ehrlichia* surface protein or an *Ehrlichia* OMP-1, p 38, p 43, p 120, p 140, p 153, p 156, p 200, gp19, gp36, gp47, gp200, or HGE-3 protein. For instance, in some embodiments, the methods comprise contacting the sample with a mixture of one or more peptides of the invention (e.g., SEQ ID NO: 1, SEQ ID NO: 3, SEQ ID NO: 5, SEQ ID NO: 7, SEQ ID NO: 70, SEQ ID NO: 72, SEQ ID NO: 83, or SEQ ID NO: 85) and one or more *Ehrlichia* antigenic peptides having a sequence of SEQ ID NO: 71. In one particular embodiment, the methods comprise contacting the sample with a mixture of one or more peptides having a sequence of SEQ ID NO: 3 and one or more peptides having a sequence of SEQ ID NO: 71. In another embodiment, the methods comprise contacting the sample with a mixture of one or more peptides having a sequence of SEQ ID NO: 72 and one or more peptides having a sequence of SEQ ID NO: 71. In another embodiment, the methods comprise contacting the sample with a mixture of one or more peptides having a sequence of SEQ ID NO: 72 and one or more peptides having a sequence of SEQ ID NO: 3. In one embodiment, the methods comprise contacting the sample with a mixture of one or more peptides having a sequence of SEQ ID NO: 72, one or more peptides having a sequence of SEQ ID NO: 3, and one or more peptides having a sequence of SEQ ID NO: 71.

In certain embodiments, the peptide or each peptide in the mixture or population is an isolated (e.g., synthetic and/or purified) peptide. In certain embodiments, the peptide or mixture of different peptides (i.e. population of peptides) is attached to or immobilized upon a substrate (e.g., a solid or semi-solid support). For example, in certain embodiments, the substrate is a bead (e.g., a colloidal or other type of particle or metallic nanoparticle or nanoshell), a flow path in a lateral flow immunoassay device (e.g., a porous membrane), a flow path in an analytical or centrifugal rotor, a blot (e.g., a Western blot, dot blot, or slot blot), a tube or a well (e.g., in a plate suitable for an ELISA assay), or a sensor (e.g., an electrochemical, optical, or opto-electronic sensor). In some embodiments, the peptide or mixture of peptides is attached to or immobilized upon a solid support through a metallic nanolayer that, in some embodiments, may be comprised of cadmium, zinc, mercury, or a noble metal (e.g., gold, silver, copper, and platinum).

There are a number of different conventional assays for detecting formation of an antibody-peptide complex comprising a peptide of the invention. For example, the detecting step can comprise performing an ELISA assay, performing a lateral flow immunoassay, performing an agglutination assay, performing a wavelength shift assay, analyzing the sample using a Western blot, a slot blot, or a dot blot, analyzing the sample in an analytical or centrifugal rotor, or analyzing the sample with an electrochemical, optical, or opto-electronic sensor. These different assays are described above and/or are well-known to those skilled in the art.

In certain embodiments, the sample is a bodily fluid, such as blood, serum, cerebral spinal fluid, urine, or saliva. In other embodiments, the sample is a tissue (e.g., a tissue homogenate) or a cell lysate. In certain embodiments, the subject is a wild animal (e.g., a deer or rodent, such as a mouse, chipmunk, squirrel, etc.). In other embodiments, the subject is a lab animal (e.g., a mouse, rat, guinea pig, rabbit, monkey, primate, etc.). In other embodiments, the subject is a domesticated or feral animal (e.g., a dog, a cat, a horse). In still other embodiments, the subject is a human.

Kits

In yet another aspect, the invention provides kits. In certain embodiments, the kits comprise a peptide of the invention. In certain embodiments, the kits comprise two, three, four, or more different peptides of the invention or a mixture or population of the peptides of the invention. The peptides can comprise a sequence of SEQ ID NO: 1, SEQ ID NO: 3, SEQ ID NO: 7, SEQ ID NO: 70, SEQ ID NO: 72, SEQ ID NO: 83, SEQ ID NO: 85, or fragments thereof. In certain embodiments, the peptides are attached to or immobilized on a solid support. In some embodiments, the peptides are attached to or immobilized on a solid support through a metallic nanolayer (e.g., cadmium, zinc, mercury, gold, silver, copper, or platinum nanolayer). In certain embodiments, the solid support is a bead (e.g., a colloidal particle or a metallic nanoparticle or nanoshell), a flow path in a lateral flow immunoassay device, a flow path in an analytical or centrifugal rotor, a tube or a well (e.g., in a plate), or a sensor (e.g., an electrochemical, optical, or opto-electronic sensor).

Reagents for particular types of assays can also be provided in kits of the invention. Thus, the kits can include a population of beads (e.g., suitable for an agglutination assay or a lateral flow assay), or a plate (e.g., a plate suitable for an ELISA assay). In other embodiments, the kits comprise a device, such as a lateral flow immunoassay device, an analytical or centrifugal rotor, a Western blot, a dot blot, a slot blot, or an electrochemical, optical, or opto-electronic sensor. The population of beads, the plate, and the devices are useful for performing an immunoassay. For example, they can be useful for detecting formation of an antibody-peptide complex comprising an antibody from a sample and a peptide of the invention. In certain embodiments, a peptide, a mixture of different peptides (i.e. population of peptides) of the invention, or a peptide composition of the invention is attached to or immobilized on the beads, the plate, or the device.

In addition, the kits can include various diluents and buffers, labeled conjugates or other agents for the detection of specifically bound antigens or antibodies (e.g. labeling reagents), and other signal-generating reagents, such as enzyme substrates, cofactors and chromogens. In some embodiments, the kit comprises an anti-human, anti-canine, or anti-feline IgG/IgM antibody conjugated to a detectable label (e.g., a metallic nanoparticle, metallic nanoshell, metallic nanolayer, fluorophore, colored latex particle, or enzyme) as a labeling reagent. In other embodiments, the kit comprises protein A, protein G, protein A/G fusion proteins, protein L, or combinations thereof conjugated to a detectable label (e.g., a metallic nanoparticle, metallic nanoshell, metallic nanolayer, fluorophore, colored latex particle, or enzyme) as a labeling reagent. An exemplary protein A/G fusion protein combines four Fc-binding domains from protein A with two from protein G. See, e.g., Sikkema, J. W. D., Amer. Biotech. Lab, 7:42, 1989 and Eliasson et al., J. Biol. Chem. 263, 4323-4327, 1988, both which are hereby incorporated by reference in their entireties. In still other embodiments, the labeling reagents of the kit are a second population of peptides of the invention conjugated to a detectable label (e.g., a metallic nanoparticle, metallic nanoshell, metallic nanolayer, fluorophore, colored latex particle, or enzyme). The second population of peptides can be the same as or different than the first population of peptides, which may optionally be attached to or immobilized upon a solid support.

Other components of a kit can easily be determined by one of skill in the art. Such components may include coating reagents, polyclonal or monoclonal capture antibodies specific for a peptide of the invention, or a cocktail of two or more of the antibodies, purified or semi-purified extracts of these antigens as standards, monoclonal antibody detector antibodies, an anti-mouse, anti-dog, anti-cat, anti-chicken, or anti-human antibody conjugated to a detectable label, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptide-antibody complex.

Such kits provide a convenient, efficient way for a clinical laboratory to diagnose infection by a pathogenic *Ehrlichia*, such as *E. chaffeensis, E. muris, E. ewingii*, or *E. canis*. Thus, in certain embodiments, the kits further comprise an instruction. For example, in certain embodiments, the kits comprise an instruction indicating how to use a peptide or population of peptides of the invention to detect an antibody to one or more *Ehrlichia* antigens or to diagnose monocytic and/or granulocytic ehrlichiosis. In certain embodiments, the kits comprise an instruction indicating how to use a population of beads, a plate, or a device (e.g., comprising a peptide or a mixture of different peptides of the invention) to detect an antibody to one or more *Ehrlichia* antigens or to diagnose monocytic and/or granulocytic ehrlichiosis.

The peptides, compositions and devices comprising the peptides, kits and methods of the invention offer a number of advantages. For example, they allow for simple, inexpensive, rapid, sensitive and accurate detection of monocytic and/or granulocytic ehrlichiosis, and avoid serologic cross-reactivity with other conditions with similar symptoms. This allows for an accurate diagnosis. Furthermore, a diagnostic test of the invention (e.g., an ELISA assay, lateral flow immunoassay, or agglutination assay) is useful in serum samples that contain anti-OMP-1 antibodies or other antibodies produced in response to a vaccine based on the outer surface proteins of *Ehrlichia.*

The following examples illustrate various aspects of the invention. The examples should, of course, be understood to be merely illustrative of only certain embodiments of the invention and not to constitute limitations upon the scope of the invention.

EXAMPLES

Example 1—ELISA Assay

Three different populations of peptides were synthesized using standard synthesis procedures. Each peptide in the first population of peptides (ECHEW1) contained a sequence of SEQ ID NO: 72. The first population of peptides specifically binds to antibodies elicited by multiple *Ehrlichia* spp. (e.g., *canis, chaffeensis*, and *ewingii*). Each peptide in the second population of peptides (EE12EW1) contained a sequence of SEQ ID NO: 3. The second population of peptides specifically binds to antibodies elicited primarily by *E. canis* and *E. chaffeensis* with some cross-reactivity to *E. ewingii*. Each peptide in the third population of peptides (EE13) contained a sequence of SEQ ID NO: 71. The third population of peptides specifically binds to antibodies elicited primarily by *E. ewingii* with some cross-reactivity to *E. canis* and *E. chaffeensis*.

Each peptide in the three populations was linked separately to the carrier protein bovine serum albumin (BSA) using thio-ether chemistry. The resulting BSA-peptide conjugates were used as capture entities in 96-well ELISA plates to create three separate ELISA assays (one population of peptides per plate). The plates were then blocked to prevent undesirable non-specific binding.

Dog plasma samples positive to *Ehrlichia* species, as determined by indirect immunofluorescence assays (IFA), IDEXX SNAP 4DX Plus, and/or SNAP 3Dx, were incubated with the immobilized capture peptides in each of the three ELISA plates. After one hour incubation, the unreacted materials were removed by washing the micro wells. The specifically captured dog IgG or IgM were detected by reaction with HRP-labeled Protein A. HRP was assayed using a commercial TMB substrate. The optical density of each well was read at 650 nm with a plate reader.

A total of 156 samples were evaluated, of which 152 tested positive in the ELISA plates with four samples testing negative. Thus, the percent sensitivity of the test was 97.4%. A summary of the results separated by infective *Ehrlichia* species is shown in Table 1 below. These experimental results show that populations of peptides defined by SEQ ID NO: 72, SEQ ID NO: 3, or SEQ ID NO: 71 have a high degree of sensitivity in detecting the presence of antibodies to antigens from various *Ehrlichia* spp.

TABLE 1

ELISA Results of Known *Ehrlichia*-Positive Samples

| | Positive by ELISA | Negative by ELISA | Total |
|---|---|---|---|
| No. of *E. canis*-positive samples[1] | 44 | 1 | 45 |
| No. of *E. chaffeensis*-positive samples[2] | 38 | 2 | 40 |
| No. of *E. ewingii*-positive samples[3] | 46 | 1 | 47 |
| No. of positive samples; indeterminate species[4] | 24 | 0 | 24 |
| Total Samples Tested | 156 | | |
| Total No. of Positive Samples Correctly Identified (detected positive by ELISA) | 152 | | |
| Total No. of Positive Samples Incorrectly Identified (detected negative by ELISA) | 4 | | |
| % Sensitivity | 97.4 | | |

[1]These samples tested positive in the ELISA assays with ECHEW1 (SEQ ID NO: 72) and EE12EW1 (SEQ ID NO: 3) populations of peptides and had a higher titer for *E. canis* by IFA.
[2]These samples tested positive in the ELISA assays with ECHEW1 (SEQ ID NO: 72) and EE12EW1 (SEQ ID NO: 3) populations of peptides and had a higher titer for *E. chaffeensis* by IFA.
[3]These samples tested positive in the ELISA assays with ECHEW1 (SEQ ID NO: 72) and EE13 (SEQ ID NO: 71) populations of peptides.
[4]The species of *Ehrlichia* in these samples could not be determined conclusively by IFA or the SNAP assays, but the samples tested positive in the ELISA assay with ECHEW1 (SEQ ID NO: 72).

Example 2—Lateral Flow Assay

Figure 5:
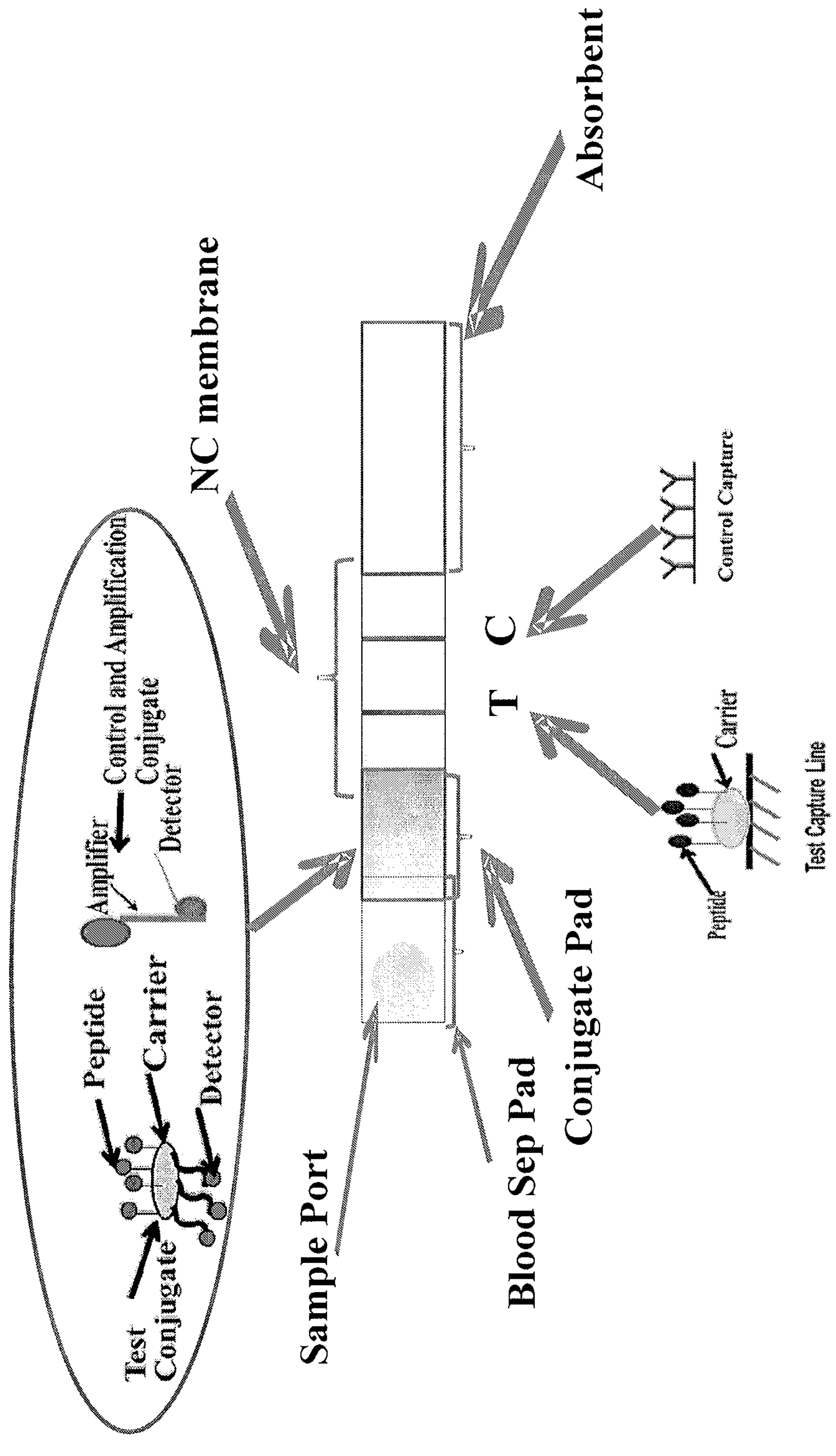
FIG. 5 depicts one example of a lateral flow assay device that can be used to detect antibodies to *Ehrlichia* antigens. Peptides of the invention are linked to a carrier protein (e.g. bovine serum albumin) and the resulting BSA-peptide conjugates are immobilized on a nitrocellulose (NC) membrane at a test site (T). The same BSA-peptide conjugates are conjugated to a detectable label (e.g., colloidal gold) and deposited in a conjugate pad positioned upstream of the test site. Gold-conjugated protein A and gold-conjugated protein G (i.e. amplifier) is added to the conjugate pad to enhance the signal by binding to the Fc portion of the captured anti-*Ehrlichia* antibody. The device further comprises a control site (C) at which binding partners that recognize the gold-conjugated protein A and/or gold-conjugated protein G are immobilized.

A lateral flow immunoassay in a double antigen sandwich format was constructed to detect the presence of antibodies specific for *Ehrlichia* antigens from multiple species. A population of peptides defined by SEQ ID NO: 72 was linked to BSA and the resulting complexes were used both as test conjugate (peptides labeled with gold nanoparticles) and as capture (immobilized at the test line of the device). The signal produced at the test line was enhanced by Protein A and Protein G-gold conjugates added to the labeled peptide conjugate. The device is depicted in FIG. 5.

To conduct the assay, one drop of anti-coagulated whole blood, serum, or plasma is applied to the sample port of the device. The blood separation pad filters blood cells from whole blood. Plasma (or serum) mobilizes and binds specifically to the test conjugate present on the conjugate pad and any formed antibody-peptide complexes migrate to the nitrocellulose membrane containing the test and the control regions. The application of a chase buffer after sample application moves the free and the bound test conjugates through the nitrocellulose membrane towards the upper absorbent pad. The labeled peptide-antibody complexes move to the test line where immobilized peptides capture labeled peptide-antibody complexes via the second binding sites on the antibodies. Protein A-gold and Protein G-gold conjugates in the conjugate mixture bind to captured antibodies amplifying the detection signal. The appearance of one red line at the test site and a second red line at the control site indicates the presence of antibodies to *Ehrlichia* spp. (e.g., *canis, chaffeensis*, or *ewingii*) in the sample. The appearance of a red line at only the control site indicates the absence of antibodies to all of the *Ehrlichia* spp. in the sample. The test is considered invalid if (i) a signal at the test line appears but no signal at the control line is present or (ii) no signal is observed at either the control or test lines.

The same 156 known *Ehrlichia*-positive dog plasma samples evaluated by ELISA assay in Example 1 were tested in the lateral flow device. In addition, 120 dog samples (100 plasma and 20 whole blood samples) that were determined to be negative by indirect immunofluorescence assays or IDEXX SNAP 4DX Plus", were also evaluated. The results are summarized in Table 2 below. The lateral flow assay had a sensitivity of 97.4% with a 95% confidence interval of 93.6-99.3%. The specificity of the assay was 98.3% with a 95% confidence interval of 94.1-99.8%. This example demonstrates that a population of peptides defined by SEQ ID NO: 72 can effectively detect antibodies against *Ehrlichia* antigens when employed in a lateral assay format.

TABLE 2

| Lateral Flow Assay Results of Known *Ehrlichia*-Positive and Negative Samples | | |
|---|---|---|
| | Negative by Lateral Flow | Positive by Lateral Flow |
| No. of known negative samples | 118 | 2 |
| No. of known positive samples | 4 | 152 |

Example 3—Indirect Fluorescent Antibody Assay

An indirect fluorescent antibody test is constructed using latex beads coated with one or more peptides of the invention. In certain embodiments, the peptides defined by SEQ ID NO: 71, SEQ ID NO: 72, SEQ ID NO: 3, or SEQ ID NO: 5 are used. The peptides of the invention are coated onto maleimide-derivatized latex beads using thio-ether chemistry. Alternatively, the peptides of the invention may be conjugated to BSA via thio-ether or similar chemistries and are passively absorbed on to latex beads. A population of such beads is then immobilized on a glass slide using known techniques.

To conduct the assay, one drop of serum or plasma (diluted appropriately with a suitable buffer) from dogs suspected of having anti-*Ehrlichia* antibodies, is applied to the glass slide coated with latex beads. Following a suitable incubation time, the unreacted materials are washed away and a drop of fluorescently labeled anti-dog IgG (or IgM) is applied and the slides are incubated for an additional time period. The final preparation is viewed under a fluorescent microscope to determine fluorescently tagged latex beads. The classification of the test serum/plasma as positive or negative is based on comparison with appropriate controls. An enzyme label may be used in place of the fluorescent label in which case the visualization step employs an enzyme substrate. For example, anti-dog IgG/IgM labeled with alkaline phosphatase can be visualized by exposing the slide to a BCIP-nitro BT substrate. Labeled Protein A, Protein G, or Protein A/G fusion can be used in place of labeled anti-dog IgG and anti-dog IgM to detect antibodies bound to the peptide-coated beads.

To the extent that any definitions in documents incorporated by reference are inconsistent with the definitions provided herein, the definitions provided herein are controlling. Although the invention has been described with reference to the presently preferred embodiments, it should be understood that various changes and modifications, as would be obvious to one skilled in the art, can be made without departing from the spirit of the invention. Accordingly, the invention is limited only by the following claims.

The disclosures, including the claims, figures and/or drawings, of each and every patent, patent application, and publication cited herein are hereby incorporated herein by reference in their entireties.

What is claimed:

1. A population of isolated peptides comprising two or more different peptides, the population of peptides comprising:

(i) one or more peptides comprising the sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-E-T R-$X_{44}$-T-F-G-L-$X_{49}$-K-Q-Y-D-G-A-$X_{56}$-I-$X_{58}$-E-N-Q-V-Q-N-K-F-T-I-S-N-C(SEQ ID NO:72) or fragment thereof comprising at least 20 contiguous amino acids of SEQ ID NO: 72, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{44}$ is any amino acid, $X_{49}$ is any amino acid, $X_{56}$ is any amino acid, and $X_{58}$ is any amino acid, (ii) one or more peptides comprising the sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-$X_{41}$-T-R-$X_{44}$-T-F-G-$X_{48}$-$X_{49}$-K-Q-Y-D-G-A-$X_{56}$-I-$X_{58}$-E-N-Q-V-Q-N-K-F-T-I-S-N-C (SEQ ID NO: 3) or a fragment thereof comprising at least 20 contiguous amino acids of SEQ ID NO: 3, wherein $X_2$ is an amino acid selected from the group consisting of A and V, $X_5$ is an amino acid selected from the group consisting of E and D, $X_7$ is any amino acid, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ in SEQ ID NOs: 72 and is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{41}$ is an amino acid selected from the group consisting of D and N, $X_{44}$ is any amino acid, $X_{48}$ is an amino acid selected from the group consisting of V and A, $X_{49}$ is any amino acid, $X_{56}$ is any amino acid, and $X_{58}$ is any amino acid, (iii) one or more peptides comprising the sequence of F-S-A-K-E-E-$X_7$-A-E-T-R-$X_{12}$-T-F-G-L-$X_{17}$-K-Q-Y-D-G-A-$X_{24}$-I-$X_{26}$-E-N-Q-V-Q-N-K-F-T-I-S-N-C(SEQ ID NO: 71) or a fragment thereof comprising at least 20 contiguous amino acids of SEQ ID NO: 71, wherein $X_7$ is any amino acid, $X_{12}$ is any amino acid, $X_{17}$ is any amino acid, $X_{24}$ is any amino acid, and $X_{26}$ is any amino acid, or (iv) one or more peptides from each of (i) and (ii), one or more peptides from each of (i) and (iii), one or more peptides from each of (ii) and (iii), or one or more peptides from each of (i), (ii), and (iii).

2. The population of isolated peptides of claim 1, wherein the population comprises a peptide according to (i), wherein $X_{39}$ of SEQ ID NO: 72 is K; $X_{44}$ of SEQ ID NO: 72 is selected from the group consisting of K and R; $X_{49}$ of SEQ ID NO: 72 is selected from the group consisting of E and D; $X_{56}$ of SEQ ID NO: 72 is selected from the group consisting of K and Q; and $X_{58}$ of SEQ ID NO: 72 is selected from the group consisting of E and T.

3. The population of isolated peptides of claim 1, wherein the population comprises a peptide according to (ii), wherein $X_{39}$ of SEQ ID NO: 3 is K; $X_{44}$ of SEQ ID NO: 3 is selected from the group consisting of K and R; $X_{49}$ of SEQ ID NO: 3 is selected from the group consisting of E and D; $X_{56}$ of SEQ ID NO: 3 is selected from the group consisting of K and Q; and $X_{58}$ of SEQ ID NO: 3 is selected from the group consisting of E and T.

4. The population of isolated peptides of claim 1, wherein the population comprises a peptide according to (iii), wherein $X_7$ of SEQ ID NO: 71 is K; $X_{12}$ of SEQ ID NO: 71 is selected from the group consisting of K and R; $X_{17}$ of SEQ ID NO: 71 is selected from the group consisting of E and D; $X_{24}$ of SEQ ID NO: 71 is selected from the group consisting of K and Q; and $X_{26}$ of SEQ ID NO: 71 is selected from the group consisting of E and T.

5. The population of isolated peptides of claim 1, comprising three or more different peptides.

6. The population of isolated peptides of claim 1, wherein the fragment comprising at least 20 contiguous amino acids of SEQ ID NO 72, 3, or 71 comprises a cysteine residue at the carboxyl terminus of the peptide.

7. The population of isolated peptides of claim 1, wherein the fragment comprising at least 20 contiguous amino acids of SEQ ID NO 72, 3, or 71 further comprises a cysteine residue at the amino terminus of the peptide.

8. The population of isolated peptides of claim 1, wherein the fragment comprises at least 25, 30, or 35 contiguous amino acids of SEQ ID NO: 72, 3, or 71.

9. The population of isolated peptides of claim 1, wherein one or more peptides comprises an additional N-terminal peptide sequence that is a native OMP-1 sequence or non-OMP-1 *Ehrlichia* antigen.

10. The population of isolated peptides of claim 1, wherein one or more peptides comprises an additional C-terminal peptide sequence that is a native OMP-1 sequence or non-OMP-1 *Ehrlichia* antigen.

11. The population of isolated peptides of claim 1, wherein one or more peptides is conjugated to a ligand or is biotinylated.

12. The population of isolated peptides of claim 1, wherein one or more peptides is conjugated to avidin, streptavidin, neutravidin, serum albumin, keyhole limpet hemocyanin (KLH), an enzyme, a metallic nanoparticle, or a nanoshell.

13. The population of isolated peptides of claim 1, wherein one or more peptides is conjugated to bovine serum albumin.

14. The population of isolated peptides of claim 1, comprising at least one peptide of (i), at least one peptide of (ii), and at least one peptide of (iii); wherein each peptide in the population is conjugated to bovine serum albumin.

15. The population of isolated peptides of claim 1, wherein the peptides are immobilized to a solid support optionally through a metallic nanolayer.

16. The population of isolated peptides of claim 15, wherein the solid support is a plurality of beads, a flow path in a lateral flow immunoassay device, a well in a microtiter plate, or a flow path in a rotor.

17. A population of isolated peptides comprising (i) one or more peptides comprising the sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-E-T-R-$X_{44}$-T-F-G-L-$X_{49}$-K-Q-Y-D-G-A-$X_{56}$-I-$X_{58}$-E-N-Q-V-Q-N-K-F-T-I-S-N-C(SEQ ID NO:72) or fragment thereof comprising at least 20 contiguous amino acids of SEQ ID NO: 72, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{44}$ is any amino acid, $X_{49}$ is any amino acid, $X_{56}$ is any amino acid, and $X_{58}$ is any amino acid, (ii) one or more peptides comprising the sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-$X_{41}$-T-R-$X_{44}$-T-F-G-$X_{48}$-$X_{49}$-K-Q-Y-D-G-A-$X_{56}$-I-$X_{58}$-E-N-Q-V-Q-N-K-F-T-I-S-N-C (SEQ ID NO: 3) or a fragment thereof comprising at least 20 contiguous amino acids of SEQ ID NO: 3, wherein $X_2$ is an amino acid selected from the group consisting of A and V, $X_5$ is an amino acid selected from the group consisting of E and D, $X_7$ is any amino acid, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ in SEQ ID NOs: 72 and is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{41}$ is an amino acid selected from the group consisting of D and N, $X_{44}$ is any amino acid, $X_{48}$ is an amino acid selected from the group consisting of V and A, $X_{49}$ is any amino acid, $X_{56}$ is any amino acid, and $X_{58}$ is any amino acid, and (iii) one or more peptides comprising the sequence of F-S-A-K-E-E-$X_7$-A-E-T-R-$X_{12}$-T-F-G-L-$X_{17}$-K-Q-Y-D-G-A-$X_{24}$-I-$X_{26}$-E-N-Q-V-Q-N-K-F-T-I-S-N-C(SEQ ID NO: 71) or a fragment thereof comprising at least 20 contiguous amino acids of SEQ ID NO: 71, wherein $X_7$ is any amino acid, $X_{12}$ is any amino acid, $X_{17}$ is any amino acid, $X_{24}$ is any amino acid, and $X_{26}$ is any amino acid.

18. A method for detecting in a sample an antibody to an epitope of an *Ehrlichia* antigen, the method comprising:

contacting a sample with the population of isolated peptides of claim 1; and detecting formation of an antibody-peptide complex comprising one or more peptides in the population, wherein formation of said complex is indicative of an antibody to an epitope of an *Ehrlichia* antigen being present in said sample.

19. The method of claim 18, wherein said *Ehrlichia* antigen is from an *Ehrlichia chaffeensis, Ehrlichia ewingii, Ehrlichia canis*, or *Ehrlichia muris* species.

20. The method of claim 18, wherein said detecting step comprises (i) performing an ELISA assay, (ii) running a lateral flow assay, (iii) performing an agglutination assay, (iv) performing a Western blot, a slot blot, or dot blot, (v) performing a wavelength shift assay, or (vi) running the sample through an analytical or centrifugal rotor.

21. The method of claim 18, wherein said sample is from a human, canine, or feline subject.

22. The method of claim 18, wherein said sample is a blood, serum, plasma, cerebral spinal fluid, tissue extract, urine, or saliva sample.

23. The method of claim 18, wherein the formation of a plurality of antibody-peptide complexes are detected, and wherein formation of said complexes is indicative of antibodies to epitopes of *Ehrlichia* antigens from multiple *Ehrlichia* species being present in said sample.

24. A method for diagnosing monocytic and/or granulocytic ehrlichiosis in a subject, the method comprising:

contacting a sample from the subject with the population of isolated peptides of claim 1; and detecting formation of an antibody-peptide complex comprising one or more peptides in the population, wherein formation of the complex is indicative the subject having monocytic and/or granulocytic ehrlichiosis.

25. A kit comprising the population of isolated peptides of claim 1 and a labeling reagent capable of binding to an antibody that recognizes an epitope of one or more peptides in the population.

26. The kit of claim 25, wherein the population of isolated peptides comprises (i) one or more peptides comprising the sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$G-G-G-G-G-N-F-S-A-K-E-E-$X_{39}$-A-E-T-R-$X_{44}$-T-F-G-L-$X_{49}$-K-Q-Y-D-G-A-$X_{56}$-I-$X_{58}$-E-N-Q-V-Q-N-K-F-T-I-S-N-C(SEQ ID NO:72) or fragment thereof comprising at least 20 contiguous amino acids of SEQ ID NO: 72, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{44}$ is any amino acid, $X_{49}$ is any amino acid, $X_{56}$ is any amino acid, and $X_{58}$ is any amino acid, (ii) one or more peptides comprising the sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$A-$X_{41}$-T-R-$X_{44}$-T-F-G-$X_{48}$-$X_{49}$-K-Q-Y-D-G-A-$X_{56}$-I-$X_{58}$-E-N-Q-V-Q-N-K-F-T-I-S-N-C (SEQ ID NO: 3) or a fragment thereof comprising at least 20 contiguous amino acids of SEQ ID NO: 3, wherein $X_2$ is an amino acid selected from the group consisting of A and V, $X_5$ is an amino acid selected from the group consisting of E and D, $X_7$ is any amino acid, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ in SEQ ID NOs: 72 and is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{41}$ is an amino acid selected from the group consisting of D and N, $X_{44}$ is any amino acid, $X_{48}$ is an amino acid selected from the group consisting of V and A, $X_{49}$ is any amino acid, $X_{56}$ is any amino acid, and $X_{58}$ is any amino acid, and (iii) one or more peptides comprising the sequence of F-S-A-K-E-E-$X_7$-A-E-T-R-$X_{12}$-T-F-G-L-$X_{17}$-K-Q-Y-D-G-A-$X_{24}$-I-$X_{26}$-E-N-Q-V-Q-N-K-F-T-I-S-N-C(SEQ ID NO: 71) or a fragment thereof comprising at least 20 contiguous amino acids of SEQ ID NO: 71, wherein $X_7$ is any amino acid, $X_{12}$ is any amino acid, $X_{17}$ is any amino acid, $X_{24}$ is any amino acid, and $X_{26}$ is any amino acid.

* * * * *

SEQUENCE LISTING

```
<160> NUMBER OF SEQ ID NOS: 86

<210> SEQ ID NO 1
<211> LENGTH: 40
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (2)..(2)
<223> OTHER INFORMATION: Xaa can be Ala or Val
<220> FEATURE:
<221> NAME/KEY: misc_feature
<222> LOCATION: (10)..(10)
<223> OTHER INFORMATION: Xaa can be Thr or Val
<220> FEATURE:
<221> NAME/KEY: misc_feature
<222> LOCATION: (11)..(11)
<223> OTHER INFORMATION: Xaa can be Gly or Ala
<220> FEATURE:
<221> NAME/KEY: misc_feature
<222> LOCATION: (18)..(18)
<223> OTHER INFORMATION: Xaa can be Glu or Gln
<220> FEATURE:
<221> NAME/KEY: misc_feature
<222> LOCATION: (20)..(20)
<223> OTHER INFORMATION: Xaa can be Asp or Asn
<220> FEATURE:
<221> NAME/KEY: misc_feature
<222> LOCATION: (22)..(22)
<223> OTHER INFORMATION: Xaa can be Ser or Val
<220> FEATURE:
<221> NAME/KEY: misc_feature
<222> LOCATION: (24)..(24)
<223> OTHER INFORMATION: Xaa can be Ala or Ile
<220> FEATURE:
<221> NAME/KEY: misc_feature
<222> LOCATION: (25)..(25)
<223> OTHER INFORMATION: Xaa can be Thr or Pro
<220> FEATURE:
```

<221> NAME/KEY: misc_feature
<222> LOCATION: (26)..(26)
<223> OTHER INFORMATION: Xaa can be Ser, Asn or Lys
<220> FEATURE:
<221> NAME/KEY: misc_feature
<222> LOCATION: (27)..(27)
<223> OTHER INFORMATION: Xaa can be any amino acid except His, Asn, Ser or Ala
<220> FEATURE:
<221> NAME/KEY: misc_feature
<222> LOCATION: (28)..(28)
<223> OTHER INFORMATION: Xaa can be any amino acid except Ala, Ser or Pro
<220> FEATURE:
<221> NAME/KEY: misc_feature
<222> LOCATION: (29)..(29)
<223> OTHER INFORMATION: Xaa can be any amino acid except Asp, Pro, Asn or Ser
<220> FEATURE:
<221> NAME/KEY: misc_feature
<222> LOCATION: (30)..(30)
<223> OTHER INFORMATION: Xaa can be any amino acid except Ala, Glu, Asp or Ser
<220> FEATURE:
<221> NAME/KEY: misc_feature
<222> LOCATION: (31)..(31)
<223> OTHER INFORMATION: Xaa can be any amino acid except Asp, Asn, Val or His
<220> FEATURE:
<221> NAME/KEY: misc_feature
<222> LOCATION: (32)..(32)
<223> OTHER INFORMATION: Xaa can be any amino acid except Phe or Thr
<220> FEATURE:
<221> NAME/KEY: misc_feature
<222> LOCATION: (33)..(33)
<223> OTHER INFORMATION: Xaa can be any amino acid except Asn, Phe or Ile
<220> FEATURE:
<221> NAME/KEY: misc_feature
<222> LOCATION: (34)..(34)
<223> OTHER INFORMATION: Xaa can be any amino acid except Asn, Thr or Asp
<220> FEATURE:
<221> NAME/KEY: misc_feature
<222> LOCATION: (35)..(35)
<223> OTHER INFORMATION: Xaa can be any amino acid except Lys, Val or Pro
<220> FEATURE:
<221> NAME/KEY: misc_feature
<222> LOCATION: (36)..(36)
<223> OTHER INFORMATION: Xaa can be any amino acid except Gly, Pro or Ser
<220> FEATURE:
<221> NAME/KEY: misc_feature
<222> LOCATION: (37)..(37)
<223> OTHER INFORMATION: Xaa can be any amino acid except Tyr, Asn or Thr
<220> FEATURE:
<221> NAME/KEY: misc_feature
<222> LOCATION: (38)..(38)
<223> OTHER INFORMATION: Xaa can be any amino acid except Ser, Tyr or Ile
<220> FEATURE:
<221> NAME/KEY: misc_feature
<222> LOCATION: (39)..(39)
<223> OTHER INFORMATION: Xaa can be any amino acid except Phe or Ser

<400> SEQUENCE: 1

```
Ser Xaa Lys Glu Asp Lys Gln Thr Thr Xaa Xaa Ile Trp Gly Leu Lys
1               5                   10                  15

Gln Xaa Trp Xaa Gly Xaa Pro Xaa Xaa Xaa Xaa Xaa Xaa Xaa Xaa Xaa
            20                  25                  30

Xaa Xaa Xaa Xaa Xaa Xaa Xaa Cys
        35                  40
```

<210> SEQ ID NO 2
<211> LENGTH: 40
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (3)..(3)
<223> OTHER INFORMATION: Xaa can be Ala or Val
<220> FEATURE:
<221> NAME/KEY: misc_feature
<222> LOCATION: (11)..(11)
<223> OTHER INFORMATION: Xaa can be Thr or Val
<220> FEATURE:
<221> NAME/KEY: misc_feature
<222> LOCATION: (12)..(12)
<223> OTHER INFORMATION: Xaa can be Gly or Ala
<220> FEATURE:
<221> NAME/KEY: misc_feature
<222> LOCATION: (19)..(19)
<223> OTHER INFORMATION: Xaa can be Glu or Gln
<220> FEATURE:
<221> NAME/KEY: misc_feature
<222> LOCATION: (21)..(21)
<223> OTHER INFORMATION: Xaa can be Asp or Asn
<220> FEATURE:
<221> NAME/KEY: misc_feature
<222> LOCATION: (23)..(23)
<223> OTHER INFORMATION: Xaa can be Ser or Val
<220> FEATURE:
<221> NAME/KEY: misc_feature
<222> LOCATION: (25)..(25)
<223> OTHER INFORMATION: Xaa can be Ala or Ile
<220> FEATURE:
<221> NAME/KEY: misc_feature
<222> LOCATION: (26)..(26)
<223> OTHER INFORMATION: Xaa can be Thr or Pro,
<220> FEATURE:
<221> NAME/KEY: misc_feature
<222> LOCATION: (27)..(27)
<223> OTHER INFORMATION: Xaa can be Ser, Asn or Lys
<220> FEATURE:
<221> NAME/KEY: misc_feature
<222> LOCATION: (28)..(28)
<223> OTHER INFORMATION: Xaa can be any amino acid except His, Asn, Ser or Ala
<220> FEATURE:
<221> NAME/KEY: misc_feature
<222> LOCATION: (29)..(29)
<223> OTHER INFORMATION: Xaa can be any amino acid except Ala, Ser or Pro
<220> FEATURE:
<221> NAME/KEY: misc_feature
<222> LOCATION: (30)..(30)
<223> OTHER INFORMATION: Xaa can be any amino acid except Asp, Pro, Asn or Ser
<220> FEATURE:
<221> NAME/KEY: misc_feature
<222> LOCATION: (31)..(31)
<223> OTHER INFORMATION: Xaa can be any amino acid except Ala, Glu, Asp or Ser
<220> FEATURE:
<221> NAME/KEY: misc_feature
<222> LOCATION: (32)..(32)
<223> OTHER INFORMATION: Xaa can be any amino acid except Asp, Asn, Val or His
<220> FEATURE:
<221> NAME/KEY: misc_feature
<222> LOCATION: (33)..(33)
<223> OTHER INFORMATION: Xaa can be any amino acid except Phe or Thr
<220> FEATURE:
<221> NAME/KEY: misc_feature
<222> LOCATION: (34)..(34)
<223> OTHER INFORMATION: Xaa can be any amino acid except Asn, Phe or Ile
<220> FEATURE:
<221> NAME/KEY: misc_feature
<222> LOCATION: (35)..(35)

```
<223> OTHER INFORMATION: Xaa can be any amino acid except Asn, Thr or
      Asp
<220> FEATURE:
<221> NAME/KEY: misc_feature
<222> LOCATION: (36)..(36)
<223> OTHER INFORMATION: Xaa can be any amino acid except Lys, Val or
      Pro
<220> FEATURE:
<221> NAME/KEY: misc_feature
<222> LOCATION: (37)..(37)
<223> OTHER INFORMATION: Xaa can be any amino acid except Gly, Pro or
      Ser
<220> FEATURE:
<221> NAME/KEY: misc_feature
<222> LOCATION: (38)..(38)
<223> OTHER INFORMATION: Xaa can be any amino acid except Tyr, Asn or
      Thr
<220> FEATURE:
<221> NAME/KEY: misc_feature
<222> LOCATION: (39)..(39)
<223> OTHER INFORMATION: Xaa can be any amino acid except Ser, Tyr or
      Ile
<220> FEATURE:
<221> NAME/KEY: misc_feature
<222> LOCATION: (40)..(40)
<223> OTHER INFORMATION: Xaa can be any amino acid except Phe or Ser

<400> SEQUENCE: 2

Cys Ser Xaa Lys Glu Asp Lys Gln Thr Thr Xaa Xaa Ile Trp Gly Leu
1               5                   10                  15

Lys Gln Xaa Trp Xaa Gly Xaa Pro Xaa Xaa Xaa Xaa Xaa Xaa Xaa Xaa
            20                  25                  30

Xaa Xaa Xaa Xaa Xaa Xaa Xaa Xaa
        35                  40


<210> SEQ ID NO 3
<211> LENGTH: 71
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (2)..(2)
<223> OTHER INFORMATION: Xaa can be Ala or Val
<220> FEATURE:
<221> NAME/KEY: misc_feature
<222> LOCATION: (5)..(5)
<223> OTHER INFORMATION: Xaa can be Glu or Asp
<220> FEATURE:
<221> NAME/KEY: misc_feature
<222> LOCATION: (8)..(8)
<223> OTHER INFORMATION: Xaa can be Thr or Pro
<220> FEATURE:
<221> NAME/KEY: misc_feature
<222> LOCATION: (10)..(10)
<223> OTHER INFORMATION: Xaa can be Thr or Val
<220> FEATURE:
<221> NAME/KEY: misc_feature
<222> LOCATION: (11)..(11)
<223> OTHER INFORMATION: Xaa can be Gly or Ala
<220> FEATURE:
<221> NAME/KEY: misc_feature
<222> LOCATION: (12)..(12)
<223> OTHER INFORMATION: Xaa can be Leu or Val
<220> FEATURE:
<221> NAME/KEY: misc_feature
<222> LOCATION: (13)..(13)
<223> OTHER INFORMATION: Xaa can be Tyr or Phe
<220> FEATURE:
<221> NAME/KEY: misc_feature
<222> LOCATION: (18)..(18)
<223> OTHER INFORMATION: Xaa can be Asp or Asn
<220> FEATURE:
<221> NAME/KEY: misc_feature
```

<222> LOCATION: (20)..(20)
<223> OTHER INFORMATION: Xaa can be Asp or Asn
<220> FEATURE:
<221> NAME/KEY: misc_feature
<222> LOCATION: (22)..(22)
<223> OTHER INFORMATION: Xaa can be Ser or Val
<220> FEATURE:
<221> NAME/KEY: misc_feature
<222> LOCATION: (23)..(23)
<223> OTHER INFORMATION: Xaa can be Ala, Ser or Thr
<220> FEATURE:
<221> NAME/KEY: misc_feature
<222> LOCATION: (24)..(24)
<223> OTHER INFORMATION: Xaa can be Ala or Ile
<220> FEATURE:
<221> NAME/KEY: misc_feature
<222> LOCATION: (25)..(25)
<223> OTHER INFORMATION: Xaa can be Thr or Pro
<220> FEATURE:
<221> NAME/KEY: misc_feature
<222> LOCATION: (26)..(26)
<223> OTHER INFORMATION: Xaa can be Ser, Asn or Lys
<220> FEATURE:
<221> NAME/KEY: misc_feature
<222> LOCATION: (39)..(39)
<223> OTHER INFORMATION: Xaa can be any amino acid
<220> FEATURE:
<221> NAME/KEY: misc_feature
<222> LOCATION: (41)..(41)
<223> OTHER INFORMATION: Xaa can be Asp or Asn
<220> FEATURE:
<221> NAME/KEY: misc_feature
<222> LOCATION: (44)..(44)
<223> OTHER INFORMATION: Xaa can be any amino acid
<220> FEATURE:
<221> NAME/KEY: misc_feature
<222> LOCATION: (48)..(48)
<223> OTHER INFORMATION: Xaa can be Val or Ala
<220> FEATURE:
<221> NAME/KEY: misc_feature
<222> LOCATION: (49)..(49)
<223> OTHER INFORMATION: Xaa can be any amino acid
<220> FEATURE:
<221> NAME/KEY: misc_feature
<222> LOCATION: (56)..(56)
<223> OTHER INFORMATION: Xaa can be any amino acid
<220> FEATURE:
<221> NAME/KEY: misc_feature
<222> LOCATION: (58)..(58)
<223> OTHER INFORMATION: Xaa can be any amino acid

<400> SEQUENCE: 3

```
Ser Xaa Lys Glu Xaa Lys Gln Xaa Thr Xaa Xaa Xaa Xaa Gly Leu Lys
1               5                   10                  15

Gln Xaa Trp Xaa Gly Xaa Xaa Xaa Xaa Xaa Gly Gly Gly Gly Gly Asn
            20                  25                  30

Phe Ser Ala Lys Glu Glu Xaa Ala Xaa Thr Arg Xaa Thr Phe Gly Xaa
        35                  40                  45

Xaa Lys Gln Tyr Asp Gly Ala Xaa Ile Xaa Glu Asn Gln Val Gln Asn
    50                  55                  60

Lys Phe Thr Ile Ser Asn Cys
65                  70
```

<210> SEQ ID NO 4
<211> LENGTH: 71
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (3)..(3)
<223> OTHER INFORMATION: Xaa can be Ala or Val
<220> FEATURE:
<221> NAME/KEY: misc_feature
<222> LOCATION: (6)..(6)
<223> OTHER INFORMATION: Xaa can be Glu or Asp
<220> FEATURE:
<221> NAME/KEY: misc_feature
<222> LOCATION: (9)..(9)
<223> OTHER INFORMATION: Xaa can be Thr or Pro
<220> FEATURE:
<221> NAME/KEY: misc_feature
<222> LOCATION: (11)..(11)
<223> OTHER INFORMATION: Xaa can be Thr or Val
<220> FEATURE:
<221> NAME/KEY: misc_feature
<222> LOCATION: (12)..(12)
<223> OTHER INFORMATION: Xaa can be Gly or Ala
<220> FEATURE:
<221> NAME/KEY: misc_feature
<222> LOCATION: (13)..(13)
<223> OTHER INFORMATION: Xaa can be Leu or Val
<220> FEATURE:
<221> NAME/KEY: misc_feature
<222> LOCATION: (14)..(14)
<223> OTHER INFORMATION: Xaa can be Tyr or Phe
<220> FEATURE:
<221> NAME/KEY: misc_feature
<222> LOCATION: (19)..(19)
<223> OTHER INFORMATION: Xaa can be Asp or Asn
<220> FEATURE:
<221> NAME/KEY: misc_feature
<222> LOCATION: (21)..(21)
<223> OTHER INFORMATION: Xaa can be Asp or Asn
<220> FEATURE:
<221> NAME/KEY: misc_feature
<222> LOCATION: (23)..(23)
<223> OTHER INFORMATION: Xaa can be Ser or Val
<220> FEATURE:
<221> NAME/KEY: misc_feature
<222> LOCATION: (24)..(24)
<223> OTHER INFORMATION: Xaa can be Ala, Ser or Thr
<220> FEATURE:
<221> NAME/KEY: misc_feature
<222> LOCATION: (25)..(25)
<223> OTHER INFORMATION: Xaa can be Ala or Ile
<220> FEATURE:
<221> NAME/KEY: misc_feature
<222> LOCATION: (26)..(26)
<223> OTHER INFORMATION: Xaa can be Thr or Pro
<220> FEATURE:
<221> NAME/KEY: misc_feature
<222> LOCATION: (27)..(27)
<223> OTHER INFORMATION: Xaa can be Ser, Asn or Lys
<220> FEATURE:
<221> NAME/KEY: misc_feature
<222> LOCATION: (40)..(40)
<223> OTHER INFORMATION: Xaa can be any amino acid
<220> FEATURE:
<221> NAME/KEY: misc_feature
<222> LOCATION: (42)..(42)
<223> OTHER INFORMATION: Xaa can be Asp or Asn
<220> FEATURE:
<221> NAME/KEY: misc_feature
<222> LOCATION: (45)..(45)
<223> OTHER INFORMATION: Xaa can be any amino acid
<220> FEATURE:
<221> NAME/KEY: misc_feature
<222> LOCATION: (49)..(49)
<223> OTHER INFORMATION: Xaa can be Val or Ala
<220> FEATURE:
<221> NAME/KEY: misc_feature
<222> LOCATION: (50)..(50)
<223> OTHER INFORMATION: Xaa can be any amino acid
<220> FEATURE:
<221> NAME/KEY: misc_feature
<222> LOCATION: (57)..(57)
<223> OTHER INFORMATION: Xaa can be any amino acid
<220> FEATURE:
<221> NAME/KEY: misc_feature
<222> LOCATION: (59)..(59)

<223> OTHER INFORMATION: Xaa can be any amino acid

<400> SEQUENCE: 4

Cys Ser Xaa Lys Glu Xaa Lys Gln Xaa Thr Xaa Xaa Xaa Xaa Gly Leu
1               5                   10                  15

Lys Gln Xaa Trp Xaa Gly Xaa Xaa Xaa Xaa Xaa Gly Gly Gly Gly Gly
            20                  25                  30

Asn Phe Ser Ala Lys Glu Glu Xaa Ala Xaa Thr Arg Xaa Thr Phe Gly
        35                  40                  45

Xaa Xaa Lys Gln Tyr Asp Gly Ala Xaa Ile Xaa Glu Asn Gln Val Gln
    50                  55                  60

Asn Lys Phe Thr Ile Ser Asn
65                  70

<210> SEQ ID NO 5
<211> LENGTH: 39
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (7)..(7)
<223> OTHER INFORMATION: Xaa can be any amino acid
<220> FEATURE:
<221> NAME/KEY: misc_feature
<222> LOCATION: (9)..(9)
<223> OTHER INFORMATION: Xaa can be Asp or Asn
<220> FEATURE:
<221> NAME/KEY: misc_feature
<222> LOCATION: (12)..(12)
<223> OTHER INFORMATION: Xaa can be any amino acid
<220> FEATURE:
<221> NAME/KEY: misc_feature
<222> LOCATION: (16)..(16)
<223> OTHER INFORMATION: Xaa can be Val or Ala
<220> FEATURE:
<221> NAME/KEY: misc_feature
<222> LOCATION: (17)..(17)
<223> OTHER INFORMATION: Xaa can be any amino acid
<220> FEATURE:
<221> NAME/KEY: misc_feature
<222> LOCATION: (24)..(24)
<223> OTHER INFORMATION: Xaa can be any amino acid
<220> FEATURE:
<221> NAME/KEY: misc_feature
<222> LOCATION: (26)..(26)
<223> OTHER INFORMATION: Xaa can be any amino acid

<400> SEQUENCE: 5

Phe Ser Ala Lys Glu Glu Xaa Ala Xaa Thr Arg Xaa Thr Phe Gly Xaa
1               5                   10                  15

Xaa Lys Gln Tyr Asp Gly Ala Xaa Ile Xaa Glu Asn Gln Val Gln Asn
            20                  25                  30

Lys Phe Thr Ile Ser Asn Cys
        35

<210> SEQ ID NO 6
<211> LENGTH: 39
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be Asp or Asn
<220> FEATURE:
<221> NAME/KEY: misc_feature
<222> LOCATION: (13)..(13)
<223> OTHER INFORMATION: Xaa can be any amino acid
<220> FEATURE:
<221> NAME/KEY: misc_feature
<222> LOCATION: (17)..(17)
<223> OTHER INFORMATION: Xaa can be Val or Ala
<220> FEATURE:
<221> NAME/KEY: misc_feature
<222> LOCATION: (18)..(18)
<223> OTHER INFORMATION: Xaa can be any amino acid
<220> FEATURE:
<221> NAME/KEY: misc_feature
<222> LOCATION: (25)..(25)
<223> OTHER INFORMATION: Xaa can be any amino acid
<220> FEATURE:
<221> NAME/KEY: misc_feature
<222> LOCATION: (27)..(27)
<223> OTHER INFORMATION: Xaa can be any amino acid

<400> SEQUENCE: 6

```
Cys Phe Ser Ala Lys Glu Glu Xaa Ala Xaa Thr Arg Xaa Thr Phe Gly
1               5                   10                  15

Xaa Xaa Lys Gln Tyr Asp Gly Ala Xaa Ile Xaa Glu Asn Gln Val Gln
            20                  25                  30

Asn Lys Phe Thr Ile Ser Asn
        35
```

<210> SEQ ID NO 7
<211> LENGTH: 40
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (4)..(4)
<223> OTHER INFORMATION: Xaa can be Glu or Asn
<220> FEATURE:
<221> NAME/KEY: misc_feature
<222> LOCATION: (8)..(8)
<223> OTHER INFORMATION: Xaa can be Pro or Ser
<220> FEATURE:
<221> NAME/KEY: misc_feature
<222> LOCATION: (10)..(10)
<223> OTHER INFORMATION: Xaa can be Ala or Ser
<220> FEATURE:
<221> NAME/KEY: misc_feature
<222> LOCATION: (20)..(20)
<223> OTHER INFORMATION: Xaa can be Glu or Gln
<220> FEATURE:
<221> NAME/KEY: misc_feature
<222> LOCATION: (22)..(22)
<223> OTHER INFORMATION: Xaa can be Pro or Thr
<220> FEATURE:
<221> NAME/KEY: misc_feature
<222> LOCATION: (23)..(23)
<223> OTHER INFORMATION: Xaa can be Ser or Val
<220> FEATURE:
<221> NAME/KEY: misc_feature
<222> LOCATION: (25)..(25)
<223> OTHER INFORMATION: Xaa can be Thr or Pro
<220> FEATURE:
<221> NAME/KEY: misc_feature
<222> LOCATION: (26)..(26)
<223> OTHER INFORMATION: Xaa can be Ser or Asn

<400> SEQUENCE: 7

```
Ser Val Lys Xaa Asp Lys Gln Xaa Thr Xaa Val Leu Trp Gly Ile Arg
1               5                   10                  15
```

Gln Asn Trp Xaa Gly Xaa Xaa Ala Xaa Xaa Gln Val Glu Val Glu Trp
            20                  25                  30

Gln Gln Arg Gly Trp Gly Gly Cys
        35                  40

<210> SEQ ID NO 8
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 8

Ser Val Lys Glu Asp Lys Gln Pro Thr Ala Val Leu Trp Gly Ile Arg
1               5                   10                  15

Gln Asn Trp Gln Gly Pro Ser Ala Thr Ser Gln Val Glu Val Glu Trp
            20                  25                  30

Gln Gln Arg Gly Trp Gly Gly Cys
        35                  40

<210> SEQ ID NO 9
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 9

Ser Val Lys Glu Asp Lys Gln Ser Thr Ala Val Leu Trp Gly Ile Arg
1               5                   10                  15

Gln Asn Trp Gln Gly Pro Ser Ala Thr Ser Gln Val Glu Val Glu Trp
            20                  25                  30

Gln Gln Arg Gly Trp Gly Gly Cys
        35                  40

<210> SEQ ID NO 10
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 10

Ser Val Lys Glu Asp Lys Gln Pro Thr Ser Val Leu Trp Gly Ile Arg
1               5                   10                  15

Gln Asn Trp Gln Gly Pro Ser Ala Thr Ser Gln Val Glu Val Glu Trp
            20                  25                  30

Gln Gln Arg Gly Trp Gly Gly Cys
        35                  40

<210> SEQ ID NO 11
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 11

Ser Val Lys Glu Asp Lys Gln Pro Thr Ala Val Leu Trp Gly Ile Arg
1               5                   10                  15

Gln Asn Trp Glu Gly Pro Ser Ala Thr Ser Gln Val Glu Val Glu Trp
            20                  25                  30

Gln Gln Arg Gly Trp Gly Gly Cys
35 40

<210> SEQ ID NO 12
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 12

Ser Val Lys Glu Asp Lys Gln Pro Thr Ala Val Leu Trp Gly Ile Arg
1 5 10 15

Gln Asn Trp Gln Gly Thr Ser Ala Thr Ser Gln Val Glu Val Glu Trp
20 25 30

Gln Gln Arg Gly Trp Gly Gly Cys
35 40

<210> SEQ ID NO 13
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 13

Ser Val Lys Glu Asp Lys Gln Pro Thr Ala Val Leu Trp Gly Ile Arg
1 5 10 15

Gln Asn Trp Gln Gly Pro Val Ala Thr Ser Gln Val Glu Val Glu Trp
20 25 30

Gln Gln Arg Gly Trp Gly Gly Cys
35 40

<210> SEQ ID NO 14
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 14

Ser Val Lys Glu Asp Lys Gln Pro Thr Ala Val Leu Trp Gly Ile Arg
1 5 10 15

Gln Asn Trp Gln Gly Pro Ser Ala Pro Ser Gln Val Glu Val Glu Trp
20 25 30

Gln Gln Arg Gly Trp Gly Gly Cys
35 40

<210> SEQ ID NO 15
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 15

Ser Val Lys Glu Asp Lys Gln Pro Thr Ala Val Leu Trp Gly Ile Arg
1 5 10 15

Gln Asn Trp Gln Gly Pro Ser Ala Thr Asn Gln Val Glu Val Glu Trp
20 25 30

Gln Gln Arg Gly Trp Gly Gly Cys
35 40

<210> SEQ ID NO 16
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 16

```
Ser Val Lys Glu Asp Lys Gln Ser Thr Ser Val Leu Trp Gly Ile Arg
1               5                   10                  15

Gln Asn Trp Gln Gly Pro Ser Ala Thr Ser Gln Val Glu Val Glu Trp
            20                  25                  30

Gln Gln Arg Gly Trp Gly Gly Cys
        35                  40
```

<210> SEQ ID NO 17
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 17

```
Ser Val Lys Glu Asp Lys Gln Ser Thr Ala Val Leu Trp Gly Ile Arg
1               5                   10                  15

Gln Asn Trp Glu Gly Pro Ser Ala Thr Ser Gln Val Glu Val Glu Trp
            20                  25                  30

Gln Gln Arg Gly Trp Gly Gly Cys
        35                  40
```

<210> SEQ ID NO 18
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 18

```
Ser Val Lys Glu Asp Lys Gln Ser Thr Ala Val Leu Trp Gly Ile Arg
1               5                   10                  15

Gln Asn Trp Gln Gly Thr Ser Ala Thr Ser Gln Val Glu Val Glu Trp
            20                  25                  30

Gln Gln Arg Gly Trp Gly Gly Cys
        35                  40
```

<210> SEQ ID NO 19
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 19

```
Ser Val Lys Glu Asp Lys Gln Ser Thr Ala Val Leu Trp Gly Ile Arg
1               5                   10                  15

Gln Asn Trp Gln Gly Pro Val Ala Thr Ser Gln Val Glu Val Glu Trp
            20                  25                  30

Gln Gln Arg Gly Trp Gly Gly Cys
        35                  40
```

<210> SEQ ID NO 20
<211> LENGTH: 40

<212> TYPE: PRT
<213> ORGANISM: Artificial Sequence
<220> FEATURE:
<223> OTHER INFORMATION: Ehrlichia antigenic peptide

<400> SEQUENCE: 20

```
Ser Val Lys Glu Asp Lys Gln Ser Thr Ala Val Leu Trp Gly Ile Arg
1               5                   10                  15

Gln Asn Trp Gln Gly Pro Ser Ala Pro Ser Gln Val Glu Val Glu Trp
            20                  25                  30

Gln Gln Arg Gly Trp Gly Gly Cys
        35                  40
```

<210> SEQ ID NO 21
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 21

```
Ser Val Lys Glu Asp Lys Gln Ser Thr Ala Val Leu Trp Gly Ile Arg
1               5                   10                  15

Gln Asn Trp Gln Gly Pro Ser Ala Pro Asn Gln Val Glu Val Glu Trp
            20                  25                  30

Gln Gln Arg Gly Trp Gly Gly Cys
        35                  40
```

<210> SEQ ID NO 22
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 22

```
Ser Val Lys Glu Asp Lys Gln Pro Thr Ser Val Leu Trp Gly Ile Arg
1               5                   10                  15

Gln Asn Trp Glu Gly Pro Ser Ala Thr Ser Gln Val Glu Val Glu Trp
            20                  25                  30

Gln Gln Arg Gly Trp Gly Gly Cys
        35                  40
```

<210> SEQ ID NO 23
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 23

```
Ser Val Lys Glu Asp Lys Gln Pro Thr Ser Val Leu Trp Gly Ile Arg
1               5                   10                  15

Gln Asn Trp Gln Gly Thr Ser Ala Thr Ser Gln Val Glu Val Glu Trp
            20                  25                  30

Gln Gln Arg Gly Trp Gly Gly Cys
        35                  40
```

<210> SEQ ID NO 24
<211> LENGTH: 40
<212> TYPE: PRT
<213> ORGANISM: Artificial Sequence
<220> FEATURE:

<223> OTHER INFORMATION: Ehrlichia antigenic peptide

<400> SEQUENCE: 24

```
Ser Val Lys Glu Asp Lys Gln Pro Thr Ser Val Leu Trp Gly Ile Arg
1               5                   10                  15

Gln Asn Trp Gln Gly Pro Val Ala Thr Ser Gln Val Glu Val Glu Trp
            20                  25                  30

Gln Gln Arg Gly Trp Gly Gly Cys
        35                  40
```

<210> SEQ ID NO 25
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 25

```
Ser Val Lys Glu Asp Lys Gln Pro Thr Ser Val Leu Trp Gly Ile Arg
1               5                   10                  15

Gln Asn Trp Gln Gly Pro Ser Ala Pro Ser Gln Val Glu Val Glu Trp
            20                  25                  30

Gln Gln Arg Gly Trp Gly Gly Cys
        35                  40
```

<210> SEQ ID NO 26
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 26

```
Ser Val Lys Glu Asp Lys Gln Pro Thr Ser Val Leu Trp Gly Ile Arg
1               5                   10                  15

Gln Asn Trp Gln Gly Pro Ser Ala Thr Asn Gln Val Glu Val Glu Trp
            20                  25                  30

Gln Gln Arg Gly Trp Gly Gly Cys
        35                  40
```

<210> SEQ ID NO 27
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 27

```
Ser Val Lys Glu Asp Lys Gln Pro Thr Ala Val Leu Trp Gly Ile Arg
1               5                   10                  15

Gln Asn Trp Glu Gly Thr Ser Ala Thr Ser Gln Val Glu Val Glu Trp
            20                  25                  30

Gln Gln Arg Gly Trp Gly Gly Cys
        35                  40
```

<210> SEQ ID NO 28
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 28

```
Ser Val Lys Glu Asp Lys Gln Pro Thr Ala Val Leu Trp Gly Ile Arg
1               5                   10                  15

Gln Asn Trp Glu Gly Pro Val Ala Thr Ser Gln Val Glu Val Glu Trp
            20                  25                  30

Gln Gln Arg Gly Trp Gly Gly Cys
        35                  40


<210> SEQ ID NO 29
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 29

Ser Val Lys Glu Asp Lys Gln Pro Thr Ala Val Leu Trp Gly Ile Arg
1               5                   10                  15

Gln Asn Trp Glu Gly Pro Ser Ala Pro Ser Gln Val Glu Val Glu Trp
            20                  25                  30

Gln Gln Arg Gly Trp Gly Gly Cys
        35                  40


<210> SEQ ID NO 30
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 30

Ser Val Lys Glu Asp Lys Gln Pro Thr Ala Val Leu Trp Gly Ile Arg
1               5                   10                  15

Gln Asn Trp Glu Gly Pro Ser Ala Thr Asn Gln Val Glu Val Glu Trp
            20                  25                  30

Gln Gln Arg Gly Trp Gly Gly Cys
        35                  40


<210> SEQ ID NO 31
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 31

Ser Val Lys Glu Asp Lys Gln Pro Thr Ala Val Leu Trp Gly Ile Arg
1               5                   10                  15

Gln Asn Trp Gln Gly Thr Val Ala Thr Ser Gln Val Glu Val Glu Trp
            20                  25                  30

Gln Gln Arg Gly Trp Gly Gly Cys
        35                  40


<210> SEQ ID NO 32
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 32

Ser Val Lys Glu Asp Lys Gln Pro Thr Ala Val Leu Trp Gly Ile Arg
1               5                   10                  15
```

```
Gln Asn Trp Gln Gly Thr Ser Ala Pro Ser Gln Val Glu Val Glu Trp
            20                  25                  30

Gln Gln Arg Gly Trp Gly Gly Cys
        35                  40


<210> SEQ ID NO 33
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 33

Ser Val Lys Glu Asp Lys Gln Pro Thr Ala Val Leu Trp Gly Ile Arg
1               5                   10                  15

Gln Asn Trp Gln Gly Thr Ser Ala Thr Asn Gln Val Glu Val Glu Trp
            20                  25                  30

Gln Gln Arg Gly Trp Gly Gly Cys
        35                  40


<210> SEQ ID NO 34
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 34

Ser Val Lys Glu Asp Lys Gln Pro Thr Ala Val Leu Trp Gly Ile Arg
1               5                   10                  15

Gln Asn Trp Glu Gly Thr Ser Ala Thr Asn Gln Val Glu Val Glu Trp
            20                  25                  30

Gln Gln Arg Gly Trp Gly Gly Cys
        35                  40


<210> SEQ ID NO 35
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 35

Ser Val Lys Glu Asp Lys Gln Pro Thr Ala Val Leu Trp Gly Ile Arg
1               5                   10                  15

Gln Asn Trp Gln Gly Pro Val Ala Thr Ser Gln Val Glu Val Glu Trp
            20                  25                  30

Gln Gln Arg Gly Trp Gly Gly Cys
        35                  40


<210> SEQ ID NO 36
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 36

Ser Val Lys Glu Asp Lys Gln Pro Thr Ala Val Leu Trp Gly Ile Arg
1               5                   10                  15

Gln Asn Trp Gln Gly Pro Val Ala Pro Ser Gln Val Glu Val Glu Trp
            20                  25                  30
```

```
Gln Gln Arg Gly Trp Gly Gly Cys
        35                  40


<210> SEQ ID NO 37
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 37

Ser Val Lys Glu Asp Lys Gln Pro Thr Ala Val Leu Trp Gly Ile Arg
1               5                   10                  15

Gln Asn Trp Gln Gly Pro Val Ala Thr Asn Gln Val Glu Val Glu Trp
            20                  25                  30

Gln Gln Arg Gly Trp Gly Gly Cys
        35                  40


<210> SEQ ID NO 38
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 38

Ser Val Lys Glu Asp Lys Gln Pro Thr Ala Val Leu Trp Gly Ile Arg
1               5                   10                  15

Gln Asn Trp Glu Gly Pro Val Ala Pro Asn Gln Val Glu Val Glu Trp
            20                  25                  30

Gln Gln Arg Gly Trp Gly Gly Cys
        35                  40


<210> SEQ ID NO 39
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 39

Ser Val Lys Asn Asp Lys Gln Pro Thr Ala Val Leu Trp Gly Ile Arg
1               5                   10                  15

Gln Asn Trp Gln Gly Pro Ser Ala Thr Ser Gln Val Glu Val Glu Trp
            20                  25                  30

Gln Gln Arg Gly Trp Gly Gly Cys
        35                  40


<210> SEQ ID NO 40
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 40

Ser Val Lys Asn Asp Lys Gln Ser Thr Ala Val Leu Trp Gly Ile Arg
1               5                   10                  15

Gln Asn Trp Gln Gly Pro Ser Ala Thr Ser Gln Val Glu Val Glu Trp
            20                  25                  30

Gln Gln Arg Gly Trp Gly Gly Cys
        35                  40
```

<210> SEQ ID NO 41
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 41

```
Ser Val Lys Asn Asp Lys Gln Pro Thr Ser Val Leu Trp Gly Ile Arg
1               5                   10                  15

Gln Asn Trp Gln Gly Pro Ser Ala Thr Ser Gln Val Glu Val Glu Trp
            20                  25                  30

Gln Gln Arg Gly Trp Gly Gly Cys
        35                  40
```

<210> SEQ ID NO 42
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 42

```
Ser Val Lys Asn Asp Lys Gln Pro Thr Ala Val Leu Trp Gly Ile Arg
1               5                   10                  15

Gln Asn Trp Glu Gly Pro Ser Ala Thr Ser Gln Val Glu Val Glu Trp
            20                  25                  30

Gln Gln Arg Gly Trp Gly Gly Cys
        35                  40
```

<210> SEQ ID NO 43
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 43

```
Ser Val Lys Asn Asp Lys Gln Pro Thr Ala Val Leu Trp Gly Ile Arg
1               5                   10                  15

Gln Asn Trp Gln Gly Thr Ser Ala Thr Ser Gln Val Glu Val Glu Trp
            20                  25                  30

Gln Gln Arg Gly Trp Gly Gly Cys
        35                  40
```

<210> SEQ ID NO 44
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 44

```
Ser Val Lys Asn Asp Lys Gln Pro Thr Ala Val Leu Trp Gly Ile Arg
1               5                   10                  15

Gln Asn Trp Gln Gly Pro Val Ala Thr Ser Gln Val Glu Val Glu Trp
            20                  25                  30

Gln Gln Arg Gly Trp Gly Gly Cys
        35                  40
```

<210> SEQ ID NO 45

<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 45

```
Ser Val Lys Asn Asp Lys Gln Pro Thr Ala Val Leu Trp Gly Ile Arg
1               5                   10                  15

Gln Asn Trp Gln Gly Pro Ser Ala Pro Ser Gln Val Glu Val Glu Trp
            20                  25                  30

Gln Gln Arg Gly Trp Gly Gly Cys
        35                  40
```

<210> SEQ ID NO 46
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 46

```
Ser Val Lys Asn Asp Lys Gln Pro Thr Ala Val Leu Trp Gly Ile Arg
1               5                   10                  15

Gln Asn Trp Gln Gly Pro Ser Ala Thr Asn Gln Val Glu Val Glu Trp
            20                  25                  30

Gln Gln Arg Gly Trp Gly Gly Cys
        35                  40
```

<210> SEQ ID NO 47
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 47

```
Ser Val Lys Asn Asp Lys Gln Ser Thr Ser Val Leu Trp Gly Ile Arg
1               5                   10                  15

Gln Asn Trp Gln Gly Pro Ser Ala Thr Ser Gln Val Glu Val Glu Trp
            20                  25                  30

Gln Gln Arg Gly Trp Gly Gly Cys
        35                  40
```

<210> SEQ ID NO 48
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 48

```
Ser Val Lys Asn Asp Lys Gln Ser Thr Ala Val Leu Trp Gly Ile Arg
1               5                   10                  15

Gln Asn Trp Glu Gly Pro Ser Ala Thr Ser Gln Val Glu Val Glu Trp
            20                  25                  30

Gln Gln Arg Gly Trp Gly Gly Cys
        35                  40
```

<210> SEQ ID NO 49
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 49

Ser Val Lys Asn Asp Lys Gln Ser Thr Ala Val Leu Trp Gly Ile Arg
1 5 10 15

Gln Asn Trp Gln Gly Thr Ser Ala Thr Ser Gln Val Glu Val Glu Trp
20 25 30

Gln Gln Arg Gly Trp Gly Gly Cys
35 40

<210> SEQ ID NO 50
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 50

Ser Val Lys Asn Asp Lys Gln Ser Thr Ala Val Leu Trp Gly Ile Arg
1 5 10 15

Gln Asn Trp Gln Gly Pro Val Ala Thr Ser Gln Val Glu Val Glu Trp
20 25 30

Gln Gln Arg Gly Trp Gly Gly Cys
35 40

<210> SEQ ID NO 51
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 51

Ser Val Lys Asn Asp Lys Gln Ser Thr Ala Val Leu Trp Gly Ile Arg
1 5 10 15

Gln Asn Trp Gln Gly Pro Ser Ala Pro Ser Gln Val Glu Val Glu Trp
20 25 30

Gln Gln Arg Gly Trp Gly Gly Cys
35 40

<210> SEQ ID NO 52
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 52

Ser Val Lys Asn Asp Lys Gln Ser Thr Ala Val Leu Trp Gly Ile Arg
1 5 10 15

Gln Asn Trp Gln Gly Pro Ser Ala Pro Asn Gln Val Glu Val Glu Trp
20 25 30

Gln Gln Arg Gly Trp Gly Gly Cys
35 40

<210> SEQ ID NO 53
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 53

Ser Val Lys Asn Asp Lys Gln Pro Thr Ser Val Leu Trp Gly Ile Arg
1               5                   10                  15

Gln Asn Trp Glu Gly Pro Ser Ala Thr Ser Gln Val Glu Val Glu Trp
            20                  25                  30

Gln Gln Arg Gly Trp Gly Gly Cys
        35                  40

<210> SEQ ID NO 54
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 54

Ser Val Lys Asn Asp Lys Gln Pro Thr Ser Val Leu Trp Gly Ile Arg
1               5                   10                  15

Gln Asn Trp Gln Gly Thr Ser Ala Thr Ser Gln Val Glu Val Glu Trp
            20                  25                  30

Gln Gln Arg Gly Trp Gly Gly Cys
        35                  40

<210> SEQ ID NO 55
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 55

Ser Val Lys Asn Asp Lys Gln Pro Thr Ser Val Leu Trp Gly Ile Arg
1               5                   10                  15

Gln Asn Trp Gln Gly Pro Val Ala Thr Ser Gln Val Glu Val Glu Trp
            20                  25                  30

Gln Gln Arg Gly Trp Gly Gly Cys
        35                  40

<210> SEQ ID NO 56
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 56

Ser Val Lys Asn Asp Lys Gln Pro Thr Ser Val Leu Trp Gly Ile Arg
1               5                   10                  15

Gln Asn Trp Gln Gly Pro Ser Ala Pro Ser Gln Val Glu Val Glu Trp
            20                  25                  30

Gln Gln Arg Gly Trp Gly Gly Cys
        35                  40

<210> SEQ ID NO 57
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 57

Ser Val Lys Asn Asp Lys Gln Pro Thr Ser Val Leu Trp Gly Ile Arg

-continued

```
1               5                   10                  15

Gln Asn Trp Gln Gly Pro Ser Ala Thr Asn Gln Val Glu Val Glu Trp
            20                  25                  30

Gln Gln Arg Gly Trp Gly Gly Cys
        35                  40


<210> SEQ ID NO 58
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 58

Ser Val Lys Asn Asp Lys Gln Pro Thr Ala Val Leu Trp Gly Ile Arg
1               5                   10                  15

Gln Asn Trp Glu Gly Thr Ser Ala Thr Ser Gln Val Glu Val Glu Trp
            20                  25                  30

Gln Gln Arg Gly Trp Gly Gly Cys
        35                  40


<210> SEQ ID NO 59
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 59

Ser Val Lys Asn Asp Lys Gln Pro Thr Ala Val Leu Trp Gly Ile Arg
1               5                   10                  15

Gln Asn Trp Glu Gly Pro Val Ala Thr Ser Gln Val Glu Val Glu Trp
            20                  25                  30

Gln Gln Arg Gly Trp Gly Gly Cys
        35                  40


<210> SEQ ID NO 60
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 60

Ser Val Lys Asn Asp Lys Gln Pro Thr Ala Val Leu Trp Gly Ile Arg
1               5                   10                  15

Gln Asn Trp Glu Gly Pro Ser Ala Pro Ser Gln Val Glu Val Glu Trp
            20                  25                  30

Gln Gln Arg Gly Trp Gly Gly Cys
        35                  40


<210> SEQ ID NO 61
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 61

Ser Val Lys Asn Asp Lys Gln Pro Thr Ala Val Leu Trp Gly Ile Arg
1               5                   10                  15

Gln Asn Trp Glu Gly Pro Ser Ala Thr Asn Gln Val Glu Val Glu Trp
```

```
            20                  25                  30

Gln Gln Arg Gly Trp Gly Gly Cys
        35                  40


<210> SEQ ID NO 62
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 62

Ser Val Lys Asn Asp Lys Gln Pro Thr Ala Val Leu Trp Gly Ile Arg
1               5                   10                  15

Gln Asn Trp Gln Gly Thr Val Ala Thr Ser Gln Val Glu Val Glu Trp
            20                  25                  30

Gln Gln Arg Gly Trp Gly Gly Cys
        35                  40


<210> SEQ ID NO 63
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 63

Ser Val Lys Asn Asp Lys Gln Pro Thr Ala Val Leu Trp Gly Ile Arg
1               5                   10                  15

Gln Asn Trp Gln Gly Thr Ser Ala Pro Ser Gln Val Glu Val Glu Trp
            20                  25                  30

Gln Gln Arg Gly Trp Gly Gly Cys
        35                  40


<210> SEQ ID NO 64
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 64

Ser Val Lys Asn Asp Lys Gln Pro Thr Ala Val Leu Trp Gly Ile Arg
1               5                   10                  15

Gln Asn Trp Gln Gly Thr Ser Ala Thr Asn Gln Val Glu Val Glu Trp
            20                  25                  30

Gln Gln Arg Gly Trp Gly Gly Cys
        35                  40


<210> SEQ ID NO 65
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 65

Ser Val Lys Asn Asp Lys Gln Pro Thr Ala Val Leu Trp Gly Ile Arg
1               5                   10                  15

Gln Asn Trp Glu Gly Thr Ser Ala Thr Asn Gln Val Glu Val Glu Trp
            20                  25                  30

Gln Gln Arg Gly Trp Gly Gly Cys
```

```
        35                  40


<210> SEQ ID NO 66
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 66

Ser Val Lys Asn Asp Lys Gln Pro Thr Ala Val Leu Trp Gly Ile Arg
1               5                   10                  15

Gln Asn Trp Gln Gly Pro Val Ala Thr Ser Gln Val Glu Val Glu Trp
            20                  25                  30

Gln Gln Arg Gly Trp Gly Gly Cys
        35                  40


<210> SEQ ID NO 67
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 67

Ser Val Lys Asn Asp Lys Gln Pro Thr Ala Val Leu Trp Gly Ile Arg
1               5                   10                  15

Gln Asn Trp Gln Gly Pro Val Ala Pro Ser Gln Val Glu Val Glu Trp
            20                  25                  30

Gln Gln Arg Gly Trp Gly Gly Cys
        35                  40


<210> SEQ ID NO 68
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 68

Ser Val Lys Asn Asp Lys Gln Pro Thr Ala Val Leu Trp Gly Ile Arg
1               5                   10                  15

Gln Asn Trp Gln Gly Pro Val Ala Thr Asn Gln Val Glu Val Glu Trp
            20                  25                  30

Gln Gln Arg Gly Trp Gly Gly Cys
        35                  40


<210> SEQ ID NO 69
<211> LENGTH: 40
<212> TYPE: PRT
<213> ORGANISM: Artificial Sequence
<220> FEATURE:
<223> OTHER INFORMATION: Ehrlichia antigenic peptide

<400> SEQUENCE: 69

Ser Val Lys Asn Asp Lys Gln Pro Thr Ala Val Leu Trp Gly Ile Arg
1               5                   10                  15

Gln Asn Trp Glu Gly Pro Val Ala Pro Asn Gln Val Glu Val Glu Trp
            20                  25                  30

Gln Gln Arg Gly Trp Gly Gly Cys
        35                  40
```

<210> SEQ ID NO 70
<211> LENGTH: 40
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (2)..(2)
<223> OTHER INFORMATION: Xaa can be Ala or Val
<220> FEATURE:
<221> NAME/KEY: misc_feature
<222> LOCATION: (5)..(5)
<223> OTHER INFORMATION: Xaa can be Glu or Asp
<220> FEATURE:
<221> NAME/KEY: misc_feature
<222> LOCATION: (8)..(8)
<223> OTHER INFORMATION: Xaa can be Thr or Pro
<220> FEATURE:
<221> NAME/KEY: misc_feature
<222> LOCATION: (10)..(10)
<223> OTHER INFORMATION: Xaa can be Ser, Val or Ala
<220> FEATURE:
<221> NAME/KEY: misc_feature
<222> LOCATION: (11)..(11)
<223> OTHER INFORMATION: Xaa can be Gly or Ala
<220> FEATURE:
<221> NAME/KEY: misc_feature
<222> LOCATION: (12)..(12)
<223> OTHER INFORMATION: Xaa can be Leu or Val
<220> FEATURE:
<221> NAME/KEY: misc_feature
<222> LOCATION: (13)..(13)
<223> OTHER INFORMATION: Xaa can be Tyr, Phe or Trp
<220> FEATURE:
<221> NAME/KEY: misc_feature
<222> LOCATION: (16)..(16)
<223> OTHER INFORMATION: Xaa can be Lys or Arg
<220> FEATURE:
<221> NAME/KEY: misc_feature
<222> LOCATION: (18)..(18)
<223> OTHER INFORMATION: Xaa can be Asp or Asn
<220> FEATURE:
<221> NAME/KEY: misc_feature
<222> LOCATION: (19)..(19)
<223> OTHER INFORMATION: Xaa can be Trp or Phe
<220> FEATURE:
<221> NAME/KEY: misc_feature
<222> LOCATION: (20)..(20)
<223> OTHER INFORMATION: Xaa can be Asp or Asn
<220> FEATURE:
<221> NAME/KEY: misc_feature
<222> LOCATION: (22)..(22)
<223> OTHER INFORMATION: Xaa can be Thr or Val
<220> FEATURE:
<221> NAME/KEY: misc_feature
<222> LOCATION: (23)..(23)
<223> OTHER INFORMATION: Xaa can be Ala, Ser or Thr
<220> FEATURE:
<221> NAME/KEY: misc_feature
<222> LOCATION: (24)..(24)
<223> OTHER INFORMATION: Xaa can be Ala or Ile
<220> FEATURE:
<221> NAME/KEY: misc_feature
<222> LOCATION: (25)..(25)
<223> OTHER INFORMATION: Xaa can be Thr or Pro
<220> FEATURE:
<221> NAME/KEY: misc_feature
<222> LOCATION: (26)..(26)
<223> OTHER INFORMATION: Xaa can be Ser, Asn and Lys
<220> FEATURE:
<221> NAME/KEY: misc_feature
<222> LOCATION: (27)..(39)
<223> OTHER INFORMATION: Xaa can be any amino acid

<400> SEQUENCE: 70

```
Ser Xaa Lys Asp Xaa Lys Gln Xaa Thr Xaa Xaa Xaa Xaa Gly Leu Xaa
1               5                   10                  15
```

Gln Xaa Xaa Xaa Gly Xaa Xaa Xaa Xaa Xaa Xaa Xaa Xaa Xaa Xaa Xaa
20 25 30

Xaa Xaa Xaa Xaa Xaa Xaa Xaa Cys
35 40

<210> SEQ ID NO 71
<211> LENGTH: 39
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (7)..(7)
<223> OTHER INFORMATION: Xaa can be any amino acid
<220> FEATURE:
<221> NAME/KEY: misc_feature
<222> LOCATION: (12)..(12)
<223> OTHER INFORMATION: Xaa can be any amino acid
<220> FEATURE:
<221> NAME/KEY: misc_feature
<222> LOCATION: (17)..(17)
<223> OTHER INFORMATION: Xaa can be any amino acid
<220> FEATURE:
<221> NAME/KEY: misc_feature
<222> LOCATION: (24)..(24)
<223> OTHER INFORMATION: Xaa can be any amino acid
<220> FEATURE:
<221> NAME/KEY: misc_feature
<222> LOCATION: (26)..(26)
<223> OTHER INFORMATION: Xaa can be any amino acid

<400> SEQUENCE: 71

Phe Ser Ala Lys Glu Glu Xaa Ala Glu Thr Arg Xaa Thr Phe Gly Leu
1 5 10 15

Xaa Lys Gln Tyr Asp Gly Ala Xaa Ile Xaa Glu Asn Gln Val Gln Asn
20 25 30

Lys Phe Thr Ile Ser Asn Cys
35

<210> SEQ ID NO 72
<211> LENGTH: 71
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (2)..(2)
<223> OTHER INFORMATION: Xaa can be Ala or Val
<220> FEATURE:
<221> NAME/KEY: misc_feature
<222> LOCATION: (5)..(5)
<223> OTHER INFORMATION: Xaa can be Glu or Asp
<220> FEATURE:
<221> NAME/KEY: misc_feature
<222> LOCATION: (8)..(8)
<223> OTHER INFORMATION: Xaa can be Thr or Pro
<220> FEATURE:
<221> NAME/KEY: misc_feature
<222> LOCATION: (10)..(10)
<223> OTHER INFORMATION: Xaa can be Thr or Val
<220> FEATURE:
<221> NAME/KEY: misc_feature
<222> LOCATION: (11)..(11)
<223> OTHER INFORMATION: Xaa can be Gly or Ala
<220> FEATURE:
<221> NAME/KEY: misc_feature
<222> LOCATION: (12)..(12)
<223> OTHER INFORMATION: Xaa can be Leu or Val
<220> FEATURE:
<221> NAME/KEY: misc_feature
<222> LOCATION: (13)..(13)
<223> OTHER INFORMATION: Xaa can be Tyr or Phe
<220> FEATURE:
<221> NAME/KEY: misc_feature
<222> LOCATION: (18)..(18)
<223> OTHER INFORMATION: Xaa can be Asp or Asn
<220> FEATURE:
<221> NAME/KEY: misc_feature
<222> LOCATION: (20)..(20)
<223> OTHER INFORMATION: Xaa can be Asp or Asn
<220> FEATURE:
<221> NAME/KEY: misc_feature
<222> LOCATION: (22)..(22)
<223> OTHER INFORMATION: Xaa can be Ser or Val
<220> FEATURE:
<221> NAME/KEY: misc_feature
<222> LOCATION: (23)..(23)
<223> OTHER INFORMATION: Xaa can be Ala, Ser or Thr
<220> FEATURE:
<221> NAME/KEY: misc_feature
<222> LOCATION: (24)..(24)
<223> OTHER INFORMATION: Xaa can be Ala or Ile
<220> FEATURE:
<221> NAME/KEY: misc_feature
<222> LOCATION: (25)..(25)
<223> OTHER INFORMATION: Xaa can be Thr or Pro
<220> FEATURE:
<221> NAME/KEY: misc_feature
<222> LOCATION: (26)..(26)
<223> OTHER INFORMATION: Xaa can be Ser, Asn or Lys
<220> FEATURE:
<221> NAME/KEY: misc_feature
<222> LOCATION: (39)..(39)
<223> OTHER INFORMATION: Xaa can be any amino acid
<220> FEATURE:
<221> NAME/KEY: misc_feature
<222> LOCATION: (44)..(44)
<223> OTHER INFORMATION: Xaa can be any amino acid
<220> FEATURE:
<221> NAME/KEY: misc_feature
<222> LOCATION: (49)..(49)
<223> OTHER INFORMATION: Xaa can be any amino acid
<220> FEATURE:
<221> NAME/KEY: misc_feature
<222> LOCATION: (56)..(56)
<223> OTHER INFORMATION: Xaa can be any amino acid
<220> FEATURE:
<221> NAME/KEY: misc_feature
<222> LOCATION: (58)..(58)
<223> OTHER INFORMATION: Xaa can be any amino acid

<400> SEQUENCE: 72

```
Ser Xaa Lys Glu Xaa Lys Gln Xaa Thr Xaa Xaa Xaa Xaa Gly Leu Lys
1               5                   10                  15

Gln Xaa Trp Xaa Gly Xaa Xaa Xaa Xaa Xaa Gly Gly Gly Gly Gly Asn
            20                  25                  30

Phe Ser Ala Lys Glu Glu Xaa Ala Glu Thr Arg Xaa Thr Phe Gly Leu
        35                  40                  45

Xaa Lys Gln Tyr Asp Gly Ala Xaa Ile Xaa Glu Asn Gln Val Gln Asn
    50                  55                  60

Lys Phe Thr Ile Ser Asn Cys
65                  70
```

<210> SEQ ID NO 73
<211> LENGTH: 72
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (3)..(3)
<223> OTHER INFORMATION: Xaa can be Ala or Val
<220> FEATURE:
<221> NAME/KEY: misc_feature
<222> LOCATION: (6)..(6)
<223> OTHER INFORMATION: Xaa can be Glu or Asp
<220> FEATURE:
<221> NAME/KEY: misc_feature
<222> LOCATION: (9)..(9)
<223> OTHER INFORMATION: Xaa can be Thr or Pro
<220> FEATURE:
<221> NAME/KEY: misc_feature
<222> LOCATION: (11)..(11)
<223> OTHER INFORMATION: Xaa can be Thr or Val
<220> FEATURE:
<221> NAME/KEY: misc_feature
<222> LOCATION: (12)..(12)
<223> OTHER INFORMATION: Xaa can be Gly or Ala
<220> FEATURE:
<221> NAME/KEY: misc_feature
<222> LOCATION: (13)..(13)
<223> OTHER INFORMATION: Xaa can be Leu or Val
<220> FEATURE:
<221> NAME/KEY: misc_feature
<222> LOCATION: (14)..(14)
<223> OTHER INFORMATION: Xaa can be Tyr or Phe
<220> FEATURE:
<221> NAME/KEY: misc_feature
<222> LOCATION: (19)..(19)
<223> OTHER INFORMATION: Xaa can be Asp or Asn
<220> FEATURE:
<221> NAME/KEY: misc_feature
<222> LOCATION: (21)..(21)
<223> OTHER INFORMATION: Xaa can be Asp or Asn
<220> FEATURE:
<221> NAME/KEY: misc_feature
<222> LOCATION: (23)..(23)
<223> OTHER INFORMATION: Xaa can be Ser or Val
<220> FEATURE:
<221> NAME/KEY: misc_feature
<222> LOCATION: (24)..(24)
<223> OTHER INFORMATION: Xaa can be Ala, Ser or Thr
<220> FEATURE:
<221> NAME/KEY: misc_feature
<222> LOCATION: (25)..(25)
<223> OTHER INFORMATION: Xaa can be Ala or Ile
<220> FEATURE:
<221> NAME/KEY: misc_feature
<222> LOCATION: (26)..(26)
<223> OTHER INFORMATION: Xaa can be Thr or Pro
<220> FEATURE:
<221> NAME/KEY: misc_feature
<222> LOCATION: (27)..(27)
<223> OTHER INFORMATION: Xaa can be Ser, Asn or Lys
<220> FEATURE:
<221> NAME/KEY: misc_feature
<222> LOCATION: (40)..(40)
<223> OTHER INFORMATION: Xaa can be any amino acid
<220> FEATURE:
<221> NAME/KEY: misc_feature
<222> LOCATION: (45)..(45)
<223> OTHER INFORMATION: Xaa can be any amino acid
<220> FEATURE:
<221> NAME/KEY: misc_feature
<222> LOCATION: (50)..(50)
<223> OTHER INFORMATION: Xaa can be any amino acid
<220> FEATURE:
<221> NAME/KEY: misc_feature
<222> LOCATION: (57)..(57)
<223> OTHER INFORMATION: Xaa can be any amino acid
<220> FEATURE:
<221> NAME/KEY: misc_feature
<222> LOCATION: (59)..(59)
<223> OTHER INFORMATION: Xaa can be any amino acid

<400> SEQUENCE: 73

Cys Ser Xaa Lys Glu Xaa Lys Gln Xaa Thr Xaa Xaa Xaa Xaa Gly Leu
1               5                   10                  15

Lys Gln Xaa Trp Xaa Gly Xaa Xaa Xaa Xaa Xaa Gly Gly Gly Gly Gly

```
            20                  25                  30

Asn Phe Ser Ala Lys Glu Glu Xaa Ala Glu Thr Arg Xaa Thr Phe Gly
        35                  40                  45

Leu Xaa Lys Gln Tyr Asp Gly Ala Xaa Ile Xaa Glu Asn Gln Val Gln
    50                  55                  60

Asn Lys Phe Thr Ile Ser Asn Cys
65                  70


<210> SEQ ID NO 74
<211> LENGTH: 13
<212> TYPE: PRT
<213> ORGANISM: Artificial Sequence
<220> FEATURE:
<223> OTHER INFORMATION: Ehrlichia antigenic peptide

<400> SEQUENCE: 74

Gln Arg Lys Asn Glu Pro Ser Glu Thr Asn Pro Gly Gln
1               5                   10


<210> SEQ ID NO 75
<211> LENGTH: 13
<212> TYPE: PRT
<213> ORGANISM: Artificial Sequence
<220> FEATURE:
<223> OTHER INFORMATION: Ehrlichia antigenic peptide

<400> SEQUENCE: 75

Met Val Glu Phe Glu Glu Leu Gln Arg Asn Trp His Pro
1               5                   10


<210> SEQ ID NO 76
<211> LENGTH: 13
<212> TYPE: PRT
<213> ORGANISM: Artificial Sequence
<220> FEATURE:
<223> OTHER INFORMATION: Ehrlichia antigenic peptide

<400> SEQUENCE: 76

Met Leu Glu Val Ser Trp Leu Ile Asp Phe Met Ala Pro
1               5                   10


<210> SEQ ID NO 77
<211> LENGTH: 13
<212> TYPE: PRT
<213> ORGANISM: Artificial Sequence
<220> FEATURE:
<223> OTHER INFORMATION: Ehrlichia antigenic peptide

<400> SEQUENCE: 77

Gln Asp Glu Asn Leu Tyr Ser Ser Ile Phe Phe Val Pro
1               5                   10


<210> SEQ ID NO 78
<211> LENGTH: 13
<212> TYPE: PRT
<213> ORGANISM: Artificial Sequence
<220> FEATURE:
<223> OTHER INFORMATION: Ehrlichia antigenic peptide

<400> SEQUENCE: 78

Gln Arg Lys Asn Asp Pro Ser Glu Thr Ser Pro Gly Gln
1               5                   10


<210> SEQ ID NO 79
<211> LENGTH: 13
```

<212> TYPE: PRT
<213> ORGANISM: Artificial Sequence
<220> FEATURE:
<223> OTHER INFORMATION: Ehrlichia antigenic peptide

<400> SEQUENCE: 79

Met Ala Pro Phe His Glu Leu Asp Val Asn Asn His Pro
1 5 10

<210> SEQ ID NO 80
<211> LENGTH: 13
<212> TYPE: PRT
<213> ORGANISM: Artificial Sequence
<220> FEATURE:
<223> OTHER INFORMATION: Ehrlichia antigenic peptide

<400> SEQUENCE: 80

Ser Leu Asn Val Ser Phe Leu Ile Asp Pro Met Ala Pro
1 5 10

<210> SEQ ID NO 81
<211> LENGTH: 13
<212> TYPE: PRT
<213> ORGANISM: Artificial Sequence
<220> FEATURE:
<223> OTHER INFORMATION: Ehrlichia antigenic peptide

<400> SEQUENCE: 81

Gln Asp Ser Asn Leu Tyr Ser Ser Ile Phe Phe Val Pro
1 5 10

<210> SEQ ID NO 82
<211> LENGTH: 6
<212> TYPE: PRT
<213> ORGANISM: Artificial Sequence
<220> FEATURE:
<223> OTHER INFORMATION: 6X His tag

<400> SEQUENCE: 82

His His His His His His
1 5

<210> SEQ ID NO 83
<211> LENGTH: 40
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (2)..(2)
<223> OTHER INFORMATION: Xaa can be Ala or Val
<220> FEATURE:
<221> NAME/KEY: misc_feature
<222> LOCATION: (11)..(11)
<223> OTHER INFORMATION: Xaa can be Gly or Ala
<220> FEATURE:
<221> NAME/KEY: misc_feature
<222> LOCATION: (18)..(18)
<223> OTHER INFORMATION: Xaa can be Glu or Gln
<220> FEATURE:
<221> NAME/KEY: misc_feature
<222> LOCATION: (22)..(22)
<223> OTHER INFORMATION: Xaa can be Ser or Val
<220> FEATURE:
<221> NAME/KEY: misc_feature
<222> LOCATION: (24)..(24)
<223> OTHER INFORMATION: Xaa can be Ala or Ile
<220> FEATURE:
<221> NAME/KEY: misc_feature
<222> LOCATION: (25)..(25)

```
<223> OTHER INFORMATION: Xaa can be Thr or Pro
<220> FEATURE:
<221> NAME/KEY: misc_feature
<222> LOCATION: (26)..(26)
<223> OTHER INFORMATION: Xaa can be Ser or Asn
<220> FEATURE:
<221> NAME/KEY: misc_feature
<222> LOCATION: (27)..(27)
<223> OTHER INFORMATION: Xaa can be any amino acid except His, Asn, Ser
      or Ala
<220> FEATURE:
<221> NAME/KEY: misc_feature
<222> LOCATION: (28)..(28)
<223> OTHER INFORMATION: Xaa can be any amino acid except Ala, Ser or
      Pro
<220> FEATURE:
<221> NAME/KEY: misc_feature
<222> LOCATION: (29)..(29)
<223> OTHER INFORMATION: Xaa can be any amino acid except Asp, Pro, Asn
      or Ser
<220> FEATURE:
<221> NAME/KEY: misc_feature
<222> LOCATION: (30)..(30)
<223> OTHER INFORMATION: Xaa can be any amino acid except Ala, Glu, Asp
      or Ser
<220> FEATURE:
<221> NAME/KEY: misc_feature
<222> LOCATION: (31)..(31)
<223> OTHER INFORMATION: Xaa can be any amino acid except Asp, Asn, Val
      or Arg
<220> FEATURE:
<221> NAME/KEY: misc_feature
<222> LOCATION: (32)..(32)
<223> OTHER INFORMATION: Xaa can be any amino acid except Phe or Thr
<220> FEATURE:
<221> NAME/KEY: misc_feature
<222> LOCATION: (33)..(33)
<223> OTHER INFORMATION: Xaa can be any amino acid except Asn, Phe or
      Ile
<220> FEATURE:
<221> NAME/KEY: misc_feature
<222> LOCATION: (34)..(34)
<223> OTHER INFORMATION: Xaa can be any amino acid except Asn, Thr or
      Asp
<220> FEATURE:
<221> NAME/KEY: misc_feature
<222> LOCATION: (35)..(35)
<223> OTHER INFORMATION: Xaa can be any amino acid except Lys, Val or
      Pro
<220> FEATURE:
<221> NAME/KEY: misc_feature
<222> LOCATION: (36)..(36)
<223> OTHER INFORMATION: Xaa can be any amino acid except Gly, Pro or
      Ser
<220> FEATURE:
<221> NAME/KEY: misc_feature
<222> LOCATION: (37)..(37)
<223> OTHER INFORMATION: Xaa can be any amino acid except Tyr, Asn or
      Thr
<220> FEATURE:
<221> NAME/KEY: misc_feature
<222> LOCATION: (38)..(38)
<223> OTHER INFORMATION: Xaa can be any amino acid except Ser, Tyr or
      Ile
<220> FEATURE:
<221> NAME/KEY: misc_feature
<222> LOCATION: (39)..(39)
<223> OTHER INFORMATION: Xaa can be any amino acid except Phe or Ser

<400> SEQUENCE: 83

Ser Xaa Lys Glu Asp Lys Gln Thr Thr Thr Xaa Ile Trp Gly Leu Lys
1               5                   10                  15

Gln Xaa Trp Asp Gly Xaa Pro Xaa Xaa Xaa Xaa Xaa Xaa Xaa Xaa Xaa
            20                  25                  30

Xaa Xaa Xaa Xaa Xaa Xaa Xaa Cys
        35                  40
```

<210> SEQ ID NO 84
<211> LENGTH: 26
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (2)..(2)
<223> OTHER INFORMATION: Xaa can be Ala or Val
<220> FEATURE:
<221> NAME/KEY: misc_feature
<222> LOCATION: (10)..(10)
<223> OTHER INFORMATION: Xaa can be Thr or Val
<220> FEATURE:
<221> NAME/KEY: misc_feature
<222> LOCATION: (11)..(11)
<223> OTHER INFORMATION: Xaa can be Gly or Ala
<220> FEATURE:
<221> NAME/KEY: misc_feature
<222> LOCATION: (18)..(18)
<223> OTHER INFORMATION: Xaa can be Glu or Gln
<220> FEATURE:
<221> NAME/KEY: misc_feature
<222> LOCATION: (20)..(20)
<223> OTHER INFORMATION: Xaa can be Asp or Asn
<220> FEATURE:
<221> NAME/KEY: misc_feature
<222> LOCATION: (22)..(22)
<223> OTHER INFORMATION: Xaa can be Ser or Val
<220> FEATURE:
<221> NAME/KEY: misc_feature
<222> LOCATION: (24)..(24)
<223> OTHER INFORMATION: Xaa can be Ala or Ile
<220> FEATURE:
<221> NAME/KEY: misc_feature
<222> LOCATION: (25)..(25)
<223> OTHER INFORMATION: Xaa can be Thr or Pro
<220> FEATURE:
<221> NAME/KEY: misc_feature
<222> LOCATION: (26)..(26)
<223> OTHER INFORMATION: Xaa can be Ser, Asn or Lys

<400> SEQUENCE: 84

```
Ser Xaa Lys Glu Asp Lys Gln Thr Thr Xaa Xaa Ile Trp Gly Leu Lys
1               5                   10                  15

Gln Xaa Trp Xaa Gly Xaa Pro Xaa Xaa Xaa
            20                  25
```

<210> SEQ ID NO 85
<211> LENGTH: 72
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (2)..(2)
<223> OTHER INFORMATION: Xaa can be Ala or Val
<220> FEATURE:
<221> NAME/KEY: misc_feature
<222> LOCATION: (5)..(5)
<223> OTHER INFORMATION: Xaa can be Glu or Asp
<220> FEATURE:
<221> NAME/KEY: misc_feature
<222> LOCATION: (8)..(8)
<223> OTHER INFORMATION: Xaa can be Thr or Pro
<220> FEATURE:
<221> NAME/KEY: misc_feature
<222> LOCATION: (10)..(10)
<223> OTHER INFORMATION: Xaa can be Thr or Val
<220> FEATURE:
<221> NAME/KEY: misc_feature
<222> LOCATION: (11)..(11)

```
<223> OTHER INFORMATION: Xaa can be Gly or Ala
<220> FEATURE:
<221> NAME/KEY: misc_feature
<222> LOCATION: (12)..(12)
<223> OTHER INFORMATION: Xaa can be Leu or Val
<220> FEATURE:
<221> NAME/KEY: misc_feature
<222> LOCATION: (13)..(13)
<223> OTHER INFORMATION: Xaa can be Tyr or Phe
<220> FEATURE:
<221> NAME/KEY: misc_feature
<222> LOCATION: (18)..(18)
<223> OTHER INFORMATION: Xaa can be Asp or Asn
<220> FEATURE:
<221> NAME/KEY: misc_feature
<222> LOCATION: (20)..(20)
<223> OTHER INFORMATION: Xaa can be Asp or Asn
<220> FEATURE:
<221> NAME/KEY: misc_feature
<222> LOCATION: (22)..(22)
<223> OTHER INFORMATION: Xaa can be Ser or Val
<220> FEATURE:
<221> NAME/KEY: misc_feature
<222> LOCATION: (23)..(23)
<223> OTHER INFORMATION: Xaa can be Ala, Ser or Thr
<220> FEATURE:
<221> NAME/KEY: misc_feature
<222> LOCATION: (24)..(24)
<223> OTHER INFORMATION: Xaa can be Ala or Ile
<220> FEATURE:
<221> NAME/KEY: misc_feature
<222> LOCATION: (25)..(25)
<223> OTHER INFORMATION: Xaa can be Thr or Pro
<220> FEATURE:
<221> NAME/KEY: misc_feature
<222> LOCATION: (26)..(26)
<223> OTHER INFORMATION: Xaa can be Ser, Asn or Lys
<220> FEATURE:
<221> NAME/KEY: misc_feature
<222> LOCATION: (40)..(40)
<223> OTHER INFORMATION: Xaa can be any amino acid
<220> FEATURE:
<221> NAME/KEY: misc_feature
<222> LOCATION: (45)..(45)
<223> OTHER INFORMATION: Xaa can be any amino acid
<220> FEATURE:
<221> NAME/KEY: misc_feature
<222> LOCATION: (50)..(50)
<223> OTHER INFORMATION: Xaa can be any amino acid
<220> FEATURE:
<221> NAME/KEY: misc_feature
<222> LOCATION: (57)..(57)
<223> OTHER INFORMATION: Xaa can be any amino acid
<220> FEATURE:
<221> NAME/KEY: misc_feature
<222> LOCATION: (59)..(59)
<223> OTHER INFORMATION: Xaa can be any amino acid

<400> SEQUENCE: 85

Ser Xaa Lys Glu Xaa Lys Gln Xaa Thr Xaa Xaa Xaa Xaa Gly Leu Lys
1               5                   10                  15

Gln Xaa Trp Xaa Gly Xaa Xaa Xaa Xaa Xaa Gly Gly Gly Gly Gly Asn
            20                  25                  30

Phe Ser Ala Lys Glu Glu Lys Xaa Ala Asp Thr Arg Xaa Thr Phe Gly
        35                  40                  45

Leu Xaa Lys Gln Thr Asp Gly Ala Xaa Ile Xaa Glu Asn Gln Val Gln
    50                  55                  60

Asn Lys Phe Thr Ile Ser Asn Cys
65                  70


<210> SEQ ID NO 86
<211> LENGTH: 26
<212> TYPE: PRT
```

-continued

```
<213> ORGANISM: Artificial Sequence
<220> FEATURE:
<223> OTHER INFORMATION: Ehrlichia antigenic peptide
<220> FEATURE:
<221> NAME/KEY: misc_feature
<222> LOCATION: (2)..(2)
<223> OTHER INFORMATION: Xaa can be Ala or Val
<220> FEATURE:
<221> NAME/KEY: misc_feature
<222> LOCATION: (5)..(5)
<223> OTHER INFORMATION: Xaa can be Glu or Asp
<220> FEATURE:
<221> NAME/KEY: misc_feature
<222> LOCATION: (8)..(8)
<223> OTHER INFORMATION: Xaa can be Thr or Pro
<220> FEATURE:
<221> NAME/KEY: misc_feature
<222> LOCATION: (10)..(10)
<223> OTHER INFORMATION: Xaa can be Thr or Val
<220> FEATURE:
<221> NAME/KEY: misc_feature
<222> LOCATION: (11)..(11)
<223> OTHER INFORMATION: Xaa can be Gly or Ala
<220> FEATURE:
<221> NAME/KEY: misc_feature
<222> LOCATION: (12)..(12)
<223> OTHER INFORMATION: Xaa can be Leu or Val
<220> FEATURE:
<221> NAME/KEY: misc_feature
<222> LOCATION: (13)..(13)
<223> OTHER INFORMATION: Xaa can be Tyr or Phe
<220> FEATURE:
<221> NAME/KEY: misc_feature
<222> LOCATION: (18)..(18)
<223> OTHER INFORMATION: Xaa can be Asp or Asn
<220> FEATURE:
<221> NAME/KEY: misc_feature
<222> LOCATION: (20)..(20)
<223> OTHER INFORMATION: Xaa can be Asp or Asn
<220> FEATURE:
<221> NAME/KEY: misc_feature
<222> LOCATION: (22)..(22)
<223> OTHER INFORMATION: Xaa can be Ser or Val
<220> FEATURE:
<221> NAME/KEY: misc_feature
<222> LOCATION: (23)..(23)
<223> OTHER INFORMATION: Xaa can be Ala, Ser or Thr
<220> FEATURE:
<221> NAME/KEY: misc_feature
<222> LOCATION: (24)..(24)
<223> OTHER INFORMATION: Xaa can be Ala or Ile
<220> FEATURE:
<221> NAME/KEY: misc_feature
<222> LOCATION: (25)..(25)
<223> OTHER INFORMATION: Xaa can be Thr or Pro
<220> FEATURE:
<221> NAME/KEY: misc_feature
<222> LOCATION: (26)..(26)
<223> OTHER INFORMATION: Xaa can be Ser, Asn or Lys

<400> SEQUENCE: 86

Ser Xaa Lys Glu Xaa Lys Gln Xaa Thr Xaa Xaa Xaa Xaa Gly Leu Lys
1               5                   10                  15

Gln Xaa Trp Xaa Gly Xaa Xaa Xaa Xaa Xaa
            20                  25
```